US011672252B2

(12) United States Patent
Bal et al.

(10) Patent No.: US 11,672,252 B2
(45) Date of Patent: *Jun. 13, 2023

(54) ANTIFUNGAL COMPOSITES AND METHODS THEREOF

(71) Applicant: SINTX Technologies, Inc., Salt Lake City, UT (US)

(72) Inventors: Bhajanjit Singh Bal, Salt Lake City, UT (US); Bryan J. McEntire, Salt Lake City, UT (US); Ryan M. Bock, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/156,188

(22) Filed: Jan. 22, 2021

(65) Prior Publication Data
US 2021/0227831 A1 Jul. 29, 2021

Related U.S. Application Data

(60) Provisional application No. 62/965,451, filed on Jan. 24, 2020.

(51) Int. Cl.
| | |
|---|---|
| *A01N 59/00* | (2006.01) |
| *A61K 6/76* | (2020.01) |
| *A01N 25/10* | (2006.01) |
| *A01N 25/12* | (2006.01) |
| *A61C 13/087* | (2006.01) |
| *A61K 6/889* | (2020.01) |

(52) U.S. Cl.
CPC .............. *A01N 59/00* (2013.01); *A01N 25/10* (2013.01); *A01N 25/12* (2013.01); *A61C 13/087* (2013.01); *A61K 6/76* (2020.01); *A61K 6/889* (2020.01); *A61C 2201/00* (2013.01)

(58) Field of Classification Search
CPC . A61K 6/884; A61K 8/25; A61K 6/30; A61K 6/76; A61K 6/71; A61K 6/889; A61Q 11/00; A61Q 17/005; A01N 59/00
See application file for complete search history.

(56) References Cited

U.S. PATENT DOCUMENTS

| | | | |
|---|---|---|---|
| 9,896,585 B2 | 2/2018 | Pabla et al. | |
| 2009/0162695 A1 | 6/2009 | Hevesi et al. | |
| 2011/0256408 A1 | 10/2011 | Wang et al. | |
| 2012/0132104 A1* | 5/2012 | Ruppert | A61K 6/77 546/14 |
| 2013/0302509 A1 | 11/2013 | McEntire et al. | |
| 2020/0079651 A1 | 3/2020 | McEntire et al. | |

OTHER PUBLICATIONS

Song, Wenjing, and Shaohua Ge. "Application of Antimicrobial Nanoparticles in Dentistry." Molecules (Basel, Switzerland) vol. 24,6 1033. Mar. 15, 2019, doi:10.3390/molecules24061033 (Year: 2019).*
Suganya S, Ahila S C, Kumar B M, Kumar M V. Evaluation and comparison of anti-Candida effect of heat cure polymethylmethacrylate resin enforced with silver nanoparticles and conventional heat cure resins: An in vitro study. Indian J Dent Res 2014;25:204-7 (Year: 2014).*
Rambo WM Jr. Treatment of lumbar discitis using silicon nitride spinal spacers: A case series and literature review. Int J Surg Case Rep. 2018;43:61-68. doi: 10.1016/j.ijscr.2018.02.009. Epub Feb. 10, 2018. PMID: 29462728; PMCID: PMC5832668. (Year: 2018).*
International Search Report and Written Opinion in corresponding Application No. PCT/US2021/014725 dated Apr. 29, 2021, 7 pages.
Pezzotti et al., Silicon Nitride Bioceramics Induce Chemically Driven Lysis in Porphyromonas gingivalis, Langmuir, vol. 32, Mar. 5, 2016, pp. 3024-3035.

* cited by examiner

*Primary Examiner* — Tracy Liu
(74) *Attorney, Agent, or Firm* — Polsinelli PC

(57) ABSTRACT

Disclosed herein are antifungal composites, devices, and methods to reduce or prevent a fungus from growing on the antifungal composite. The antifungal composite and devices thereof may include a biocompatible polymer and a $Si_3N_4$ powder loaded in at least a portion of the biocompatible polymer. The polymer may be a thermoplastic polymer such as a poly(methyl methacrylate) (PMMA) resin and the $Si_3N_4$ powder may be present in a concentration of about 1 vol. % to about 30 vol. % in the thermoplastic polymer.

21 Claims, 41 Drawing Sheets
(38 of 41 Drawing Sheet(s) Filed in Color)

As-cultured yeast polymorph

50 μm

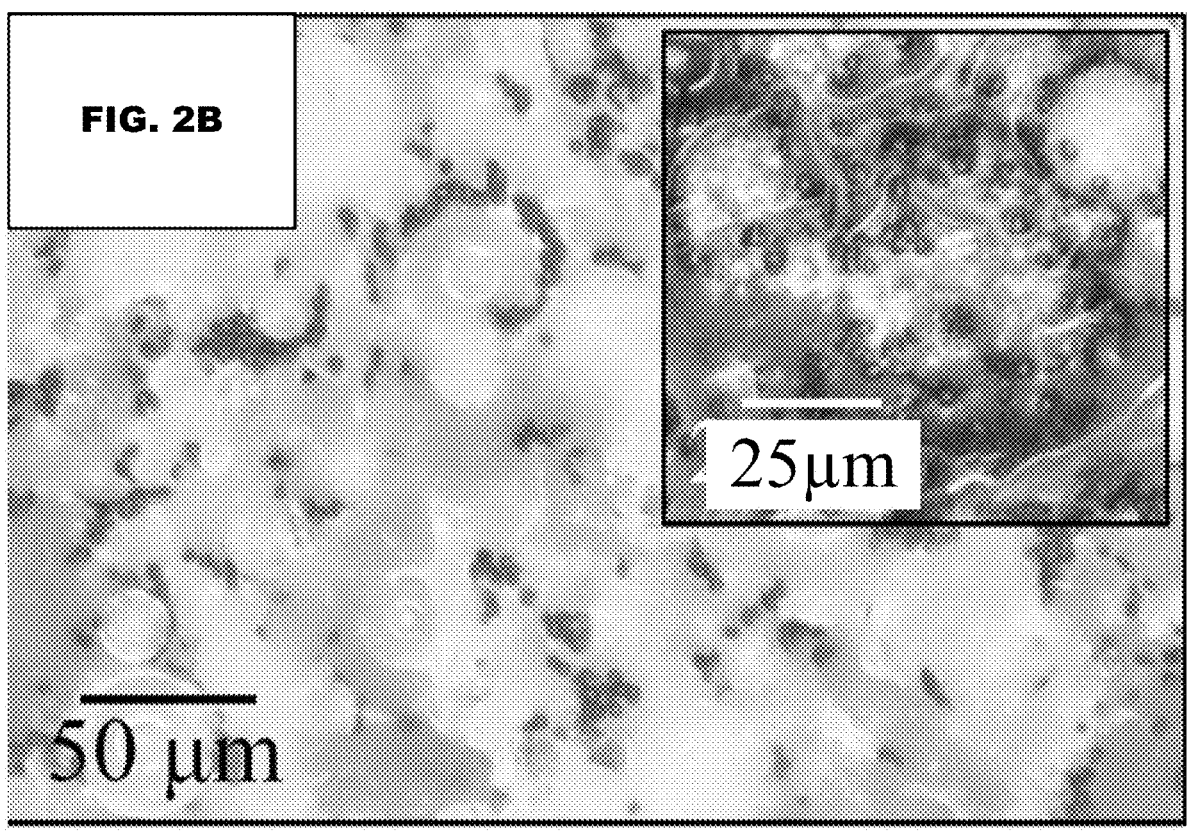

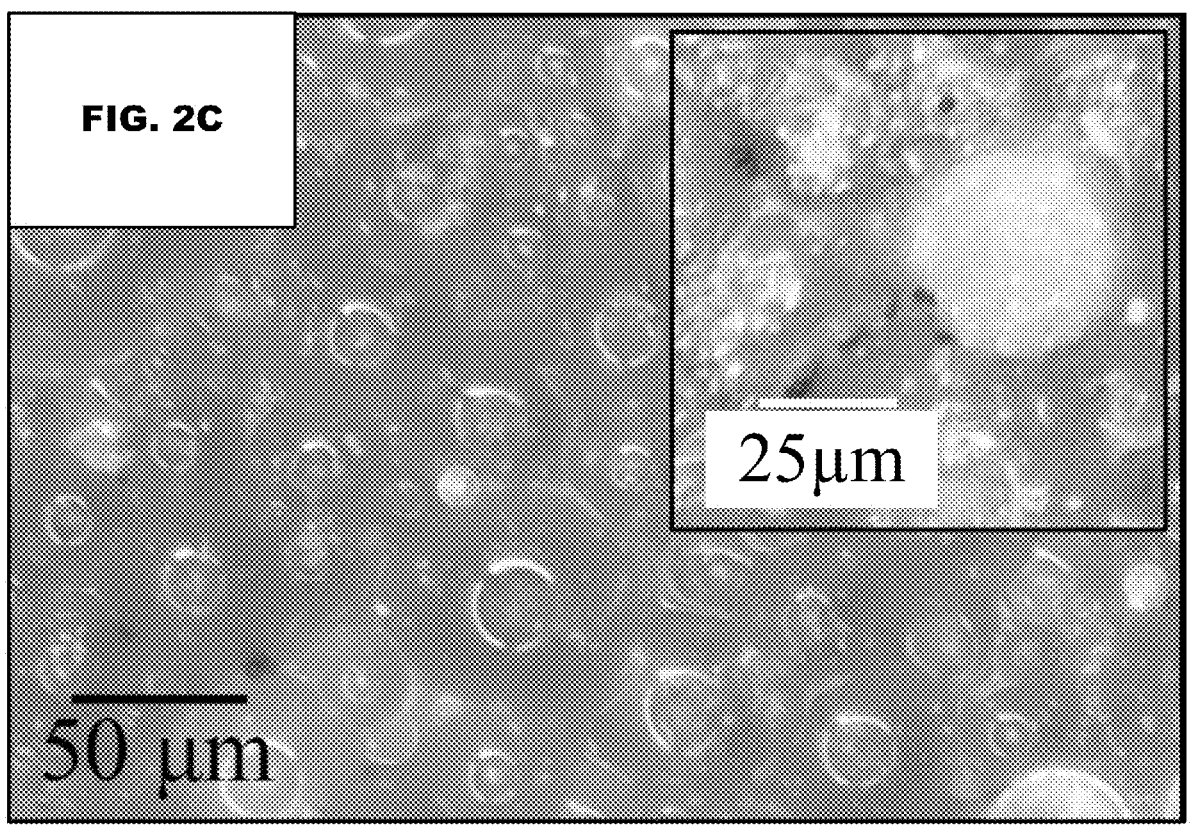

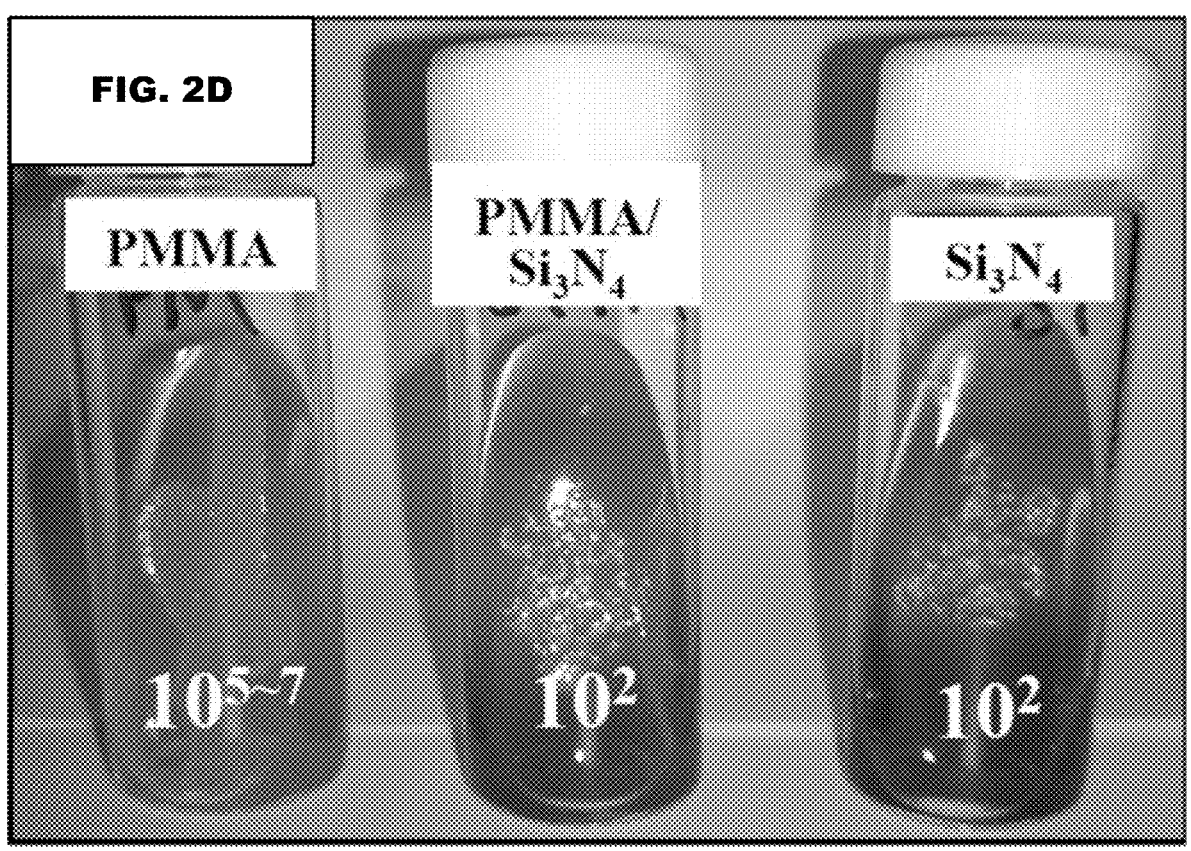

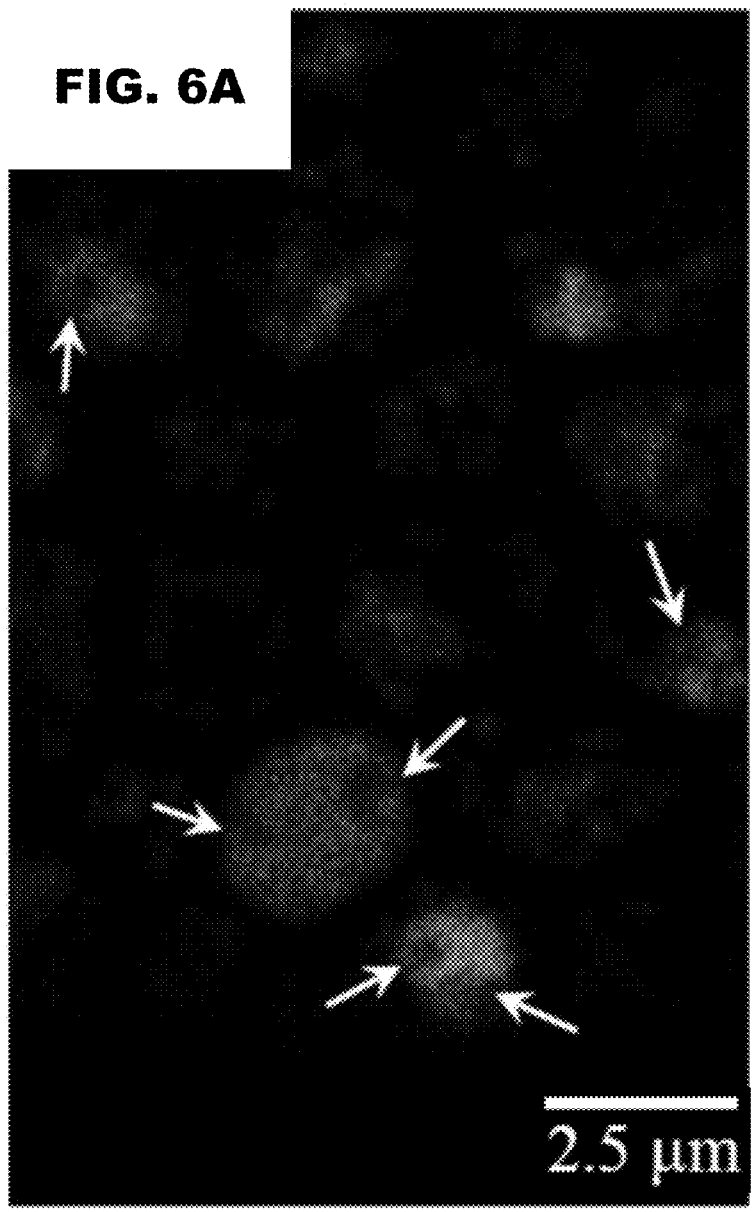

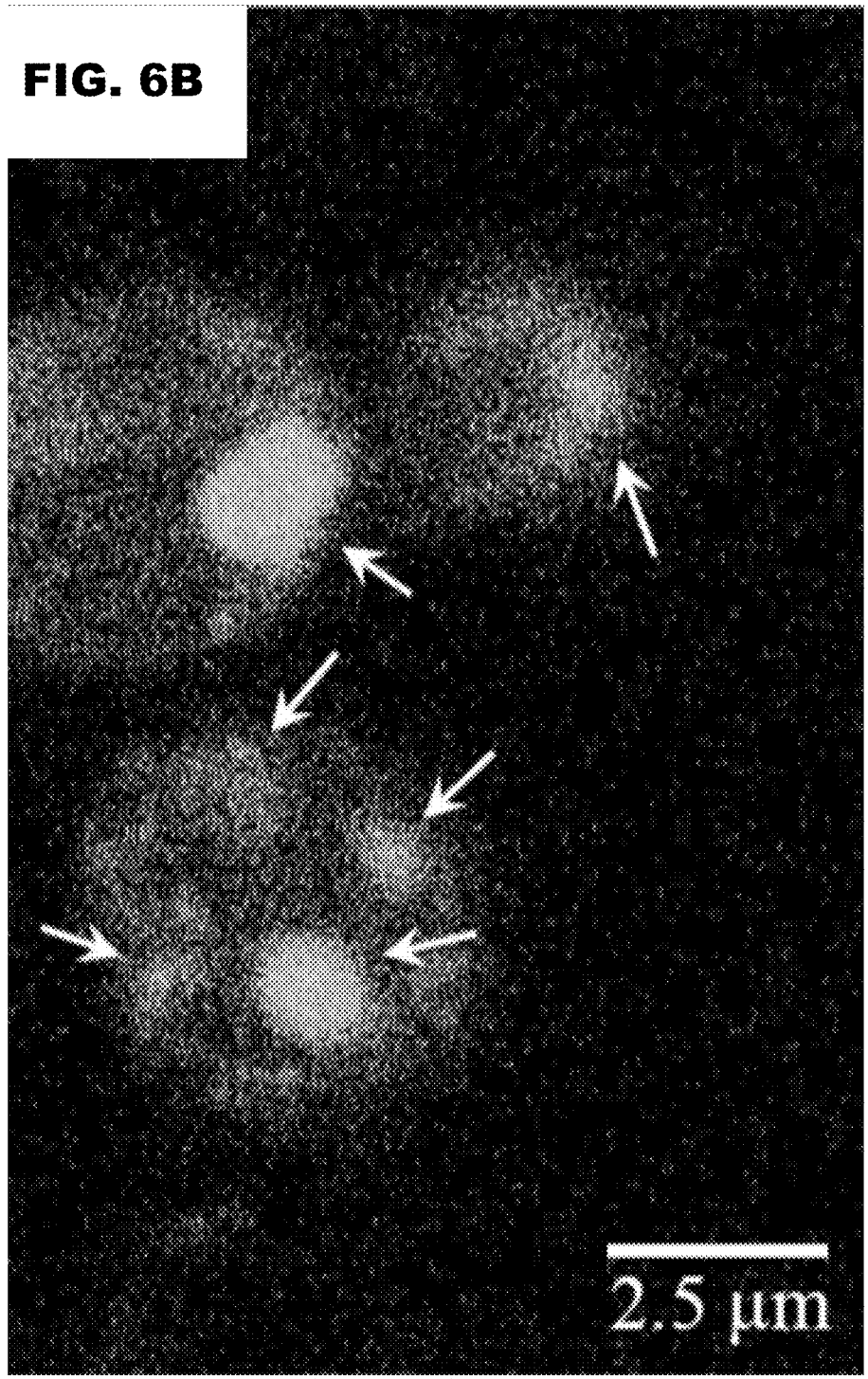

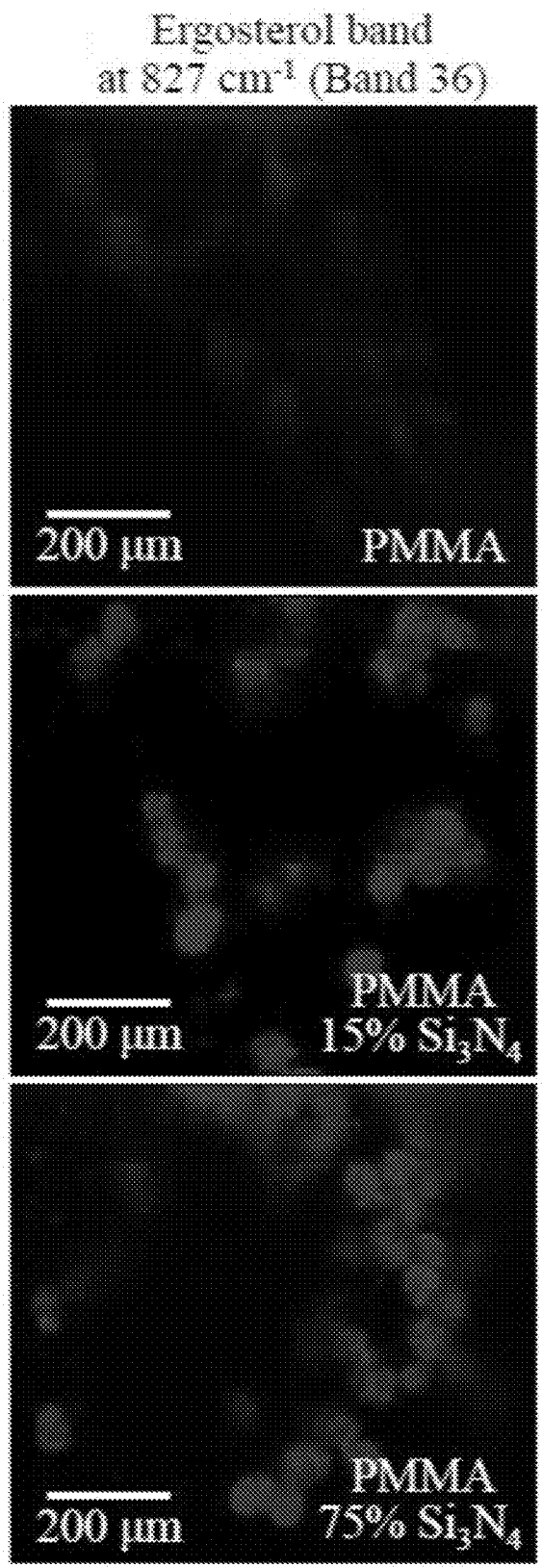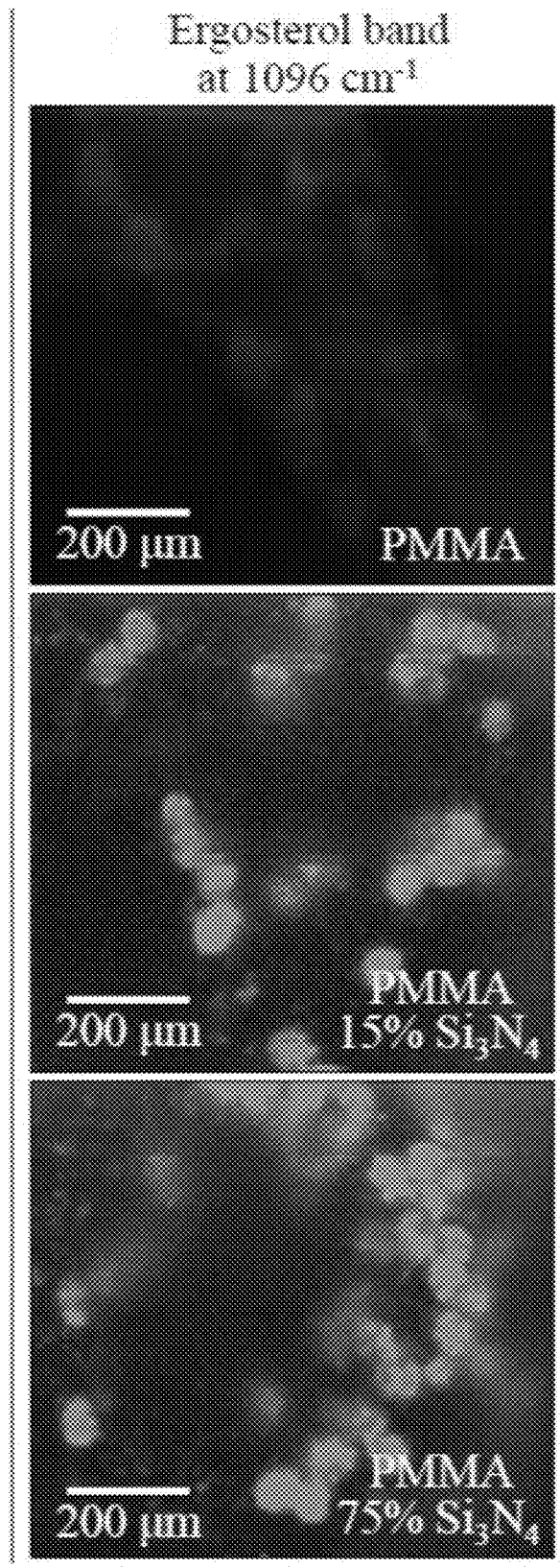
FIG. 12C  FIG. 12D

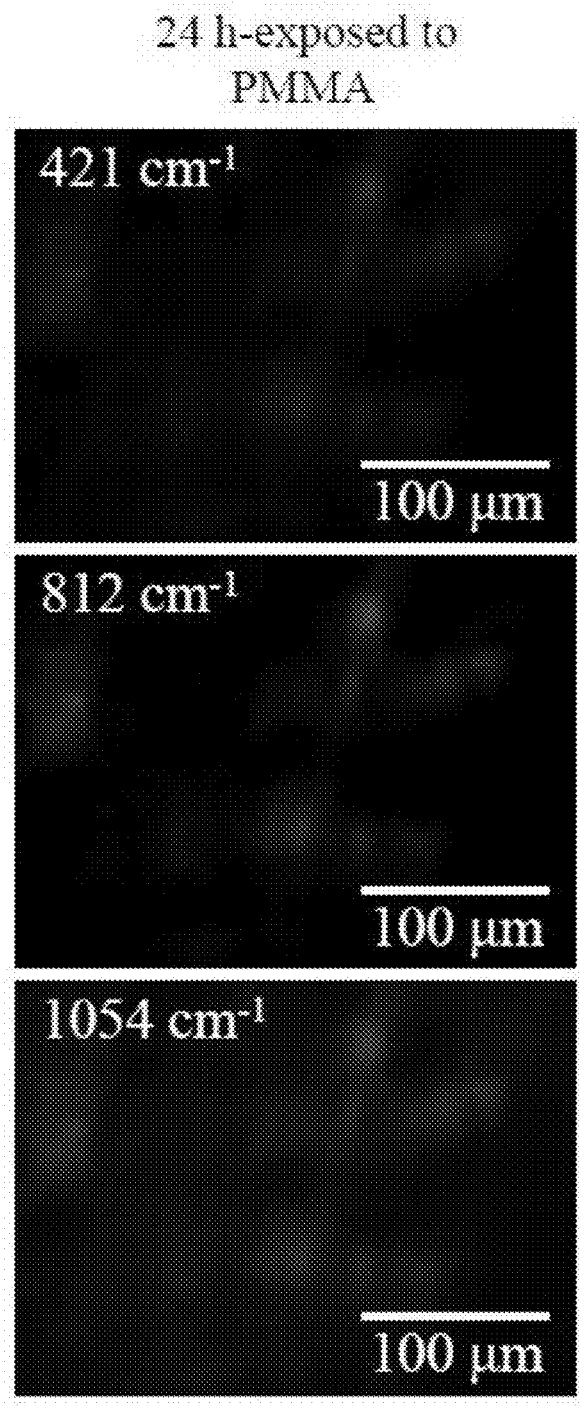
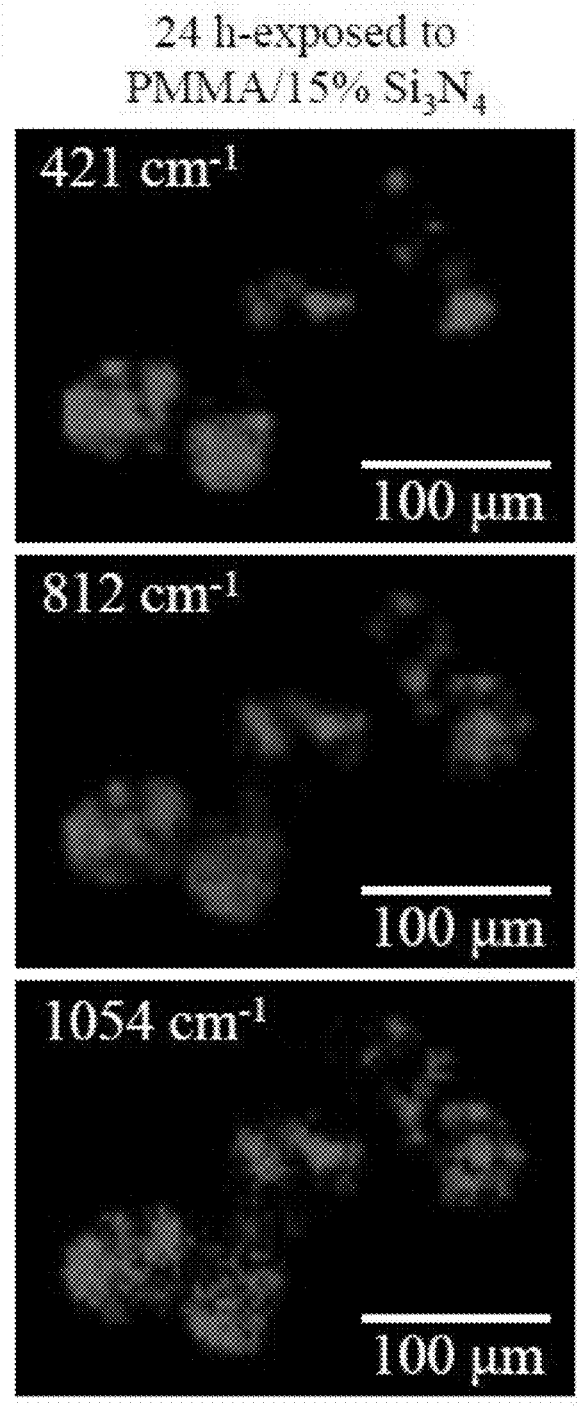
FIG. 13C      FIG. 13D

ANTIFUNGAL COMPOSITES AND METHODS THEREOF

CROSS-REFERENCE TO RELATED APPLICATIONS

This application claims priority to U.S. Provisional Application No. 62/965,451, filed Jan. 24, 2020 which is incorporated herein by reference in its entirety.

FIELD

The present disclosure relates to antifungal composites and methods. More specifically, the disclosure relates to silicon nitride composites, devices, and coatings for the prevention or treatment of fungal infections.

BACKGROUND

*Candida albicans* (*C. albicans*) is generally a harmless commensal organism in the microflora of the human intestines. However, when immune defenses weaken or during an imbalance of the gut microflora, its uncontrolled growth and transformation into a fungus can cause serious systemic infections. Dental prostheses are traditionally made of polymethylmethacrylate (PMMA, a thermally activated acrylic resin) because of its biocompatibility, excellent esthetics, and reparability. However, dental implants are reservoirs and incubators of oral infections, and PMMA provides a favorable environment for the colonization and proliferation of *C. albicans*. In fact, this fungus has its greatest affinity for the acrylic dentures and polymeric fillings.

Despite an increased incidence of *Candida*-related infections such as those caused by dental prostheses, there are few effective antifungal drugs, and drug resistance is increasing for these medications. Accordingly, there is a need for safe and reliable antifungal compositions that may be applied to or used as dental prostheses or other systems which may have prolonged contact with the human body to prevent or treat fungal infections.

SUMMARY

In accordance with an aspect of the disclosure, provided herein is an antifungal composite comprising: a biocompatible polymer; and a $Si_3N_4$ powder loaded in at least a portion of the biocompatible polymer, wherein the $Si_3N_4$ is present in a concentration sufficient to reduce or prevent a fungus from growing on the antifungal composite.

According to another aspect of the disclosure, also provided is a biocompatible device comprising the antifungal composite described herein.

Still also provided is a method of reducing or preventing the growth of a fungus on a biocompatible device comprising: placing the biocompatible device described herein in a patient; and contacting the biocompatible device with the fungus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B shows a micrograph of the state of proliferation of *C. albicans* after 24 hour exposure to PMMA. Inset depicts enlarged images of stained cells.
FIG. 2C shows a micrograph of the state of proliferation of *C. albicans* after 24 hour exposure to PMMA/$Si_3N_4$ substrates. Inset depicts enlarged images of stained cells.
FIG. 2D shows results from a *Candida* detector kit providing a visual indicator of the change in concentration (CFU/ml) for yeast cells exposed to pure PMMA (negative control), PMMA/15 wt. % $Si_3N_4$, and bulk $Si_3N_4$ (positive control).
FIG. 6A shows fluorescence images of yeast cells exposed for 24 hours to pure PMMA after staining with a nitrative stress sensing pyrromethene dye (green).
FIG. 6B shows fluorescence images of yeast cells exposed for 24 hours to PMMA/$Si_3N_4$ after staining with a nitrative stress sensing pyrromethene dye (green).

FIG. 12C shows results of in situ Raman mapping for the ergosterol band at 827 $cm^{-1}$ of yeast cells exposed to pure PMMA (upper), 15 wt. % $Si_3N_4$ in PMMA (middle), and 75 wt. % $Si_3N_4$ in PMMA (lower).

FIG. 12D shows results of in situ Raman mapping for the ergosterol band at 1096 $cm^{-1}$ of yeast cells exposed to pure PMMA (upper), 15 wt. % $Si_3N_4$ in PMMA (middle), and 75 wt. % $Si_3N_4$ in PMMA (lower).

FIG. 13C shows in situ maps of glycerol for yeast cells exposed to PMMA. Upper, middle, and lower images were taken at Raman frequencies of 421, 812, and 1054 $cm^{-1}$, respectively.

FIG. 13D shows in situ maps of glycerol for yeast cells exposed to PMMA/$Si_3N_4$. Upper, middle, and lower images were taken at Raman frequencies of 421, 812, and 1054 $cm^{-1}$, respectively.

DETAILED DESCRIPTION

Figure 1A:
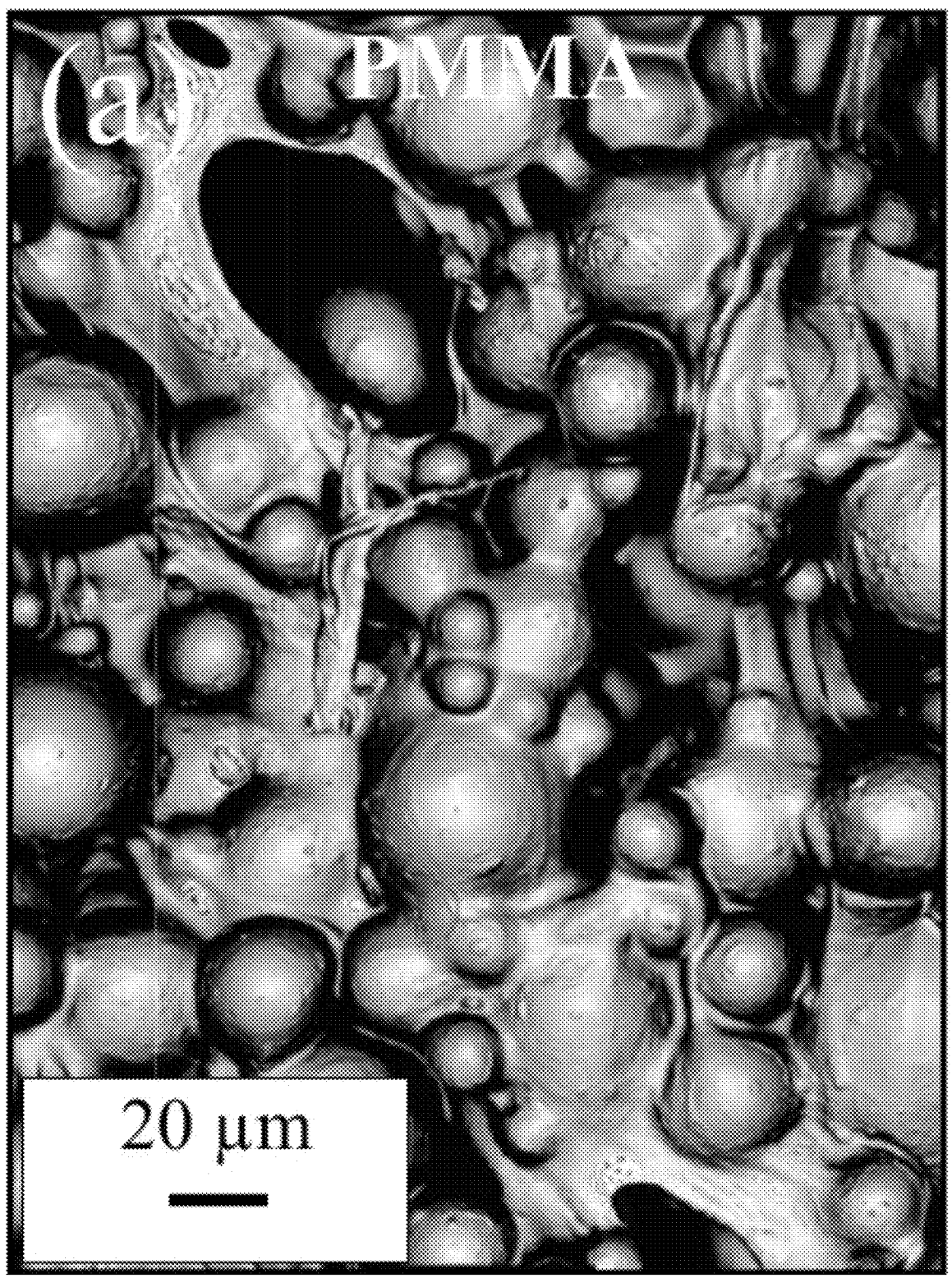
FIG. 1A shows a laser micrograph of a PMMA control.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof."

As used herein, the term "silicon nitride" includes $Si_3N_4$, β-$Si_3N_4$, α-$Si_3N_4$, SiYAlON, β-SiYAlON, SiYON, SiAlON, or combinations thereof.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms.

The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

The use of dentures, the need for prolonged therapies with antibiotics, and the increased longevity of the human population are three potential drivers of oral candidiasis. Pharmacological treatments of candidiasis are classified into topical drugs, which are applied to areas affected by superficial infections, and systemic drugs to treat more widespread infections. Both nystatin and azole-based drugs are effective for local treatments, but they have disadvantages; the former has an unpleasant taste and poor adherence to the oral mucosa while latter has possible negative interactions with other drugs, and it is absorbed by the intestine. An alternative prescription of miconazole has been introduced in the form of mucoadhesive buccal tablets. Its advantages are limited systemic absorption, higher salivary concentration, and better tolerance by patients. It reportedly has similar efficacy as gel applications. Systemic Candida infections are also treated with azole-based drugs, but this therapy is more complex, including the possibility that the treated strains are (or may become) resistant to the prescribed drugs.

Provided herein are antifungal composites, devices, and methods for the prevention or treatment of fungal infections using silicon nitride (as a dispersed minor fraction in a polymeric matrix). The candidacidal behavior of silicon nitride may overcome the emergence of azole resistant *Candida*. Replacing abiotic dentures, PMMA-based bone cements, and other dental prostheses with new long-lasting devices whose surfaces are functionalized by silicon nitride ($Si_3N_4$) may an important preventive tool that mimics the positive influence of organic nitrogen compounds on a variety of pathogens including *Candida* species. The candidacidal activity of $Si_3N_4$ described herein suggests a broad-spectrum approach in dentistry that is both safe to human cells and useful in combatting disease. With the increasing resistance of *Candida* species to drugs, the possibility of engineering biomaterial surfaces to intrinsically deliver candidacidal agents and regulate environmental pH may provide adaptive defenses similar to the immune system of the human body and reduce the need of chemoprophylaxis.

In an embodiment, the antifungal composite may include a biocompatible polymer and a $Si_3N_4$ powder loaded in at least a portion of the biocompatible polymer. The composite may then be used in turn to form biocompatible devices that may be exposed to fungal infections. Without being limited to any one theory, the $Si_3N_4$ in the polymer may create an environment inhospitable to a fungus. Therefore, polymers that may have been used in biocompatible devices, such as dental implants or devices, that previously allowed fungal infections to grow in a patient, may be functionalized with $Si_3N_4$ such that the device no longer allows or makes it more difficult for the fungal infection to grow on or near the device.

In some examples, the biocompatible polymer may be a thermoplastic polymer. The thermoplastic polymer may be acrylic, acrylic glass, or plexiglass. In some examples, the thermoplastic polymer is a poly(methyl methacrylate) (PMMA) resin.

In some examples, the fungus is yeast, such as *Candida albicans*. The antifungal composite may have increased candidacidal efficacy against the fungus as compared to the thermoplastic polymer alone. In some examples, the antifungal composites may mimic the positive influence of organic nitrogen compounds on a variety of fungal pathogens including *Candida* species. The antifungal composites may be both safe to human cells and useful in combatting disease. With the increasing resistance of *Candida* species to drugs, the use of antifungal composites to intrinsically deliver candidacidal agents and regulate environmental pH may provide adaptive defenses similar to the immune system of the human body and reduce the need of chemoprophylaxis.

Figure 14:
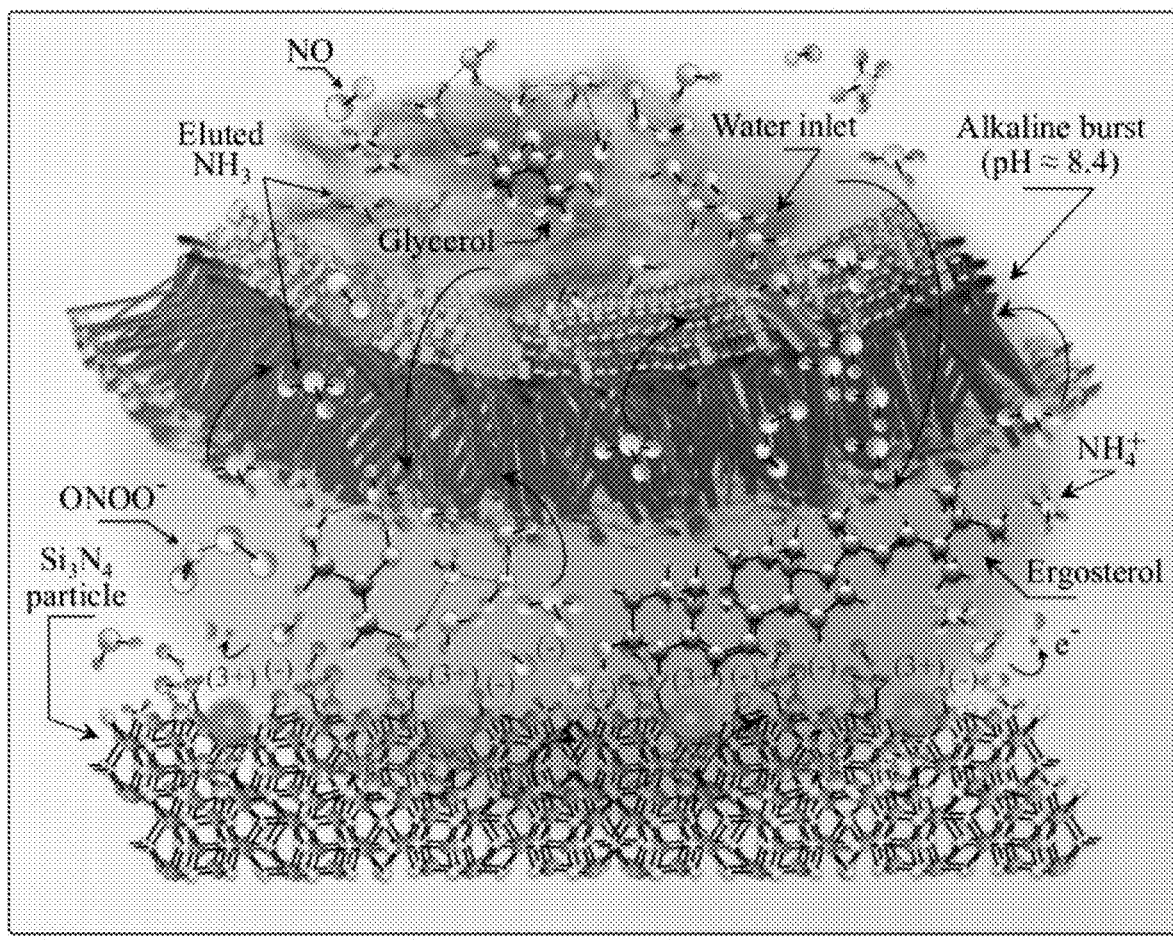
FIG. 14 is a schematic diagram illustrating the candidacidal activity of $Si_3N_4$ due to both RNS formation and the direct effect of $NH_3$ in the cytoplasmic space.

The presence of a fraction of $Si_3N_4$ in PMMA may induce both chemical and osmotic stresses in *C. albicans*. In at least one example, the antifungal composite subjects the fungus to nitrosative and osmotic stress. The chemically-mediated stresses occur when NO and other reactive nitrogen species (RNS) production exceed the compensatory capacity of the cells and culminate in the formation of nitrosylated end-products. Conversely, the presence of exogenous ammonia in the cytoplasmic space and the related pH enhancement results in increased osmotic stress. FIG. 14 provides a schematic diagram of the metabolic response of *C. albicans* to the chemical reactions taking place at the surface of $Si_3N_4$ due to both RNS formation and the direct effect of $NH_3$ in the cytoplasmic space. $NH_3$ freely penetrates the membrane inducing water inlet and unbalancing endocytotical pH toward alkaline values with the formation of $NH_4^+$. In response to an increase in osmotic water and related alteration of cell volume, the cell produces glycerol and expels glycerol water hydrates fulfilling the function of osmolyte. The yeast reacts with its typical metabolic pattern of resistance to oxidative and nitrosative stress by enhancing the production of ergosterol and glycerol in order to arrest the RNS attack and to detoxify ammonia, respectively. Concurrently, the cell "interprets" the high concentration of RNS at the $Si_3N_4$ interface as host's immune response and overexpresses ergosterol biosynthesis to increase virulence.

In some examples, the antifungal composite may create an alkaline pH when in an aqueous environment. The aqueous environment near the antifungal composite or at the surface of the antifungal composite may have a pH of about 8.4. The Si—N bonds of silicon nitrate undergo homolytic cleavage and nitrogen is instantaneously released into solution. Hydrogen cations are then scavenged from the surrounding environment. This results in an increase of pH to an equilibrium value of about 8.5 at the ceramic's surface. At physiological pH, 98 vol. % of the aqua ammonia is $NH_4^+$; however, at the very surface of $Si_3N_4$, the fraction of $NH_3$ can reach ~10 vol. % due to highly localized alkalinity. While $NH_4^+$ can only penetrate the cytoplasmic space through ion channels, the small and volatile $NH_3$ molecules freely pass through the lipid membrane. The presence $NH_3$ molecules in the endocytotic space may severely alter the osmotic balance of *C. albicans*. The cells may have a strong reaction to osmotic stress, which may be the direct result of $NH_3$ penetration.

Another important characteristic of $Si_3N_4$ in water is the formation of reactive nitrogen species (RNS), which occurs due to off-stoichiometric reactions involving oxygen radicals. The concurrent development of superoxide and ammonia moieties on exposed $Si_3N_4$ surfaces ultimately leads to NO and peroxynitrite ($OONO^-$) formation. Together with superoxides, NO is the chemical species used by macrophages to counteract pathogens. The strong oxidizing function of these compounds leads to the formation of $ONOO^-$. $ONOO^-$ in turn, strongly oxidizes proteins, lipids, and nucleic acids and is likely responsible for the candidacidal action. Macrophage candidacidal activity also likely involves NO, since inhibition of NO synthesis severely decreases resistance to candidiasis both in vitro and in vivo. From an off-stoichiometric chemistry viewpoint, $Si_3N_4$ exerts an action similar to that of macrophages on *C. albicans*. Inhibitors of NO synthesis and scavengers of either NO or $O_2.^-$ can reduce macrophage's candidacidal activity; it is the combination of NO and $O_2.^-$ radicals (and not either one individually) that induces the candidacidal effect exerted by macrophages. Further, the metabolic response of *C. albicans* to $Si_3N_4$ shows different patterns and represents candidacidal mechanisms dissimilar from those active in the case of bacteria and viruses.

In some examples, the $Si_3N_4$ material may be about 88 wt. % $Si_3N_4$, 2 wt. % $SiO_2$, 6 wt. % $Y_2O_3$, and 4 wt. % $Al_2O_3$. Upon firing, the combination of these elements may forms the $Si_3N_4$ crystal structure which is isostructural with β-Si-YAlON. The use of $Y_2O_3$ and $Al_2O_3$ also forms other crystalline phases including SiAlON, SiYON along with an intergranular glass comprised of Si, Y, Al, O, & N. In other instances, the $Si_3N_4$ material may be about 99 wt. % α-$Si_3N_4$. The $Si_3N_4$ may be present in a concentration sufficient to reduce or prevent the fungus from growing on the antifungal composite. The $Si_3N_4$ powder may be present within the thermoplastic polymer in a concentration of about 1 vol. % to about 30 vol. %. In an example, $Si_3N_4$ powder may be present within the thermoplastic polymer in a concentration of about 1 vol. %. In an example, $Si_3N_4$ powder may be present within the thermoplastic polymer in a concentration of about 5 vol. %. In an example, $Si_3N_4$ powder may be present within the thermoplastic polymer in a concentration of about 10 vol. %. In an example, $Si_3N_4$ powder may be present within the thermoplastic polymer in a concentration of about 15 vol. %. In an example, $Si_3N_4$ powder may be present within the thermoplastic polymer in a concentration of about 20 vol. %. In an example, $Si_3N_4$ powder may be present within the thermoplastic polymer in a concentration of about 25 vol. %. In an example, $Si_3N_4$ powder may be present within the thermoplastic polymer in a concentration of about 30 vol. %.

In some examples, the $Si_3N_4$ powder may be loaded in the polymer by being mixed homogenously throughout the polymer. In at least one example, the $Si_3N_4$ powder may be loaded in a thermoplastic powder and mixed homogenously throughout the thermoplastic polymer. Then, the polymer shape or composition may be formed. In other examples, the $Si_3N_4$ powder is mixed in a surface layer of the thermoplastic polymer. In some examples, a surface layer may be formed by creating one mixture having silicon nitride and the polymer and a second mixture of the polymer alone. Then in combining the two mixtures, the first mixture containing the $Si_3N_4$ is applied to the outside of the pure polymer mixture. In another example, the polymer shape is first prepared and then an adherent slurry coating of $Si_3N_4$ may be applied to the exterior surface. The coating may be bonded to the polymer by chemical means or it may be embedded into the surface of the polymer using laser energy.

The antifungal composites may be used to form biocompatible devices to be implanted or used in a patient. Because dental devices are the most prone to *C. albicans* infection, the antifungal composites may be used in dental devices such as abiotic dentures, cements, temporary or permanent implants, fillings, subgingival bone bonding devices, and other dental prostheses. These devices may be monolithic devices made of the biocompatible polymer with the $Si_3N_4$ powder mixed homogenously throughout or may have surfaces that are functionalized by $Si_3N_4$.

Also provided herein is a method of reducing or preventing a fungus from growing on a biocompatible device. The method may include placing the biocompatible device containing the antifungal composite in a patient and contacting the biocompatible device with the fungus.

The fungus may be yeast, such as *Candida albicans*. The antifungal composite may have increased candidacidal efficacy against the fungus as compared to the thermoplastic polymer alone. In some examples, the antifungal composite subjects the fungus to nitrosative and osmotic stress. In additional examples, the antifungal composite creates an alkaline pH, for example about 8.4, when in an aqueous environment.

EXAMPLES

Example 1: Effect of Silicon Nitride on *Candida albicans* Cell Viability and Proliferation To show the effect of silicon nitride ($Si_3N_4$) on fungal cell viability and proliferation, two sets of 15×3 mm (n=4 each) substrates were prepared from commercially available polymethyl methacrylate substrate (PMMA) resin used to fabricate orthodontic appliances. The PMMA consisted of a white powder (PMMA 20~30%, copolymer of methacrylate 70~80%, benzoyl peroxide 0.1~1.0%) and a pink polymer (methyl methacrylate>95%, N,N-Dimethyl-P-Toluidine<2%, ethylene glycol dimethacrylate<3%). One set of four substrates was prepared by mixing the PMMA resin with 15 wt. % $Si_3N_4$ powder with an average grain size of about ~1 µm. No residual α-$Si_3N_4$ phase was present in the powder. For comparison, a second set of four PMMA substrates was also prepared. They contained 75 wt. % of the same $Si_3N_4$ powder. However, these samples were only used to confirm chemical interactions between the substrates and pathogen. These samples have low applicative relevance given their poor structural properties. Loading PMMA with $Si_3N_4$ powder above the percolation limit creates agglomeration and significantly affects mechanical properties. The surface roughness of the two experimental groups of samples was measured with a laser microscope coupled to 3-D imaging analysis software. Their surface morphologies were examined using a scanning electron microscope. A photoelectron spectrometer operating with an x-ray source of monochromatic $MgK_\alpha$ (output 10 kV, 10 mA) was employed for spectroscopic (XPS) analyses of bulk $Si_3N_4$ substrates. The surfaces of the $Si_3N_4$ samples were analyzed after exposure to an aqueous environment as a function of time and pH. Before characterization, an Ar+ sputtering procedure was applied to clean the samples. Measurements were conducted in the vacuum chamber at $\sim2\times10^{-7}$ Pa with an analyzer pass energy of 10 eV and voltage step size of 0.1 eV. X-ray incidence and takeoff angles were set at 34° and 90°, respectively. Spectra were averaged over ten separate measurements (n=10) per sample.

Figure 1B:
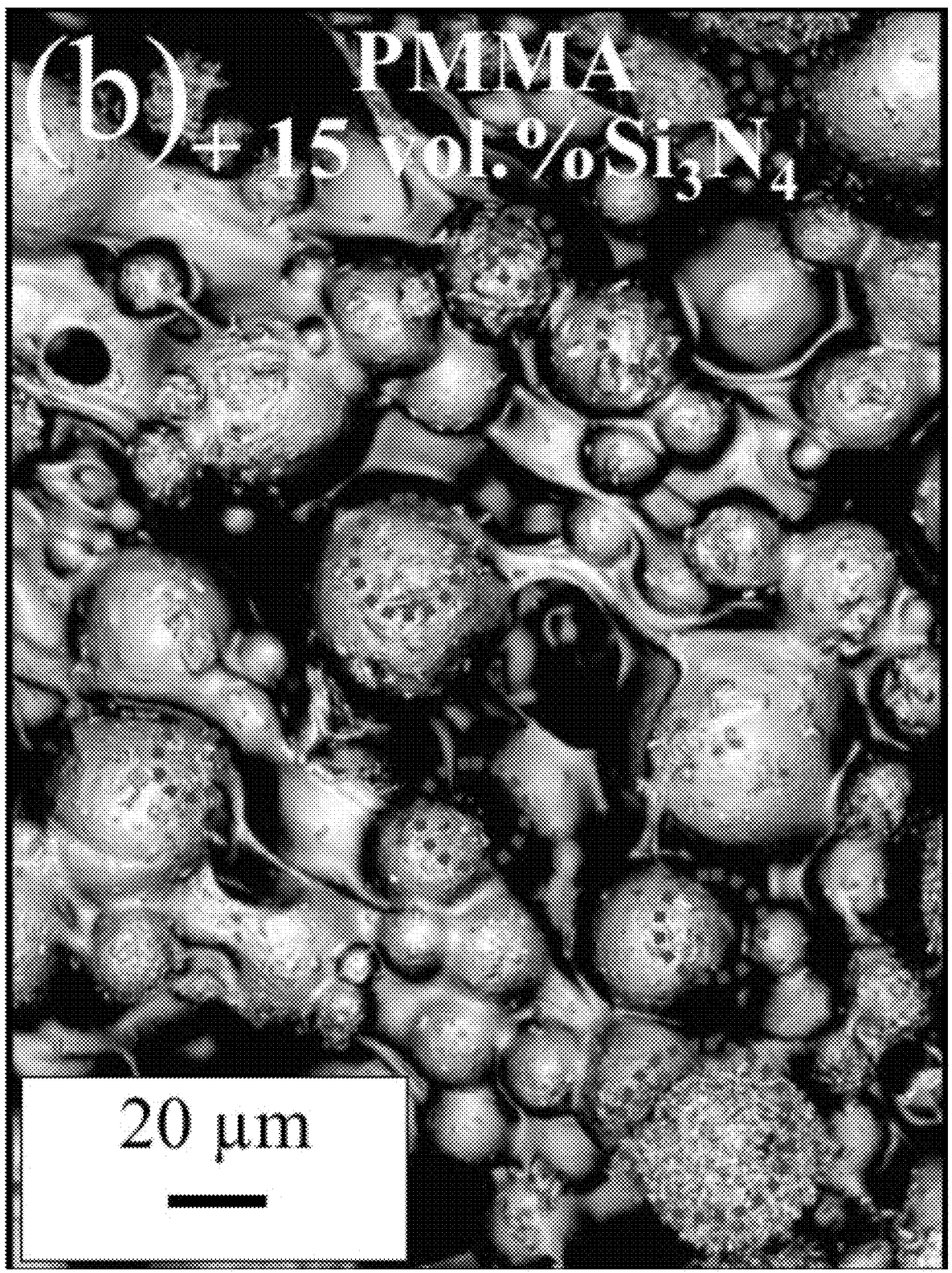
FIG. 1B shows a laser micrograph of PMMA/$Si_3N_4$ substrates. Circles locate $Si_3N_4$ particles.
Figure 1C:
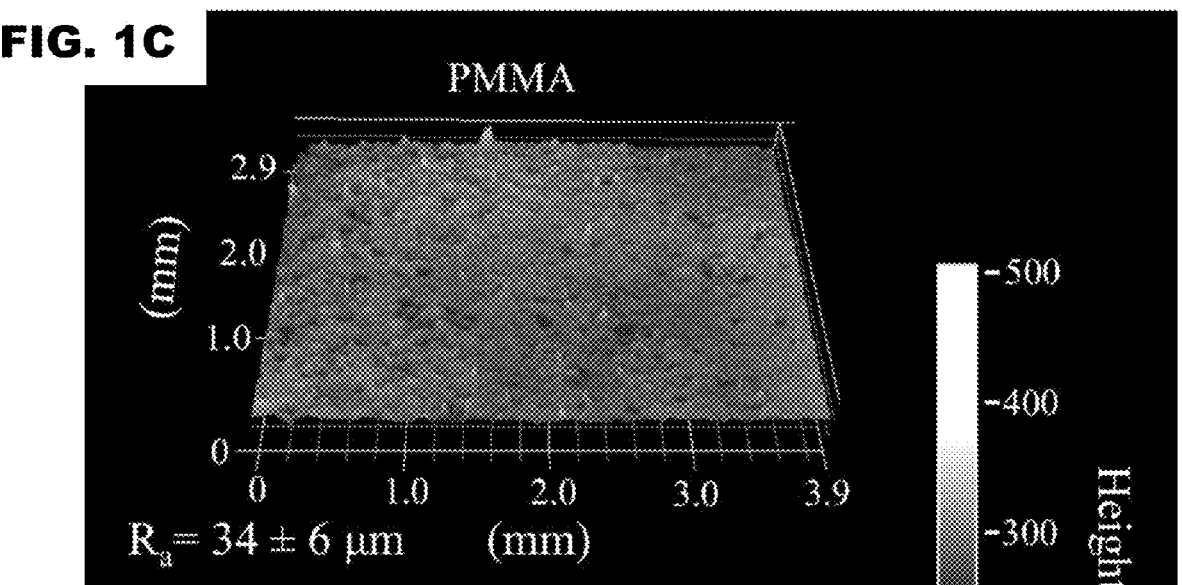
FIG. 1C shows results of topographic characterizations of the PMMA control.
Figure 1D:
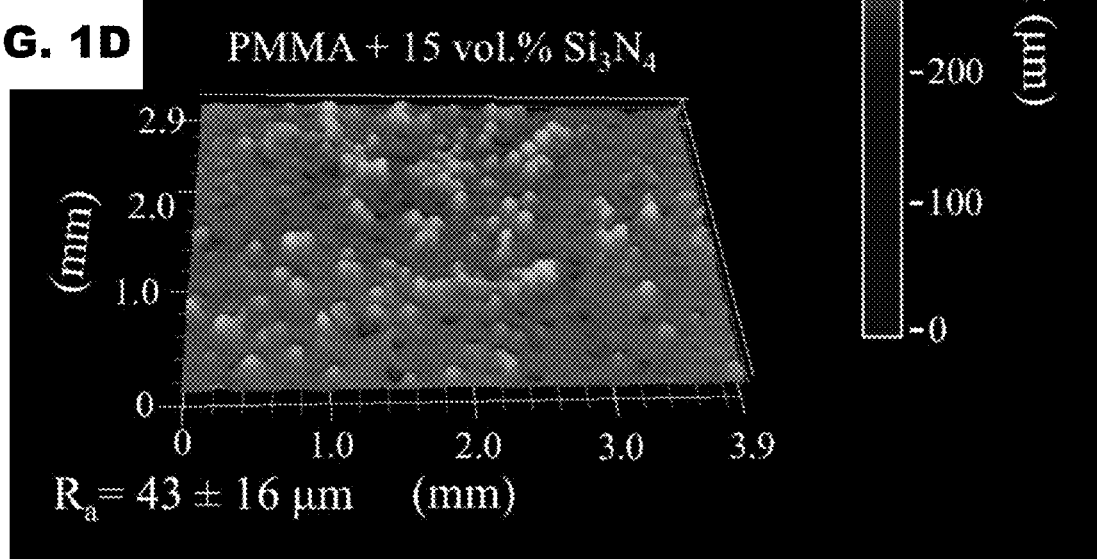
FIG. 1D shows results of topographic characterizations of the PMMA/$Si_3N_4$ substrates.
Figure 2A:
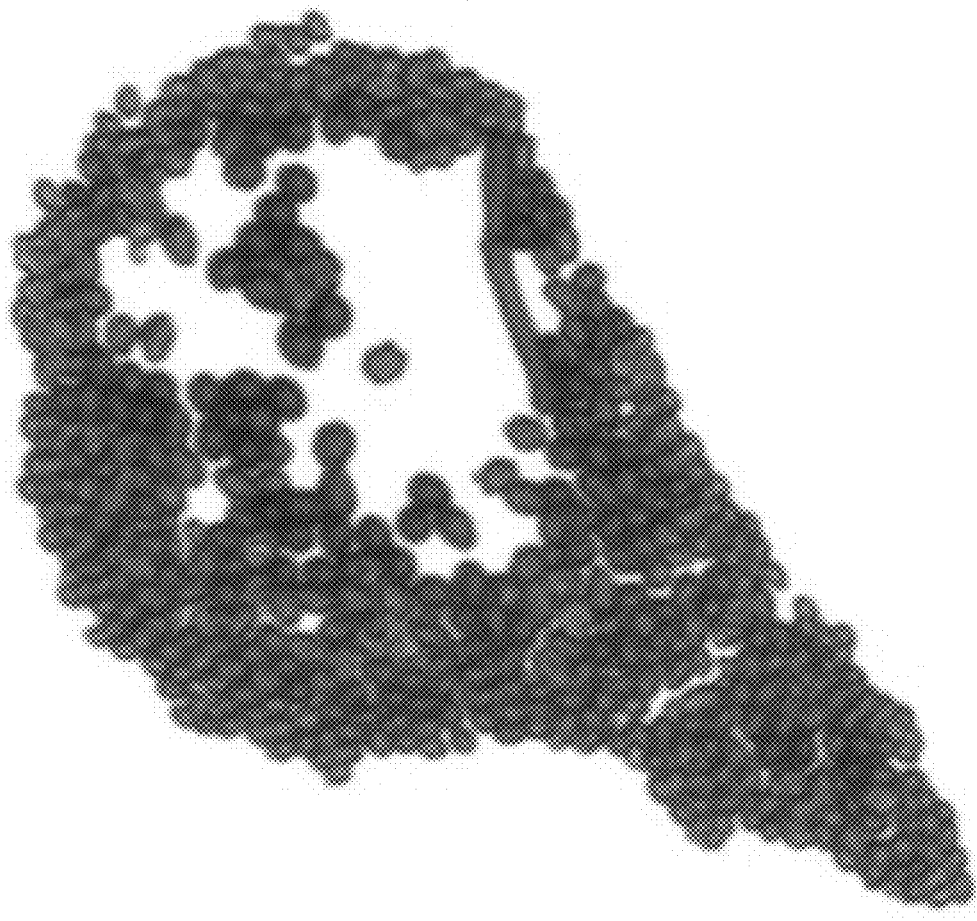
FIG. 2A shows a micrograph after violet staining of as-cultured *C. albicans*.

FIGS. 1A and 1B show SEM micrographs of the surfaces of PMMA control and PMMA/Si$_3$N$_4$ substrates, respectively. Similar morphologies were observed for both substrates but the presence of protruding Si$_3$N$_4$ grains was evident on the surface of the latter samples (cf circled areas in FIG. 1B). Using laser microscopy, topographic characterization of PMMA surfaces without and with embedded Si$_3$N$_4$ grains are shown in FIGS. 1C and 1D, respectively. The surfaces of both substrates were morphologically similar with the mean roughness of the PMMA/Si$_3$N$_4$ substrate being ~26% greater than that of the pure PMMA sample (i.e., 43±16 μm vs. 34±6 μm).

The *C. albicans* cells were counted and assessed using fluorescence microscopy. Cells exposed for 24 hours to PMMA and PMMA/Si$_3$N$_4$ substrates were stained for observations by fluorescence microscopy using DAPI (blue; targeting nuclei) and the specific fluorescent stain kit for fungi Fungiflora Y® (green; targeting fungal cell wall chitin, glucans, and polysaccharides). After exposure, the cells were fixed with 95% ethanol, washed with distilled water, and stained with Fungiflora Y® and DAPI for 5 minutes. After washing in water, cell counts were performed using a fluorescence microscope. The *Candida* detector kit is a selective medium for *Candida* species that was developed for clinical use. It consists of a Sabouraud culture-based medium with bacterial growth depressants so that only the *Candida* species will thrive. *C. albicans* yeast cells were incubated for 24 hours on PMMA (negative control), PMMA/15 wt. % Si$_3$N$_4$, and bulk Si$_3$N$_4$ (positive control) substrates, respectively. After washing the cells in PBS, they were pipetted from the fluid and introduced into the kit medium. The cells were cultured at room temperature for 48 hours. A graded change in color from red to yellow of the medium was then matched to a scale provided by the kit maker and converted into yeast cell concentration. This test was conceived as a simple and relatively quick way to assess oral hygiene. Its visualization and high precision were used as a straightforward measure of the candidacidal properties of Si$_3$N$_4$ and its composites.

For observation by confocal laser microscopy (CLM), *C. albicans* cells exposed to PMMA and PMMA/Si$_3$N$_4$ substrates were examined using a specific fluorescent kit for cholesterol. The cells were fixed with 4% paraformaldehyde, washed with PBS, stained, and observed using the CLM with an excitation set at 338 nm and emission at 480 nm.

In a separate test, *C. albicans* cells exposed to PMMA and PMMA/Si$_3$N$_4$ substrates were washed with PBS and examined with a specific fluorescent stain using a nitrative stress sensing dye (NiSPY-3 green). Observations were made immediately after staining. Fluorescence micrographs were acquired with a stimulated emission depletion microscope operating in standard laser scanning confocal mode. This procedure was based on a series of experiments along with published data for the NiSPY-3 nitrative sensing dye. These studies demonstrated that NiSPY-3 is highly reactive toward ONOO$^-$ in an aqueous medium and shows little fluorescence upon the addition of ROS, (e.g., .OH, HOCl, $^1$O$_2$, NO, O$_2$.$^-$ and H$_2$O$_2$), whereas strong fluorescence is observed by reacting with ONOO$^-$. NiSPY-3 is also applicable for live-cell imaging of ONOO$^-$ with no apparent cell toxicity.

The Periodic Acid Schiff (PAS) staining method was also utilized. In this test, the cells were fixed with 95% ethanol, washed with distilled water, and incubated with 0.5% Periodic Acid Solution for 10 minutes. Staining with Schiff's Reagent solution was then performed for 15 minutes. After washing, the cells were observed under a digital microscope VHX-2000.

Figure 3A:
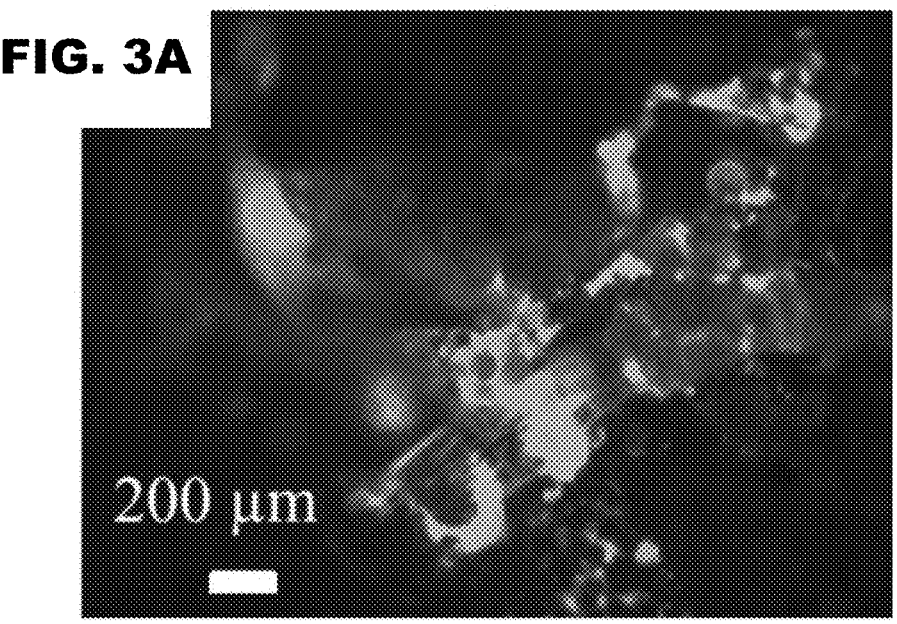
FIG. 3A shows fluorescence images of *C. albicans* exposed for 24 hours to PMMA control substrate with beta-linked polysaccharides of the fungal cell walls green stained.
Figure 3B:
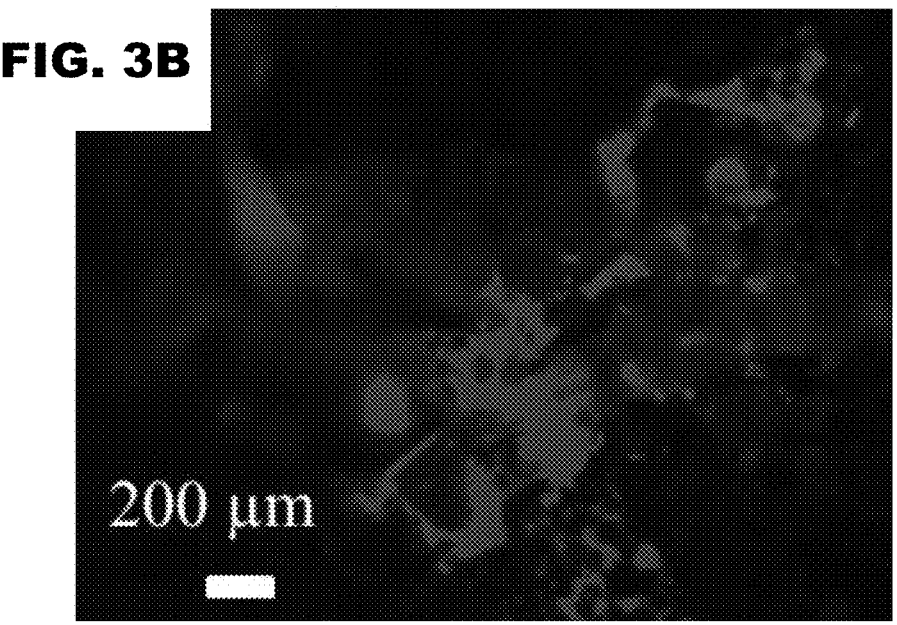
FIG. 3B shows fluorescence images of *C. albicans* exposed for 24 hours to PMMA control substrate with adenine-thymine-rich regions of DNA blue-stained.
Figure 3C:
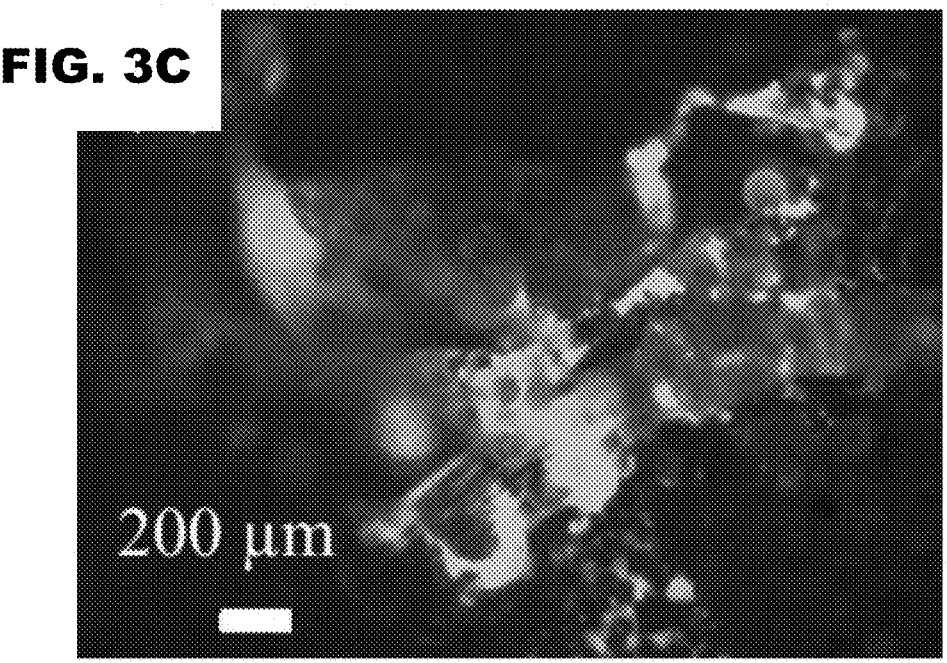
FIG. 3C is an overlapping image of FIG. 3A and FIG. 3B.
Figure 3D:
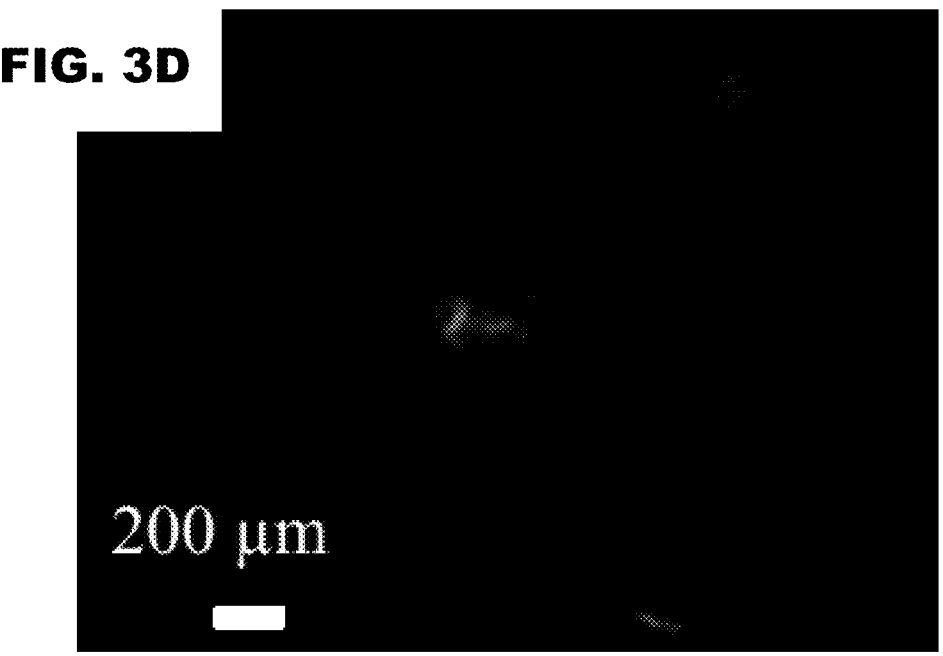
FIG. 3D shows fluorescence images of *C. albicans* exposed for 24 hours to PMMA/$Si_3N_4$ substrate with beta-linked polysaccharides of the fungal cell walls green stained.
Figure 3E:
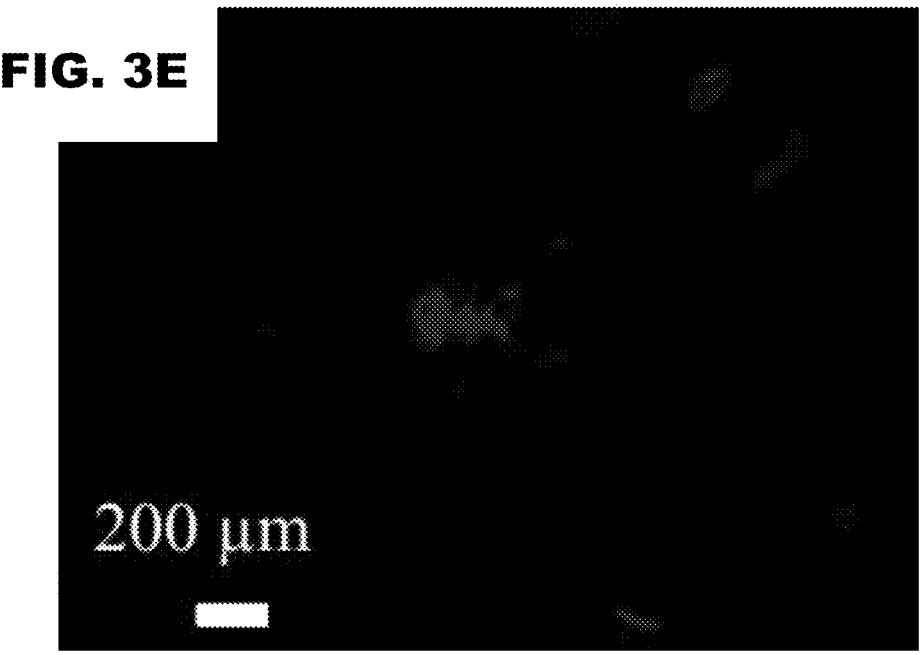
FIG. 3E shows fluorescence images of *C. albicans* exposed for 24 h to PMMA/$Si_3N_4$ substrate with adenine-thymine-rich regions of DNA blue-stained.
Figure 3F:
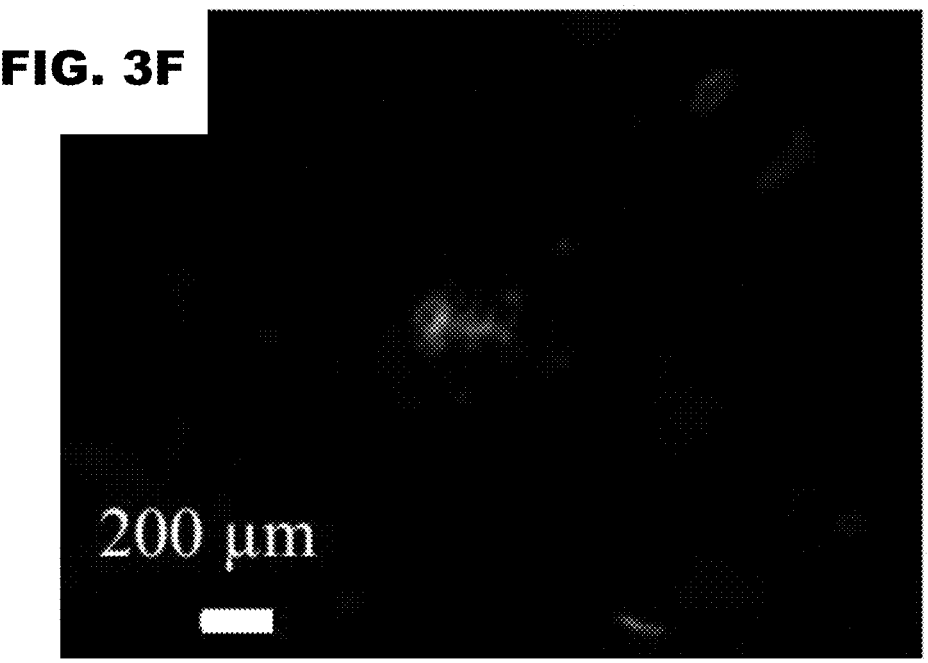
FIG. 3F is an overlapping image of FIG. 3D and FIG. 3E.

Representative images for cell/CFU counting and fluorescence microscopy assessments are shown FIGS. 2A-2C and 3A-3F, respectively. The micrographs in FIGS. 2A-2C were obtained after violet staining. They showed the as-cultured *C. albicans* cells (FIG. 2A), and their state of proliferation after 24 hours exposure to PMMA and PMMA/ 15 wt. % Si$_3$N$_4$ substrates (in FIGS. 2B and 2C, respectively). Enlarged images of stained cells are given in the insets in FIGS. 2B and 2C. In FIG. 2D the *Candida* detector kit provides a visual indicator of the change in concentration (CFU/ml) for yeast cells exposed to pure PMMA (negative control), PMMA/15 wt. % Si$_3$N$_4$, and bulk Si$_3$N$_4$ (positive control). The results of this assay, in which the preservation of the red color indicates no proliferation of yeast cells, provides vivid and unequivocal confirmation of the candidacidal effectiveness of Si$_3$N$_4$ both as dispersoids embedded into PMMA and as a bulk substrate. The fluorescence images in FIGS. 3A, 3B, and 3C represent beta-linked polysaccharides of the fungal cell walls (i.e., green stained glucan and chitin), adenine-thymine-rich regions of DNA (i.e., blue-stained nuclei), and their overlapping image, respectively, for *C. albicans* exposed to the PMMA substrate for 24 hours. The fluorescence micrographs in FIGS. 3D, 3E, and 3F represent similar features for yeast cells exposed to the PMMA/Si$_3$N$_4$ substrate for 24 hours.

Figure 4A:
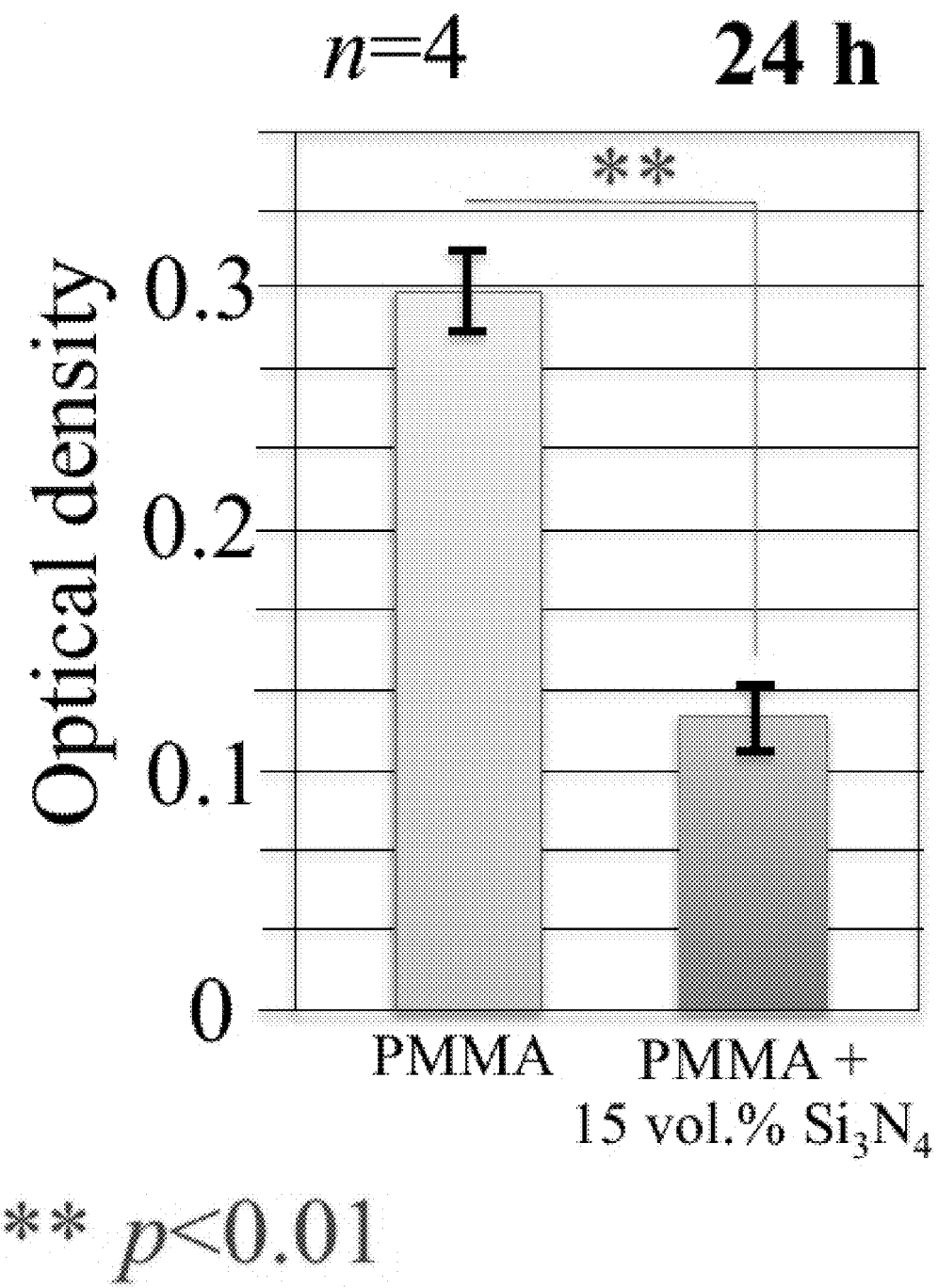
FIG. 4A shows the results of yeast cell proliferation by optical density according to microbial viability assay.
Figure 4B:
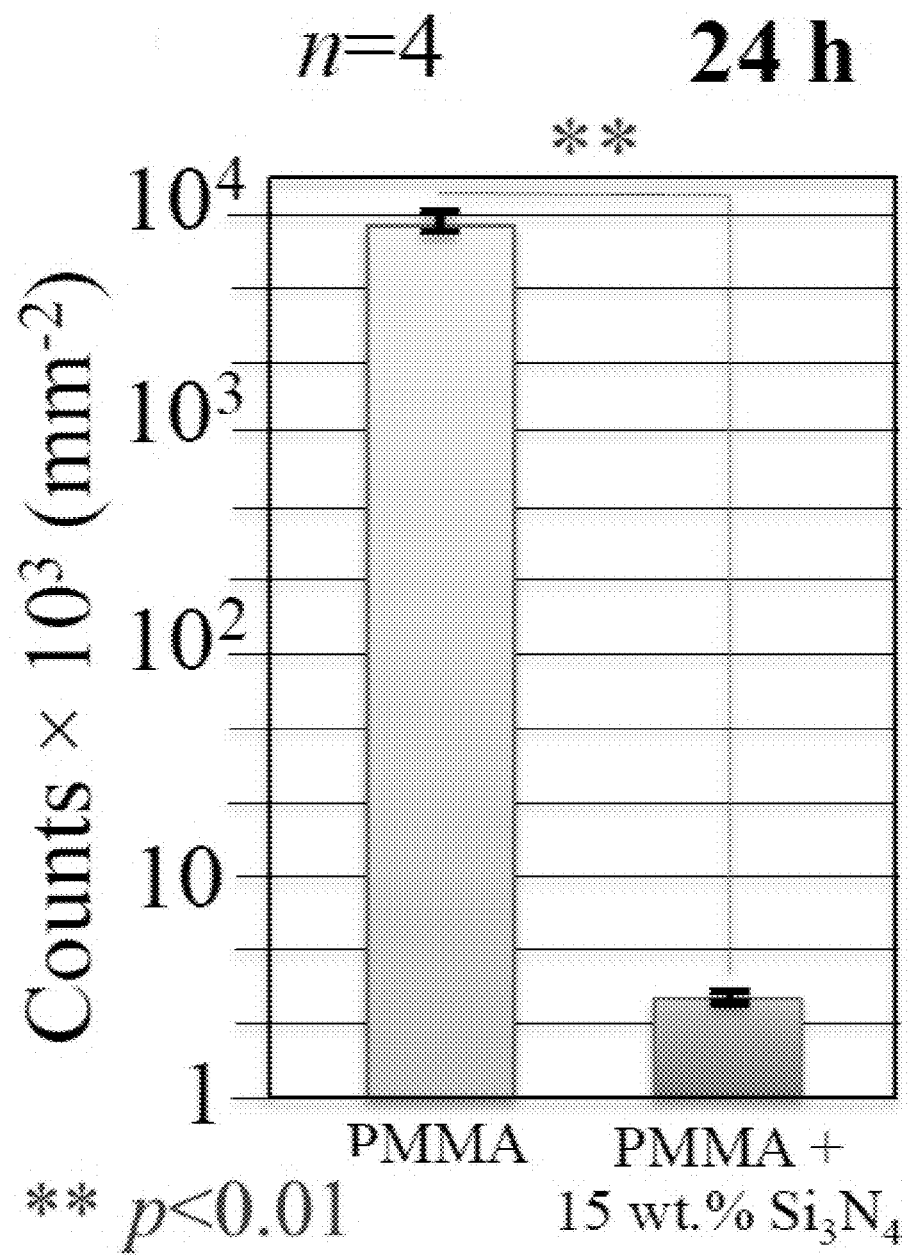
FIG. 4B shows the results of yeast cell proliferation by direct cell counting on violet stained cells.
Figure 4C:
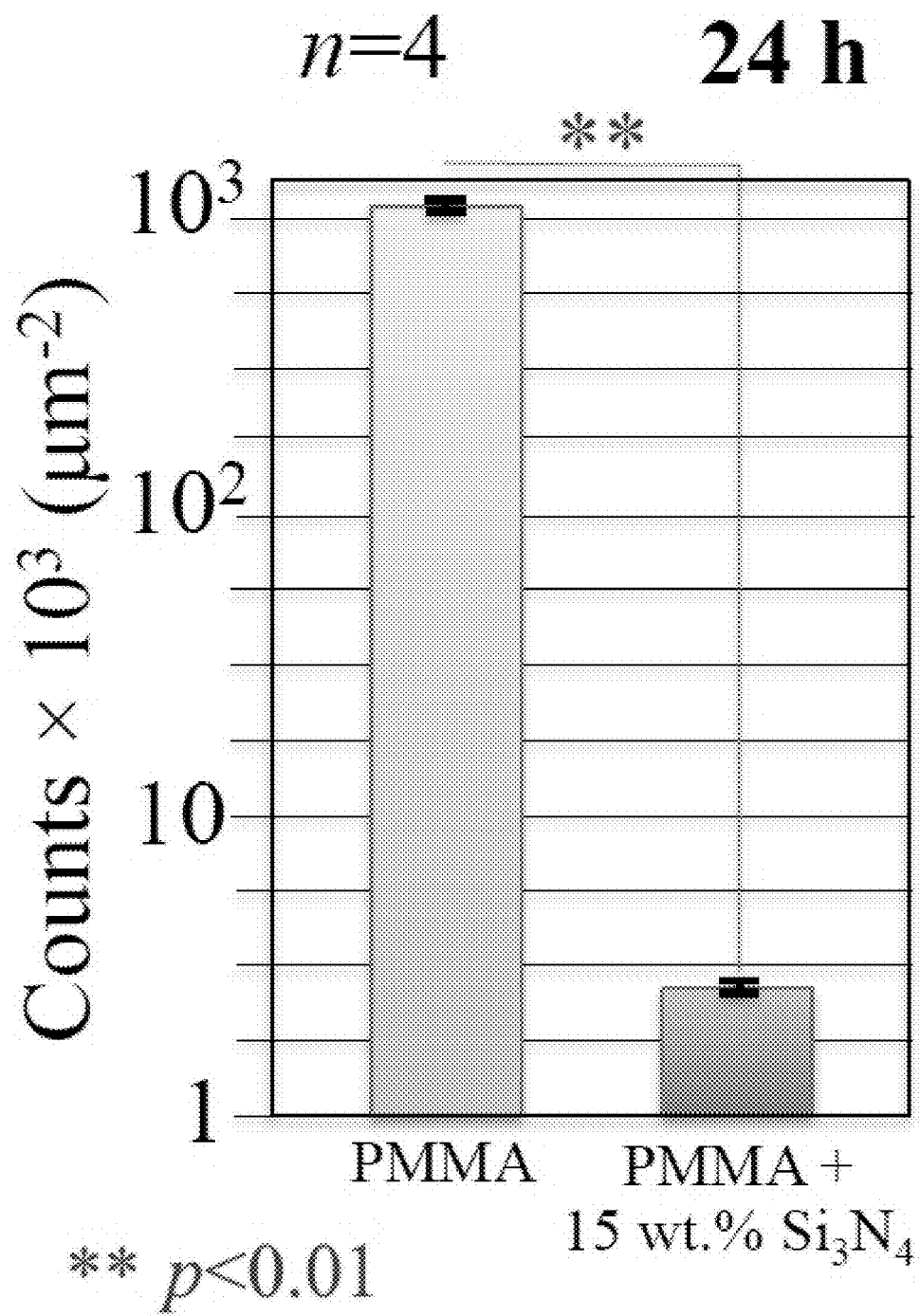
FIG. 4C shows the results of yeast cell proliferation by green pixel counting on fluorescence micrographs.

The results for cell proliferation on pure PMMA and PMMA/Si$_3$N$_4$ substrates are summarized in FIG. 4A using optical density values from a microbial viability assay, FIG. 4B using direct cell counting of violet stained cells (i.e., for a total of 20 micrographs such including those in FIGS. 2A-2C), and FIG. 4C using green pixel counting on fluorescence micrographs (i.e., for 20 micrographs including those in FIGS. 3A-3F. Statistically significant differences demonstrating the candidacidal efficacy of the PMMA/ Si$_3$N$_4$ composite was observed for each method (n=4, p<0.01). Of note, the direct cell counting method showed a ~4-log$_{10}$ reduction in pathogen viability (99.99%).

Figure 5A:
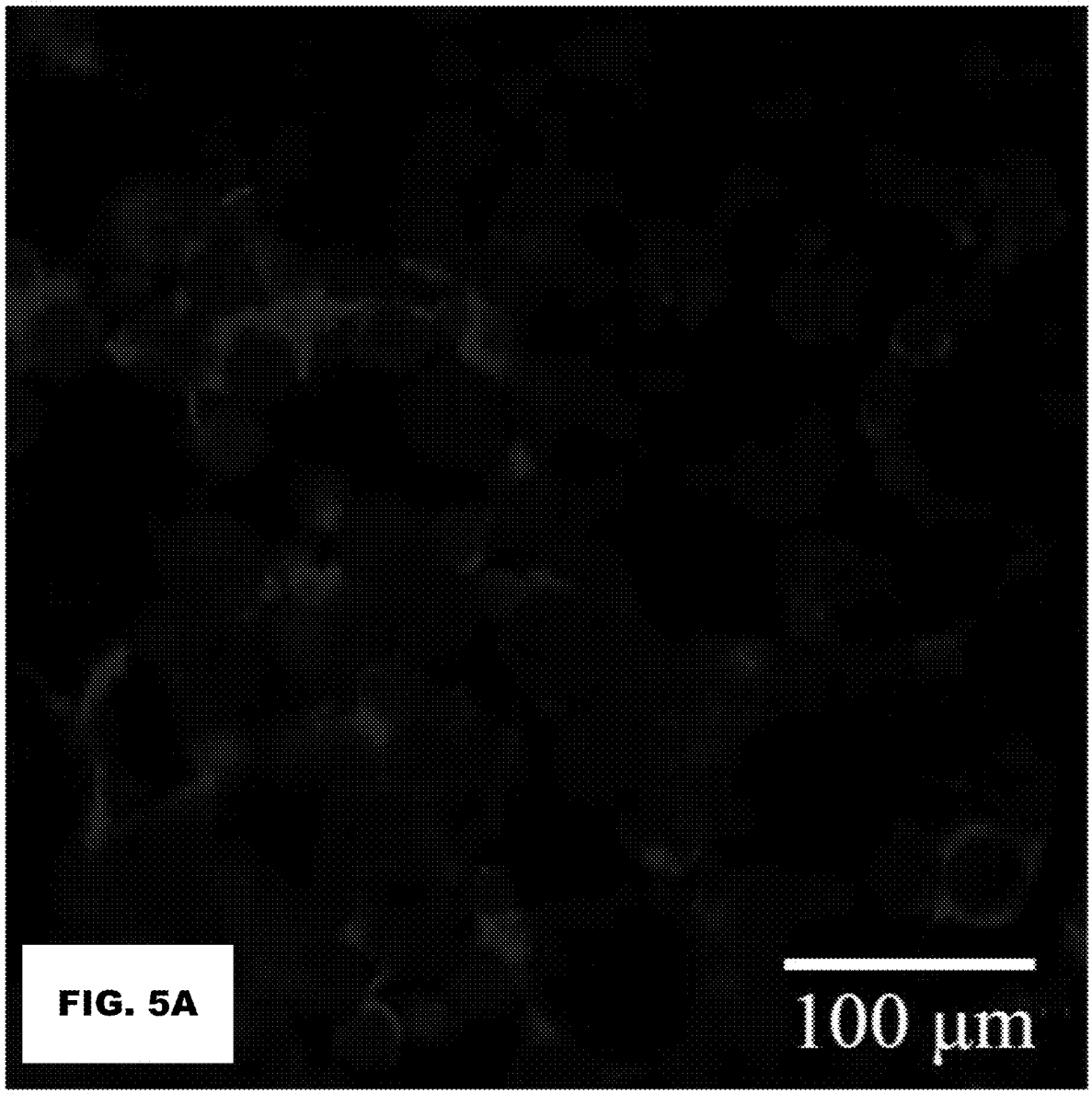
FIG. 5A shows confocal laser microscopy results on yeast cells exposed for 24 h PMMA and treated with fluorescent (blue) stain specific to ergosterol.
Figure 5B:
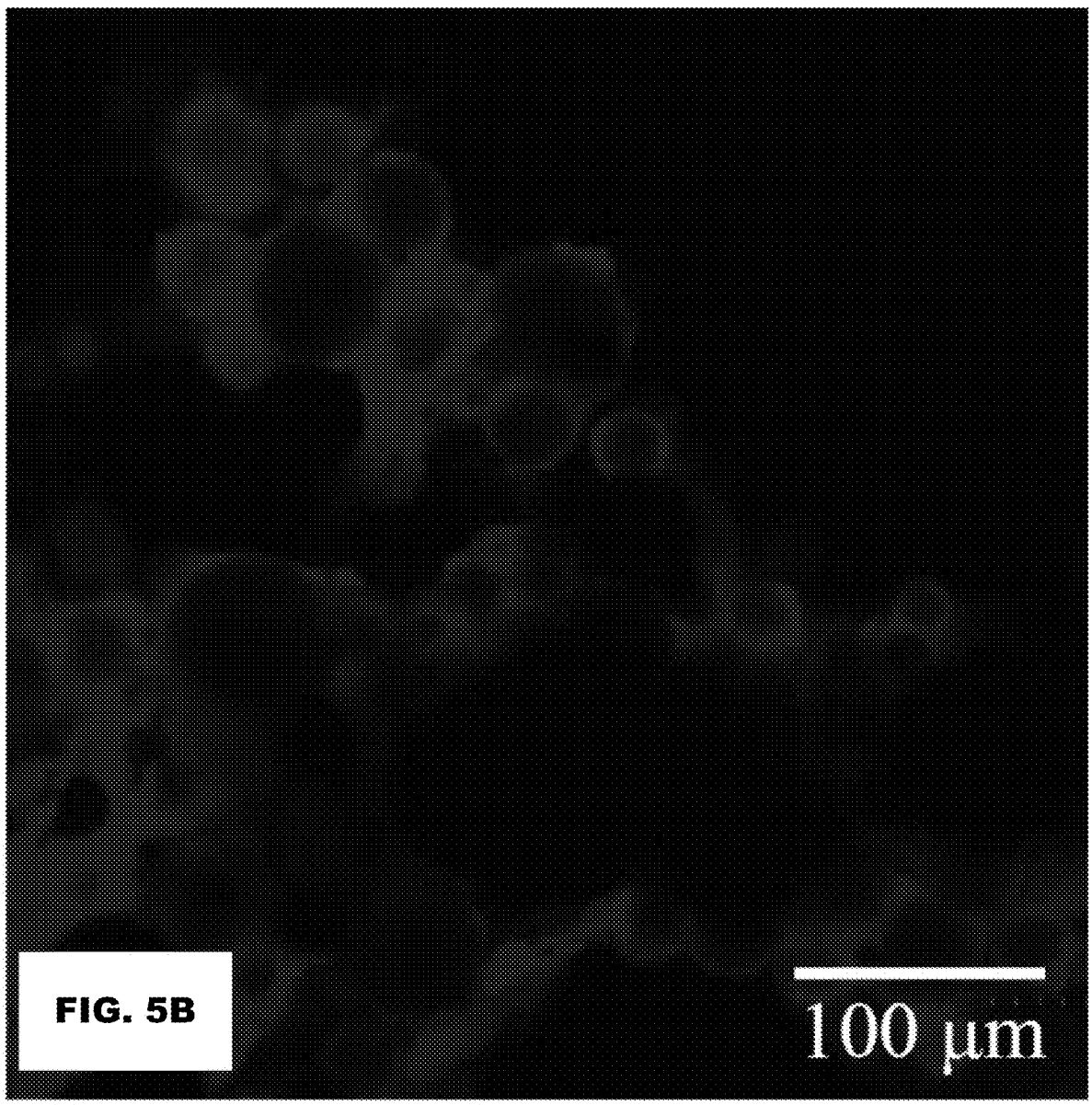
FIG. 5B shows confocal laser microscopy results on yeast cells exposed for PMMA/$Si_3N_4$ substrates treated with fluorescent (blue) stain specific to ergosterol

FIGS. 5A-5B shows confocal laser microscopy results on yeast cells exposed for 24 hours to (a) PMMA and (b) PMMA/Si$_3$N$_4$ substrates treated with fluorescent (blue) stain specific to ergosterol. The comparison shows a clear enhancement of ergosterol content in *C. albicans* when exposed to PMMA containing Si$_3$N$_4$. Ergosterol, which is an important plasma membrane lipid in the *Candida* species, regulates its fluidity, permeability, and integrity. Its enrichment has been associated with the susceptibility of *C. albicans* cells to a variety of stresses, such as ionic, osmotic, oxidative pressures, and treatment by antifungal drugs. Recently, the ease with which *Candida* species acquired resistance to commonly used antifungal azole compounds, which induce a reduction in ergosterol biosynthesis, has been related to mutation in the transcription factors responsible for ergosterol pathways.

Figure 6C:
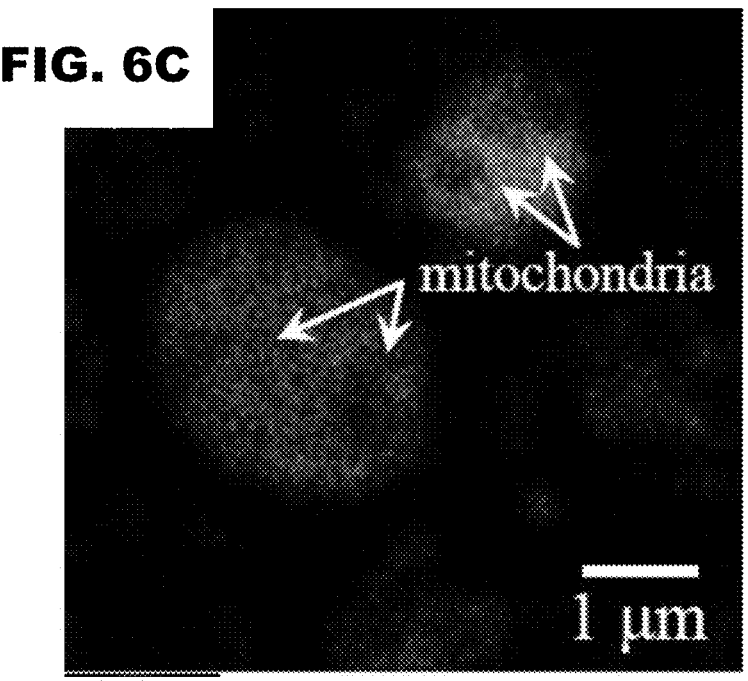
FIG. 6C is an enlarged inset of the fluorescent image shown in FIG. 6A.
Figure 6D:
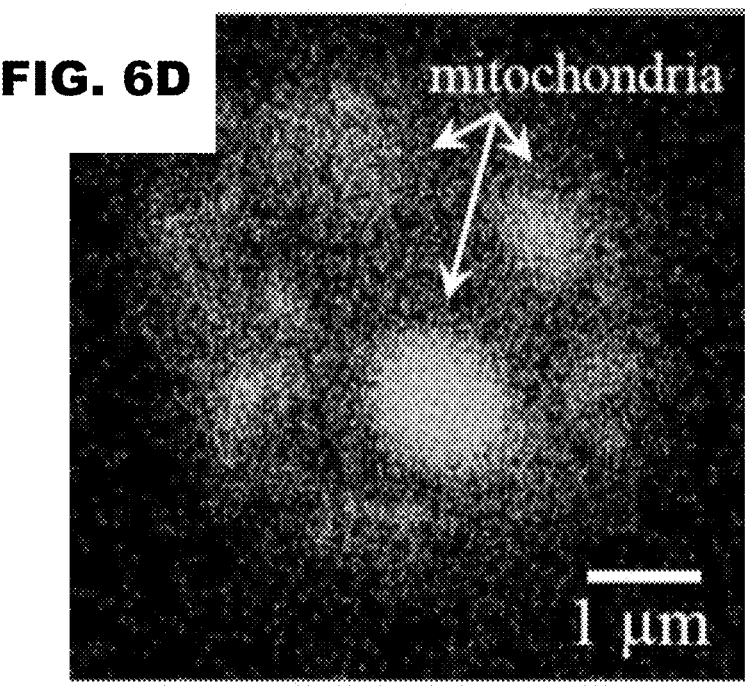
FIG. 6D is an enlarged inset of the fluorescent image shown in FIG. 6B.

FIGS. 6A-6B shows the results of single-cell observation on the PMMA/Si$_3$N$_4$ composite after staining with a nitrative stress sensing pyrromethene dye (green). This staining not only reveals the presence of ONOO$^-$ but also clarifies its location within the yeast's endocytotic space. Fluorescence images of yeast cells exposed for 24 hours to pure PMMA and PMMA/Si$_3$N$_4$ are shown in FIG. 6A and FIG. 6B, respectively. The presence of Si$_3$N$_4$ appeared to increase the average size of the yeast cells by roughly a factor two (cf. FIGS. 6A and 6B). This comparison, which was verified over ~1600 μm$^2$ area for each sample type, suggests: (i) the green fluorescence was enriched in the yeast exposed to PMMA/Si$_3$N$_4$ when compared to pure PMMA; and, (ii) the fluorescent signal appeared enhanced in areas with roundish morphology—resembling a mitochondrion in these cells. Conversely, green pixels were conspicuously absent in areas with similar morphology for samples exposed only to pure PMMA. These differences are identified by arrows, and in the enlarged insets of FIG. 6A and FIG. 6B which are shown in FIG. 6C and FIG. 6D, respectively. This evidence supports the hypothesis that highly reactive ONOO⁻ nitrogen radicals formed in the presence of $Si_3N_4$ and accumulated in the yeast mitochondria.

Example 2: Effect of Silicon Nitride on pH in Aqueous Solution

To investigate the chemical reactions of silicon nitride in aqueous solutions, the pH of an aqueous suspension containing 15 wt. % of the same $Si_3N_4$ powder used to fabricate the PMMA/$Si_3N_4$ composite was measured by an overhead pH meter at room temperature as a function of time for up to 400 seconds at intervals of 10 seconds.

The chemistry of $Si_3N_4$ in aqueous solution is dominated by the dissociation of Si—N covalent bonds at its surface. In water, this results in the formation of aqua ammonia and silicon dioxide (silica) according to the following equations:

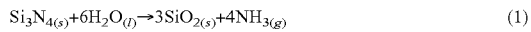
$$Si_3N_{4(s)} + 6H_2O_{(l)} \rightarrow 3SiO_{2(s)} + 4NH_{3(g)} \quad (1)$$

$$NH_{3(g)} + H^+ \rightarrow NH_4^+{}_{(aq)} \quad (2)$$

$$SiO_{2(s)} + 2H_2O_{(l)} \rightarrow Si(OH)_{4(aq)} \quad (3)$$

where the subscripts (s), (g) and (aq) refer to solid, gaseous, and aqueous states, respectively. Eluted nitrogen promptly scavenges protons from the aqueous environment (cf. Eqs. (1) and (2)) and a robust pH buffering effect is quickly established in the vicinity of the $Si_3N_4$'s surface by the formation of gaseous ammonia $NH_3$ and ammonium ions ($NH_4^+$). Silica further reacts to form silicic acid $Si(OH)_4$ according to Eq. (3). Unlike $NH_3$, which is volatile, $Si(OH)_4$ and $NH_4^+$ remain in the aqueous solution.

Figure 7A:
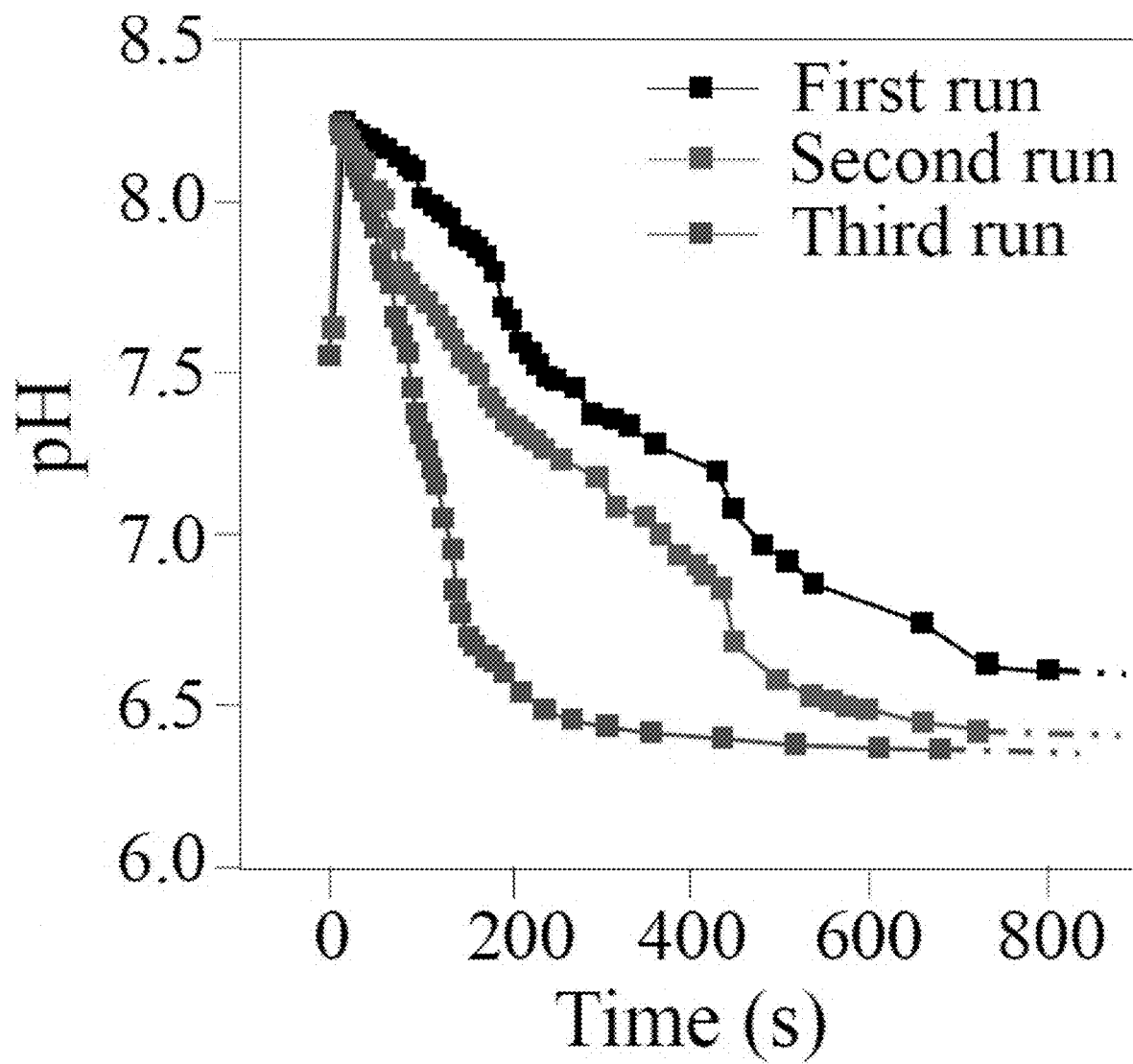
FIG. 7A is a graph depicting time-dependence of the pH of 15 wt. % $Si_3N_4$ powder added to demineralized water in an open system. Results from three runs are shown.
Figure 7B:
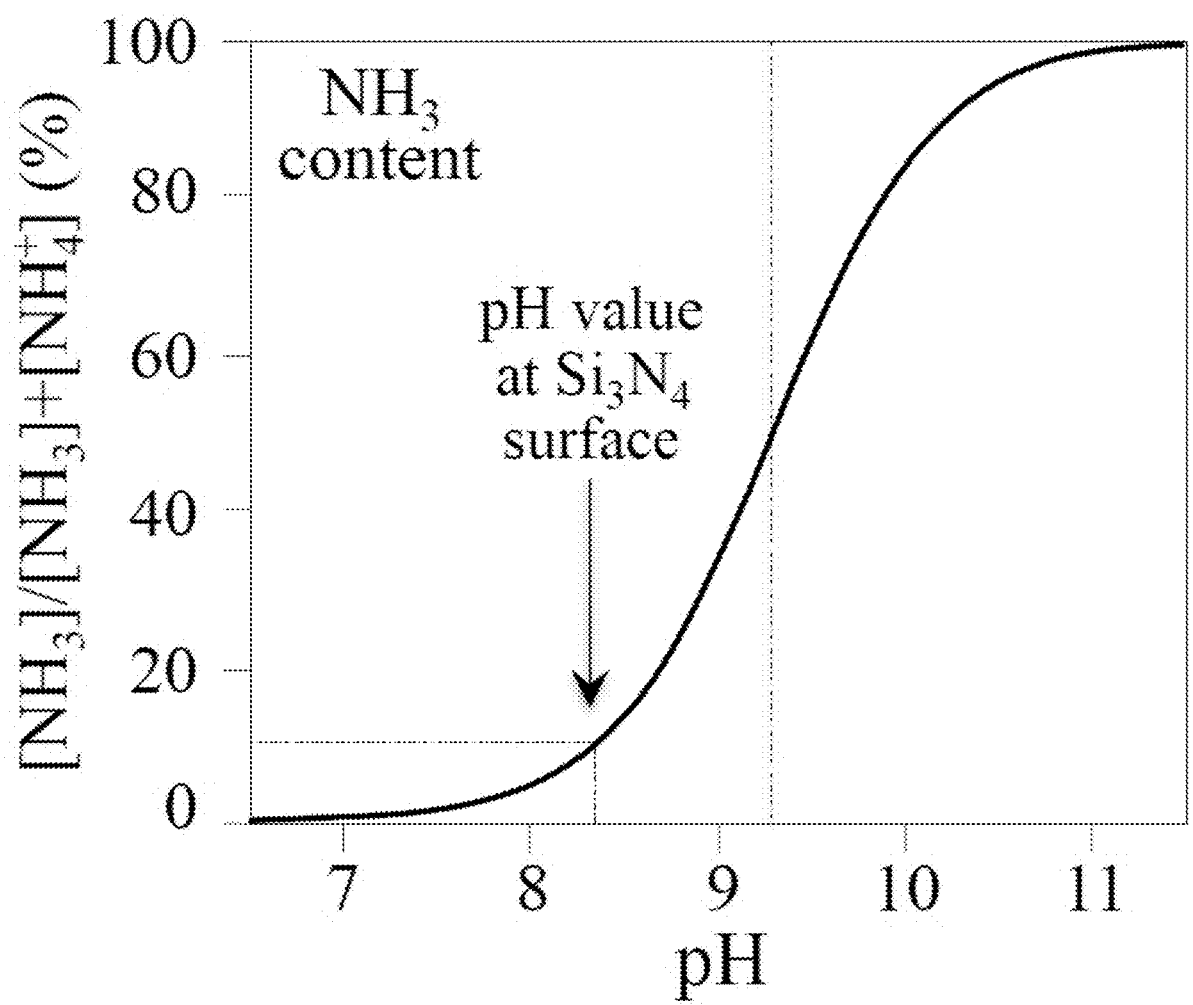
FIG. 7B is a graph depicting the relative fractions of $NH_3$ and $NH_4^+$ in solution of a 15 wt. % $Si_3N_4$ powder dispersed in an aqueous medium as a function of pH.
Figure 7C:
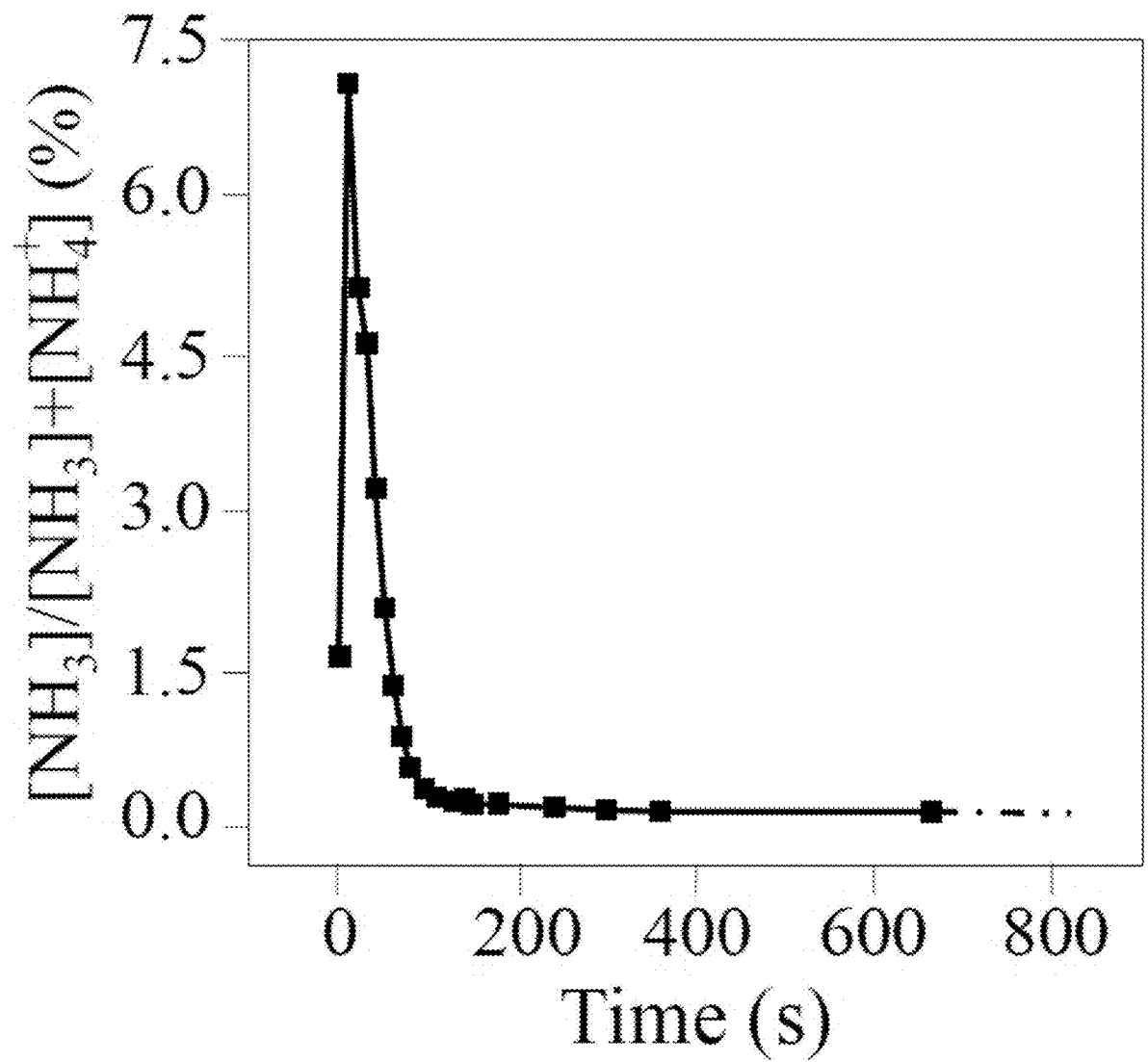
FIG. 7C is a graph showing the relative fraction of eluted $NH_3$ as a function of time in an aqueous dispersion of 15 wt. % $Si_3N_4$ powder.
Figure 7D:
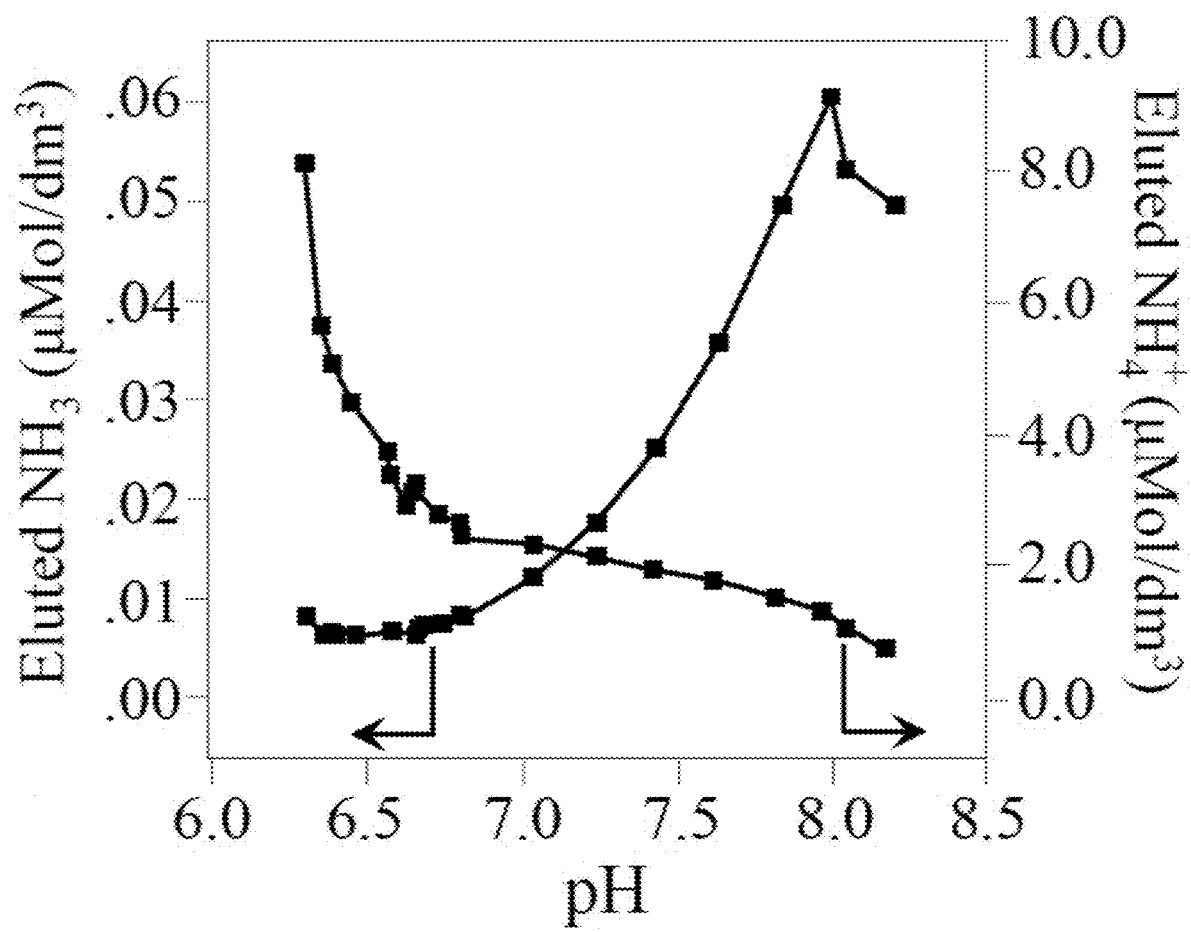
FIG. 7D is a graph showing the molar concentrations of $NH_3$ and $NH_4+$ as a function of pH in an aqueous dispersion of 15 wt. % $Si_3N_4$ powder.

FIG. 7A-7D displays quantitative experimental data from 15 wt. % $Si_3N_4$ powder dispersed in an aqueous medium in terms of: (FIG. 7A) pH variation with time, (FIG. 7B) the relative concentration of $NH_3$ to total $NH_3/NH_4^+$ as a function of pH, (FIG. 7C) the relative fraction of eluted $NH_3$ as a function of time, and (FIG. 7D) the molar concentrations of $NH_3$ and $NH_4^+$ as a function of pH. The data in FIG. 7A show repeated measurements using the same sample after successive wet and dry cycles. These data help to visualize both the kinetics of the nitrogen elution and the overall effect of pH buffering while substantiating the dual role of eluted nitrogen as a fungicidal agent. It can be evinced that: (i) a highly alkaline pH burst (~8.3) occurs within seconds after $Si_3N_4$ is introduced into the aqueous environment; (ii) several repetitions of the measurement with the same $Si_3N_4$-powder samples preserved the alkaline pH burst, but tended to accelerate pH reductions after the initial burst; (iii) the fraction of eluted $NH_3$ at the maximum pH was about 10%, while the remaining fraction was $NH_4^+$; and, (iv) as volatile $NH_3$ left the open system, the pH became acidic due to the presence of $Si(OH)_4$ and $NH_4^+$ ions. Note that the molar concentration of eluted $NH_4^+$ was ~2 orders of magnitude higher than $NH_3$ over the entire pH interval (FIG. 7D). However, $NH_3$ can readily penetrate the membrane and accumulate in the endocytotic space, while $NH_4^+$ can only enter through specific ion channels. For molecules that exist as both neutral and ionic species, bio-membranes are permeable to the former while they require specific carriers for transporting the latter. The speciation balance shown in FIGS. 7A-7D suggests that $NH_4^+$ is the key species in pH buffering. Conversely, highly volatile $NH_3$ plays more of a direct role in antifungal behavior. However, both pH perturbation and ammonia toxicity significantly impact the metabolism of C. albicans.

Figure 8A:
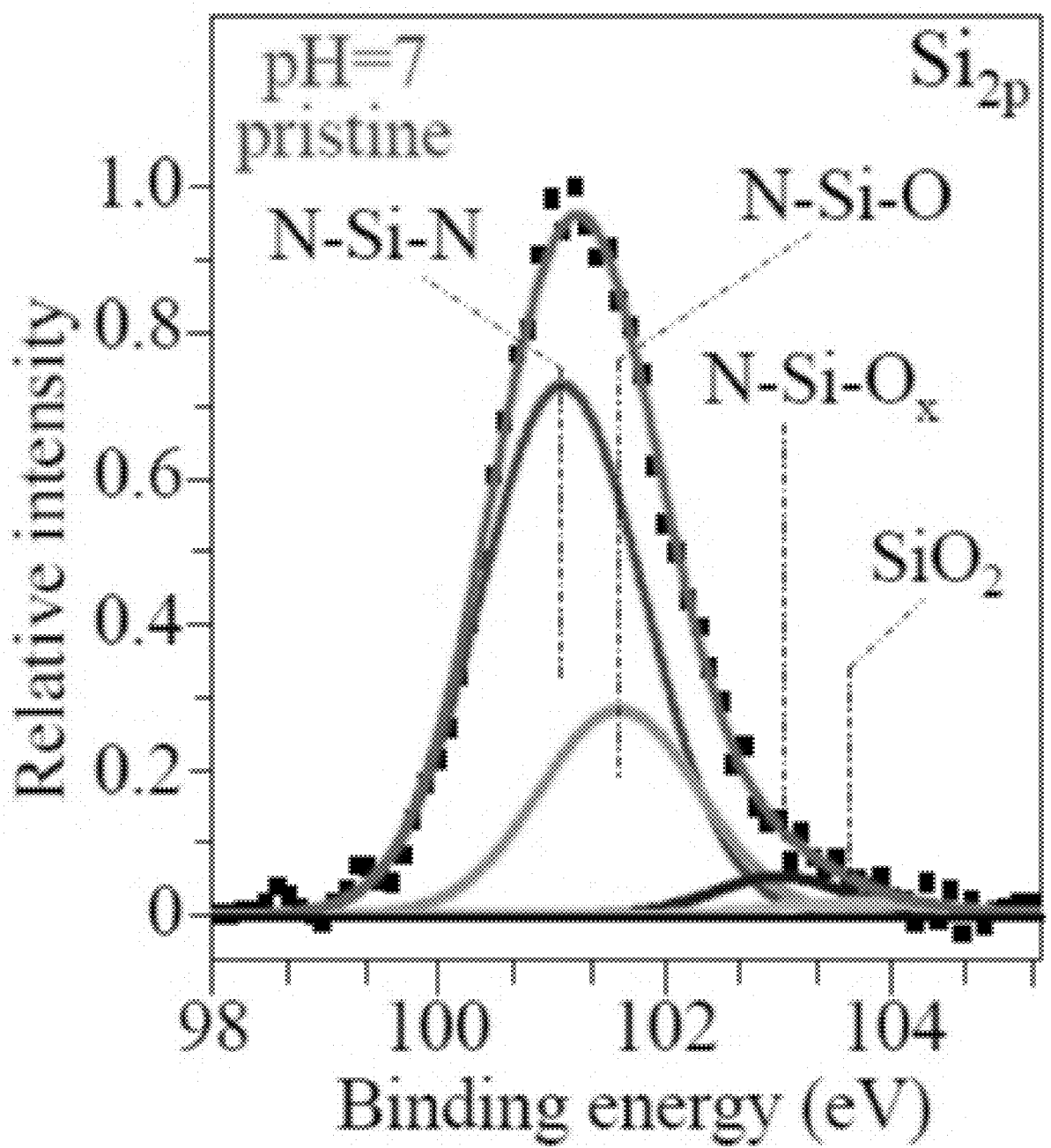
FIG. 8A show average XPS spectra measuring the morphology of the $Si_{2p}$ edge in a pristine $Si_3N_4$ sample not exposed to an aqueous environment.
Figure 8B:
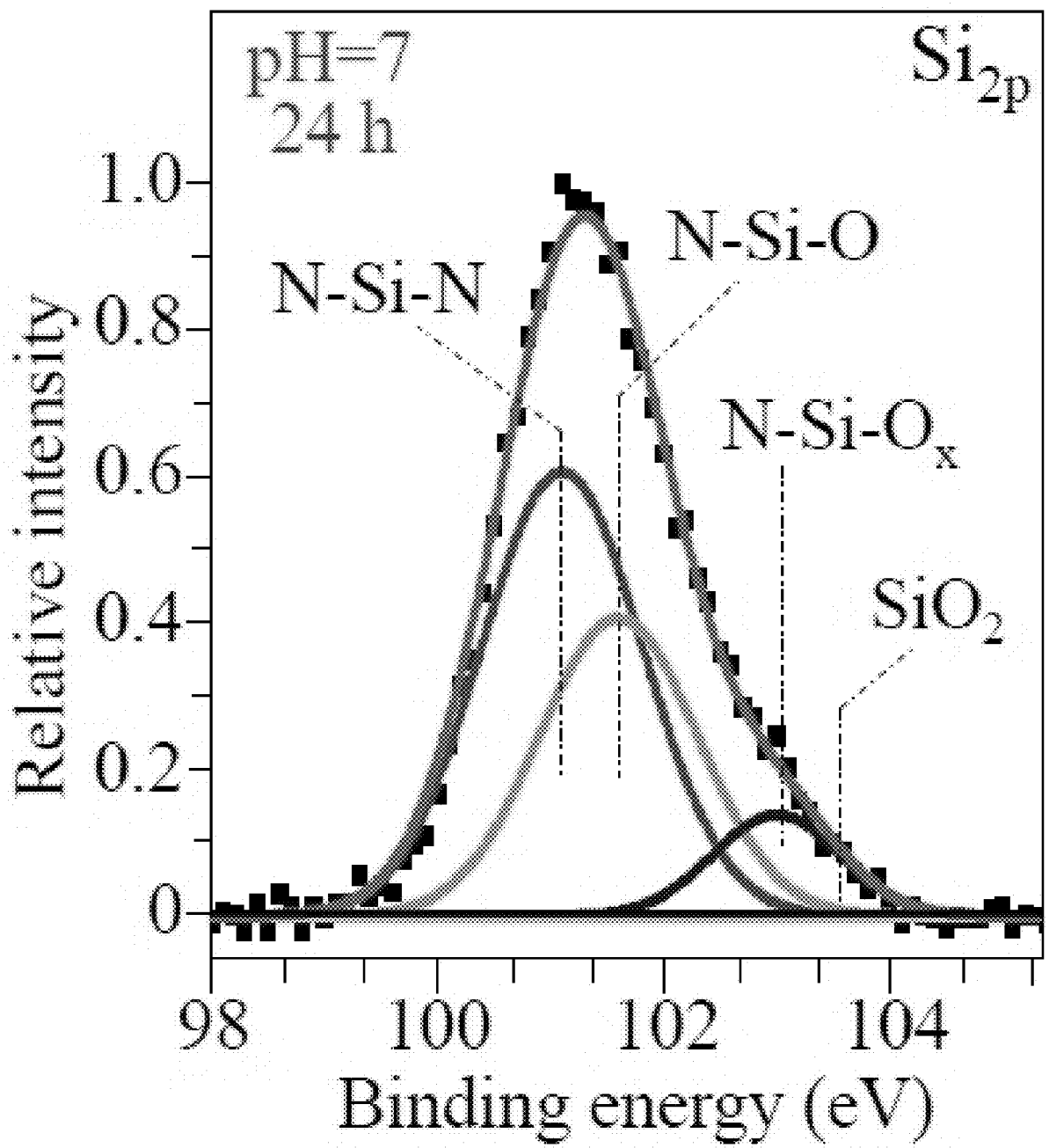
FIG. 8B shows average XPS spectra measuring the morphology of the $Si_{2p}$ edge for bulk $Si_3N_4$ samples as a function of exposure to an aqueous environment at pH=7 for 24 hours.
Figure 8C:
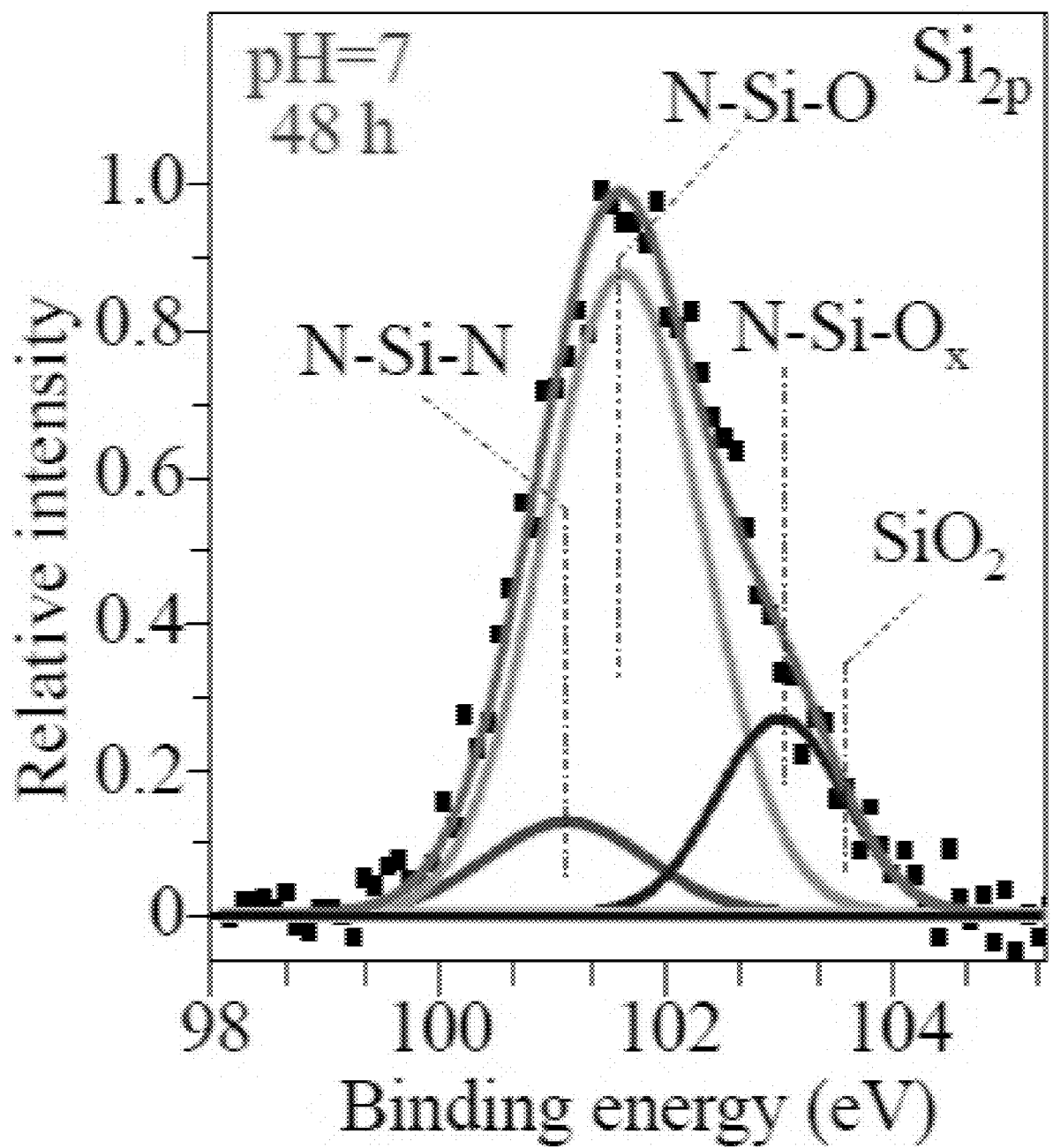
FIG. 8C shows average XPS spectra measuring the morphology of the $Si_{2p}$ edge for bulk $Si_3N_4$ samples as a function of exposure to an aqueous environment at pH=7 for 48 hours.
Figure 8D:
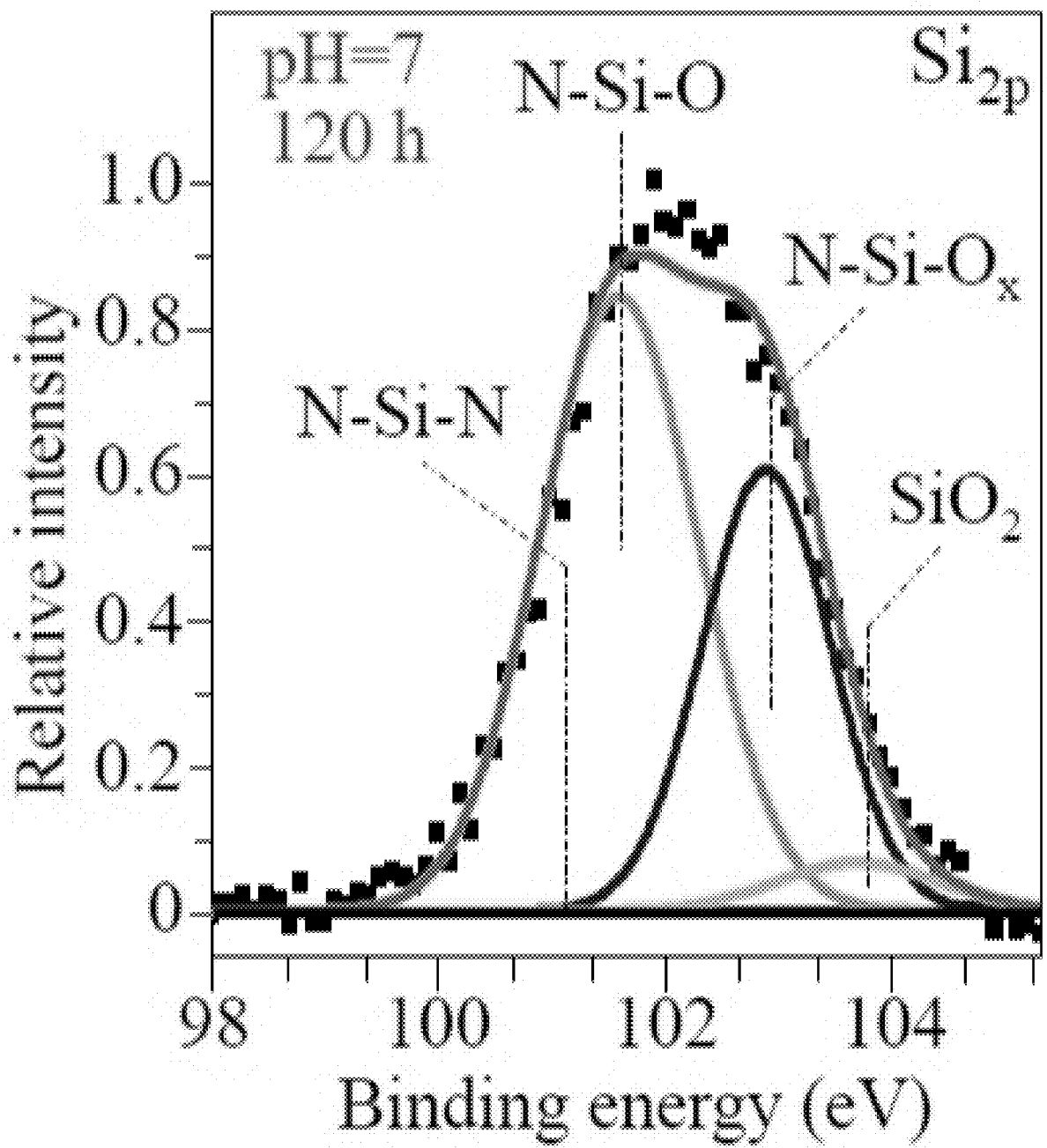
FIG. 8D shows average XPS spectra measuring the morphology of the $Si_{2p}$ edge for bulk $Si_3N_4$ samples as a function of exposure to an aqueous environment at pH=7 for 120 hours.
Figure 8E:
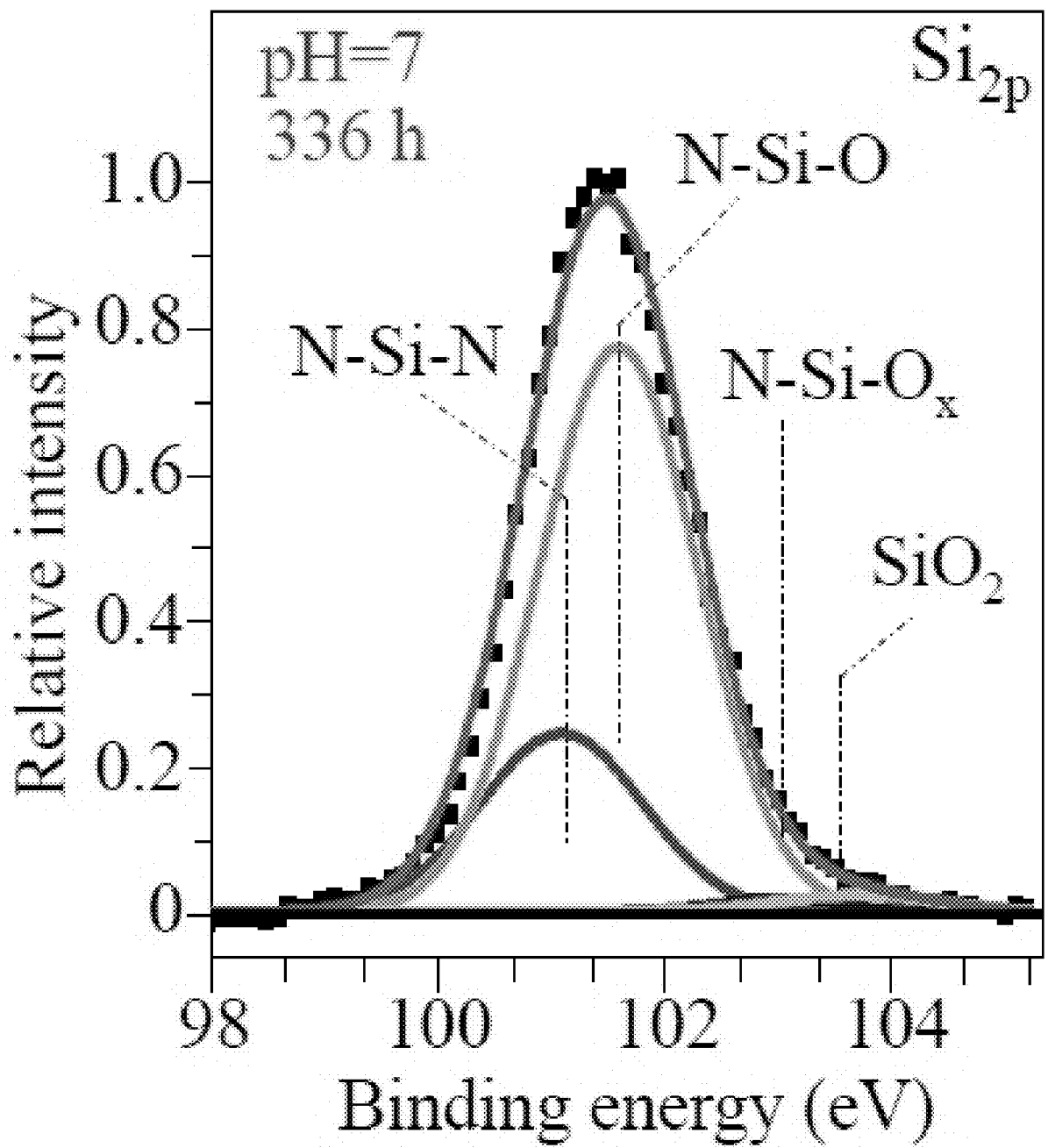
FIG. 8E shows average XPS spectra measuring the morphology of the $Si_{2p}$ edge for bulk $Si_3N_4$ samples as a function of exposure to an aqueous environment at pH=7 for 336 hours.
Figure 8F:
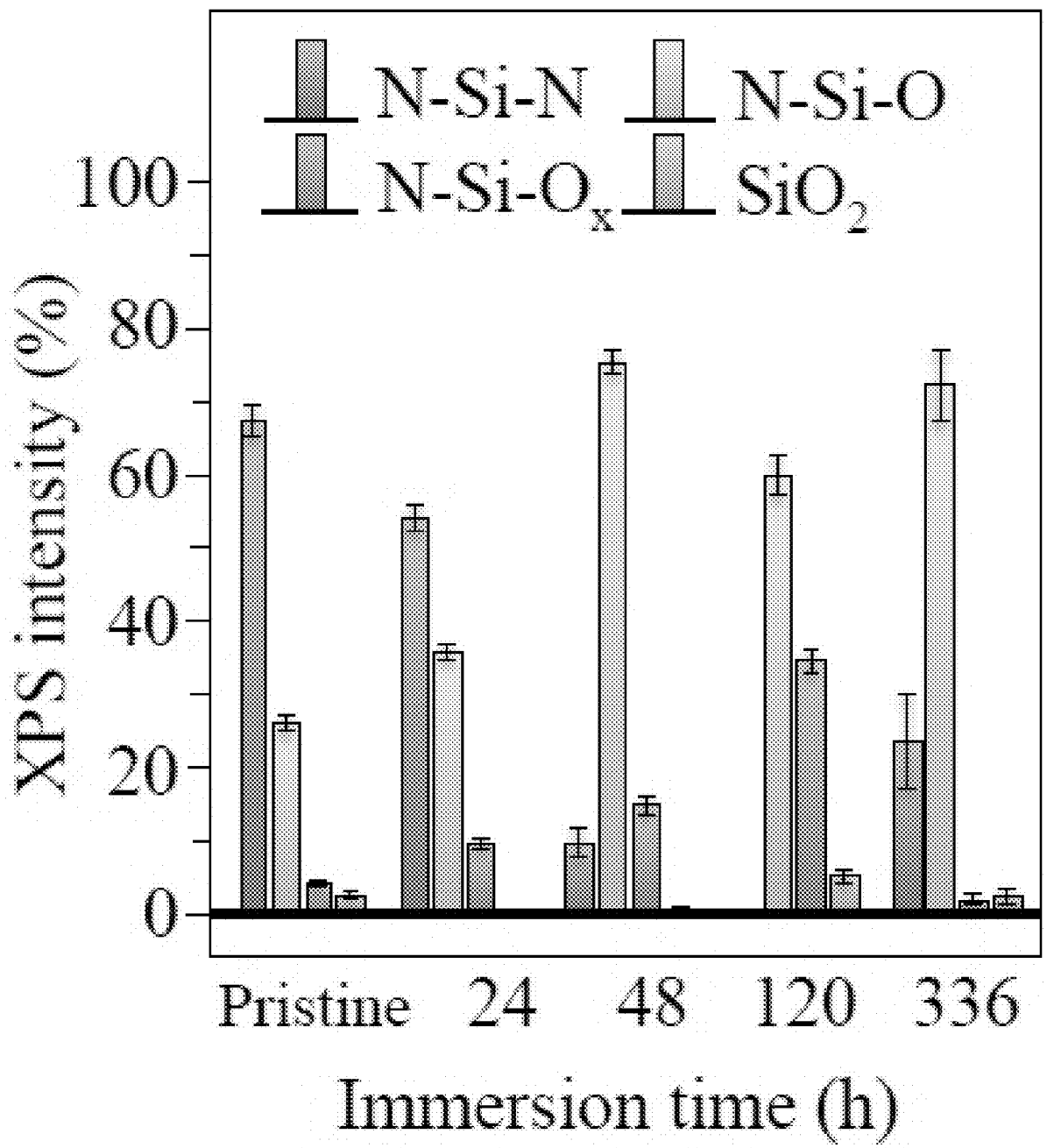
FIG. 8F shows the relative XPS intensity of four sub-bands deconvoluted from the XPS spectra and assigned (from low to high binding energies) to N—Si—N, N—Si—O, N—Si—$O_x$, and O—Si—O (cf labels in the inset) as a function of time.

FIGS. 8A-8F shows a series of averaged XPS spectra for bulk $Si_3N_4$ samples as a function of exposure to an aqueous environment at pH=7 for up to 336 h. The average morphologies of the $Si_{2p}$ edge in the pristine sample, and in exposed samples at pH=7 for 24, 48, 120, and 336 h are shown in FIGS. 8A, 8B, 8C, 8D, and 8E, respectively. Four sub-bands were deconvoluted from the XPS spectra, and assigned (from low to high binding energies) to N—Si—N, N—Si—O, N—Si—$O_x$, and O—Si—O (cf labels in the inset). FIG. 8F shows the relative XPS intensity of the four sub-bands as a function of time. This set of XPS data reveals the evolution of the surface stoichiometry of $Si_3N_4$ after long-term exposure to the aqueous environment. The $Si_3N_4$ surface initially oxidizes to Si—O clusters. However, given the high solubility of silica in water, Si tends to leave the surface (mainly in the form of polymerized silicic acid), and amine sites are then exposed. This was confirmed by data collected after 336 hours (cf. FIGS. 8E and 8F). These data agree with a previous study which clarified the elution kinetics of N and Si according to a colorimetric ammonia assay and inductively coupled plasma atomic emission spectroscopy, respectively. The periodic tendency of $Si_3N_4$ "to refresh" its pristine amine bond population over time suggests that the composite may ultimately have durable antimicrobial activity.

Figure 9A:
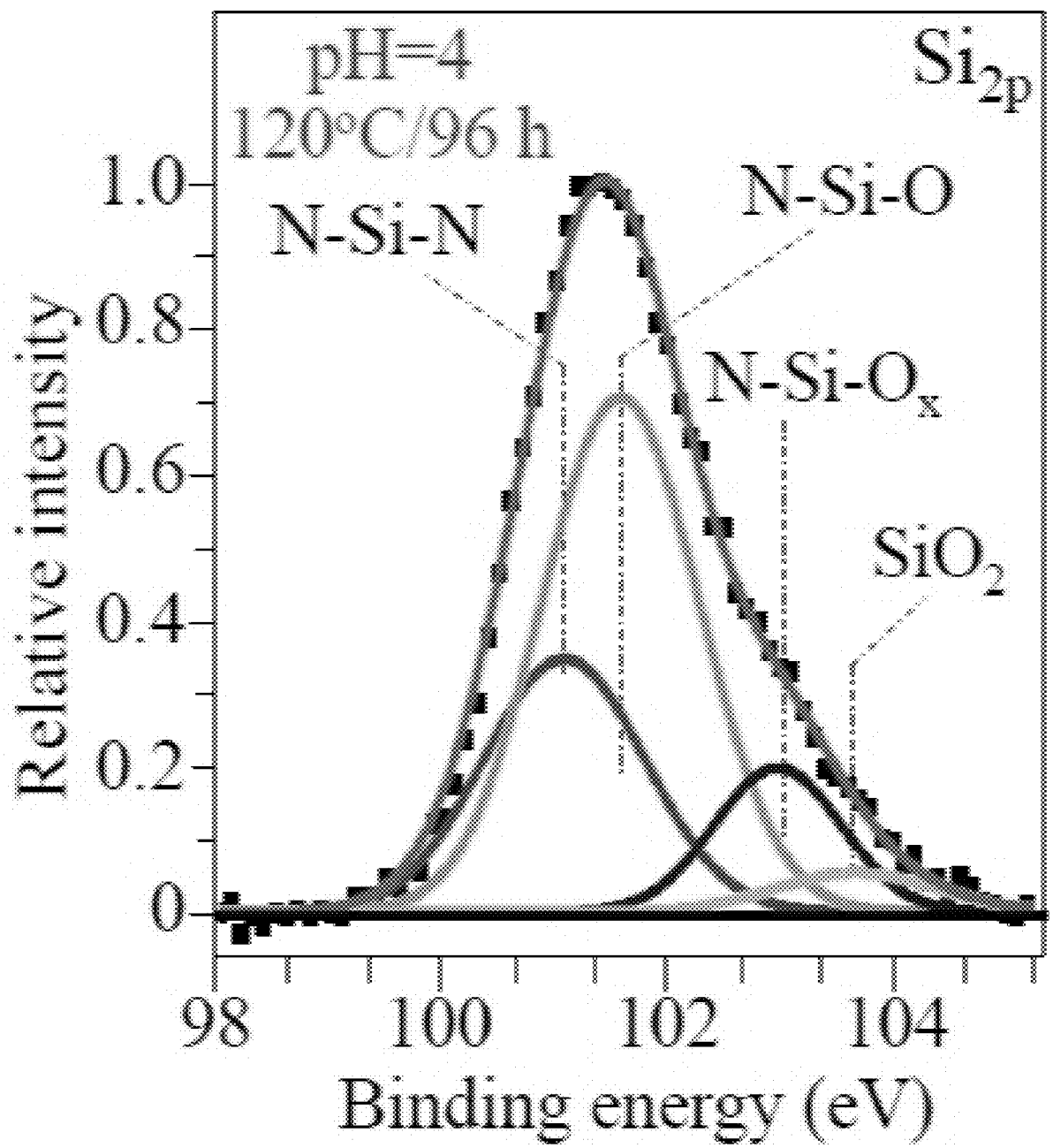
FIG. 9A shows the XPS spectra of a $Si_3N_4$ sample after 96 hours of exposure at a temperature of 120° C. at pH=4.
Figure 9B:
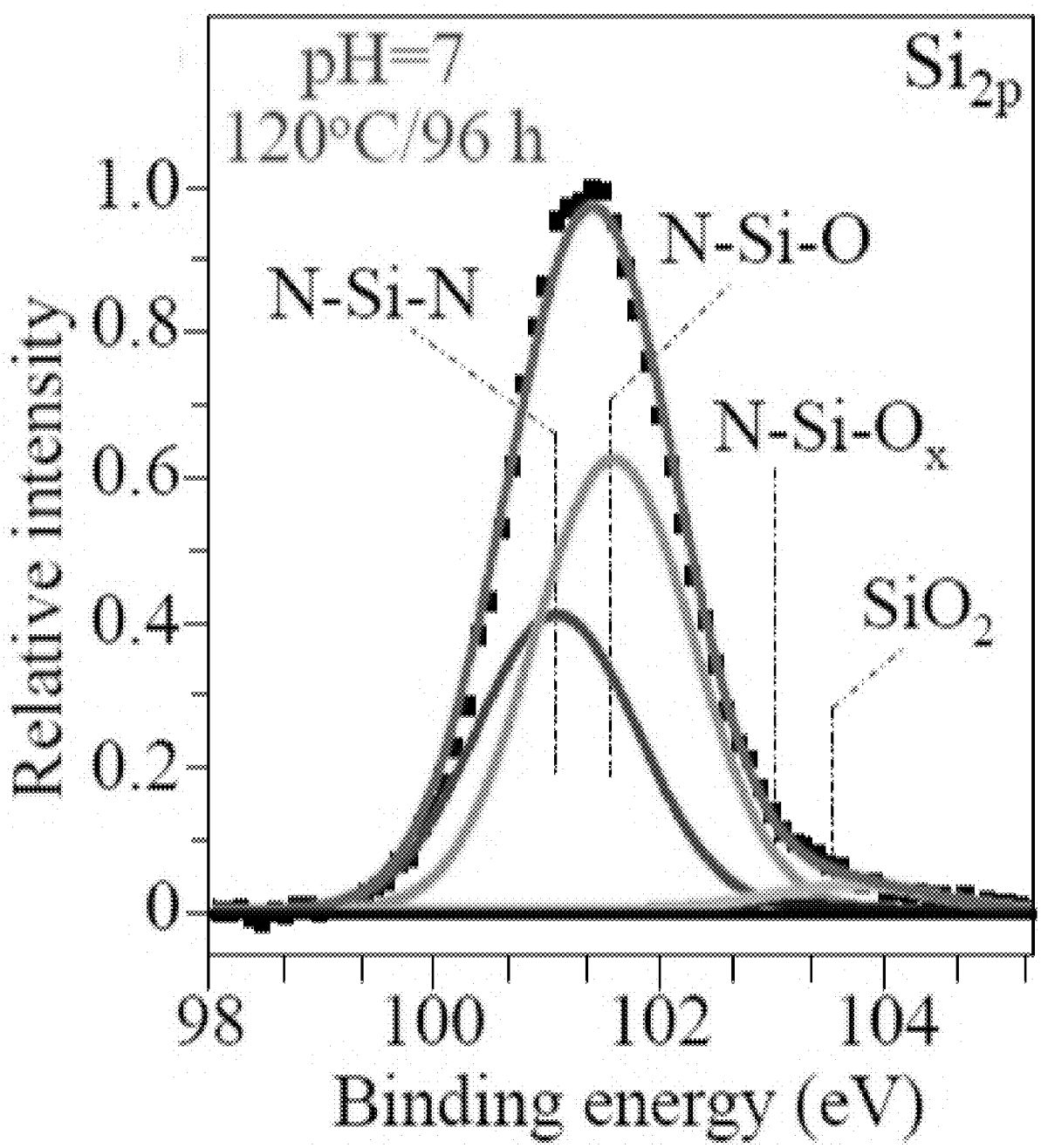
FIG. 9B show the XPS spectra of a $Si_3N_4$ sample after 96 hours of exposure at a temperature of 120° C. at pH=7.
Figure 9C:
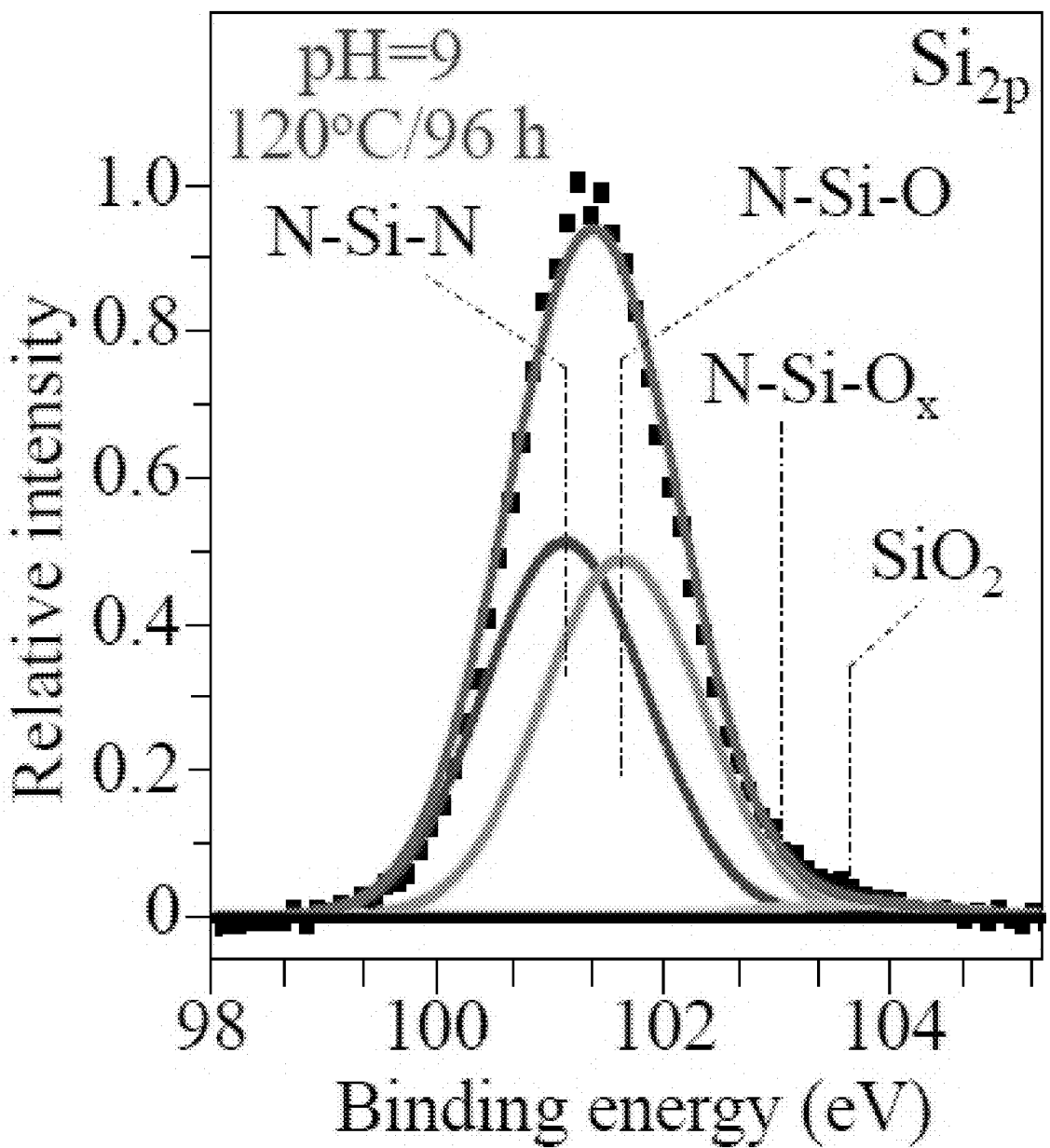
FIG. 9C shows the XPS spectra of a $Si_3N_4$ sample after 96 hours of exposure at a temperature of 120° C. at pH=9.

FIGS. 9A, 9B, and 9C show the XPS spectra of the $Si_3N_4$ sample after 96 hours of exposure at a temperature of 120° C. and for pH values of 4, 7, and 9, respectively. The higher temperature accelerated the kinetics of the off-stoichiometric reactions and clarified the long-term exposure trends. The $Si_3N_4$ surface retained a significant fraction (35, 42, and 51% at pH 4, 7, and 9, respectively) of amine sites (i.e., the fractions of N—Si—N bonds observed in the spectra). These amine sites are important because the liberation of N leads to the formation of $NH_3/NH_4$ and pH buffering. The presence of N—Si—N bonds in the spectra of FIGS. 9A-9C suggests that the observed candidacidal effect may be retained for a relatively long period over a wide pH range.

Example 3: Effect of Silicon Nitride on C. albicans Using Raman Spectra

To monitor the effect of silicon nitride on C. albicans function, in situ Raman spectra were collected on living C. albicans as cultured and after 24 hour exposure to PMMA or PMMA/$Si_3N_4$ composite substrates. Spectra were obtained using a dedicated instrument operating with a 20× optical lens. The spectroscope was set in microscopic confocal mode and used a holographic notch filter. This filter allowed high-efficiency and high-resolution spectral acquisitions. Excitation was made with a 532 nm solid-state laser source with a power of 10 mW, and the Raman scattered light was monitored by a single monochromator connected with an air-cooled charge-coupled device (CCD) detector. The acquisition time of one spectrum was 10 seconds. The spectra used for analyses were average of 30 spectra collected at different locations for each sample. Without removing the yeast cells from the substrates, thirty spectra collected at different locations over an area of ~2 mm² for each type of sample were averaged. Three samples for each substrate type were tested (n=3).

Reference Raman spectra were previously collected on pure compounds. These reference data were compiled into a large library of more than 40 compounds (simply referred to as the "library", henceforth), including polysaccharides (e.g., chitin, β-1,3-glucans, β-1,6-glucans), mono- and disaccharides (e.g., trehalose, β-D-glucose, D-dextrose), lipids (e.g., triolein, trilinolein, 1,2-dipalmitoyl-L-α-lecithin), polyols (e.g., D-(+)-Arabitol and L-(−)-Arabitol), and other key molecules such as adenine, ergosterol, and glycine. The spectra from the pure compounds were collected with a highly resolved spectrometer equipped with a nitrogen-cooled charge-coupled device detector. The excitation source in these latter experiments was a 514 nm line of an Ar-ion laser operating with a nominal power of 200 mW. The spectral resolution was 1.5 cm$^{-1}$.

Raman imaging of *C. albicans* cells was obtained using a dedicated Raman device operated in microscopic measurement mode with confocal imaging capability in two dimensions. The spectroscope was designed to achieve ultra-fast simultaneous image acquisition of up to 400 spectra. The spectroscope is compatible with examining living cells and tissues. It used an excitation source of 785 nm. The spectral resolution was 1.2 cm$^{-1}$ (spectral pixel resolution equal to 0.3 cm$^{-1}$/pixel) with accuracy in peak position of 0.1 cm$^{-1}$. Raman maps were then generated using commercially available software.

Raman spectra were automatically deconvoluted into a series of Gaussian-Lorentzian sub-bands using available software. All spectra were analyzed for their relative intensity after normalization to the glucose ring signal at 483 cm$^{-1}$. To fit the average spectra, $S_{av}(v)$, after exposure of *C. albicans* to the different substrates, an automatic solver, which exploited a linear polynomial expression of Gaussian-Lorentzian functions, $V(\Delta v, \sigma, \gamma)$, was utilized; with v, $\Delta v$, $\sigma$, and $\gamma$ representing the Raman frequency, the shift in frequency from each sub-band's maximum ($v_0$), the standard deviation of each Gaussian component, and the half-width at half-maximum of the Lorentzian component, respectively. A working algorithm was then used match the experimental data, as follows:

$$S_{av}(v) - \Sigma_i \alpha_i \Sigma_j \beta_{ij} V_{ij}(v_0, \Delta v, \sigma, \gamma) \cong 0 \quad (4)$$

where, the index i locates each compound in a series of n compounds contributing to the overall spectrum, and the index j locates each Gaussian-Lorentzian sub-band of a series of m compounds in the Raman spectrum of each compound of an n series. A computer program optimized the algorithm by picking up the series of Gaussian-Lorentzian sub-bands from pre-selected compounds from the library, including mono-, di-, and polysaccharides, specific lipids, polyols, and other key molecules, selected according to previously published literature on the structure of *C. albicans* and other yeasts. Although the library contained Raman spectra from more than 40 different molecules, a pre-selection was made according to the literature. After picking up spectral sub-bands of elementary compounds from the library, the algorithm located the best fit to the experimental spectra. In doing so, the computational procedure preserved relative intensities ($\beta_{ij}$), spectral positions ($v_0$), and full-width-to-half-maximum ($\sigma$ and $\gamma$) values for the individual sub-bands of the deconvoluted spectra from each elementary compound (i.e., within ±3 cm$^{-1}$, considering the resolution of the spectrometer and the possibility of slight molecular structure alterations). These criteria on band positions and bandwidths provided the required constraints to univocally deconvolute the experimental spectra. Adjusting the overall intensity contribution ($\alpha_i$) of each elementary compound within these constraints enabled best fitting of the experimental spectra. The output of the program was twofold: (i) it automatically screened the spectra and proposed a deconvolution by best fitting the experimental spectrum based on Eq. (4), while also indicating the molecules that contributed to each sub-band; and, (ii) it isolated sub-bands whose signal intensity was largely contributed by a single reference molecule (>90%). These sub-bands were then tested by collecting a series of in situ Raman maps on the living yeast cells exposed to the different substrates using the dedicated Raman instrument as described above.

Raman Spectrum of DS-Cultured Yeast Cells

Sabouraud dextrose (DS) agar was prepared by adding 65 grams into one liter of distilled water and successively boiling the mixture. After sterilizing in an autoclave at 121° C. for 15 minutes, the mixture was poured into sterilized 10 cm diameter Petri dishes. *Candida albicans* ATCC® 90028 (*C. albicans*) cells were purchased from the American Type Culture Collection, pre-cultured on Sabouraud dextrose (DS) agar at 36° C. for 48 hours under atmospheric pressure, and then inoculated onto the PMMA and PMMA/Si$_3$N$_4$ substrates with a concentration of 1×10$^6$ cells/dish under atmosphere and then incubated for 24 hours.

Figure 10A:
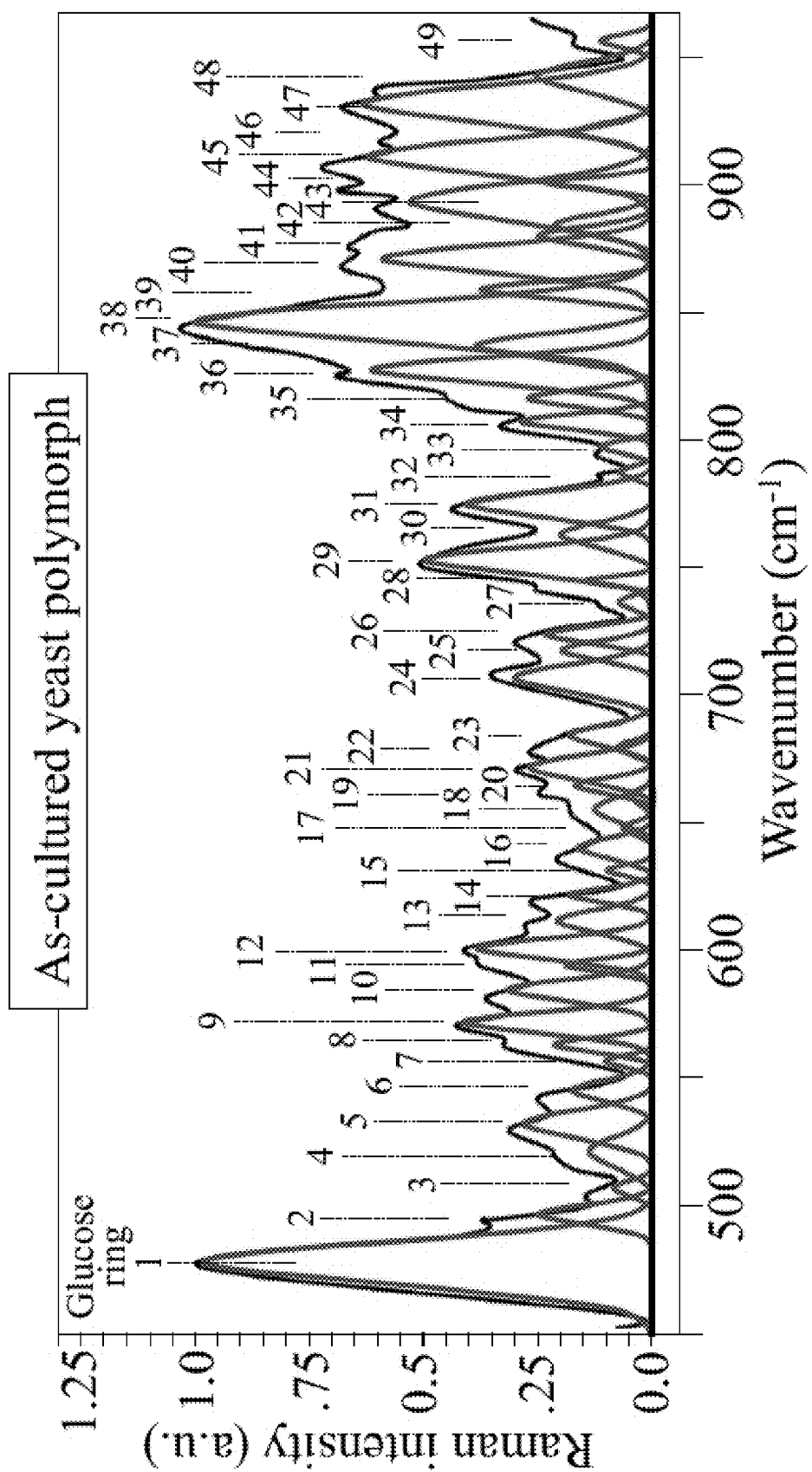
FIG. 10A shows the Raman spectrum of as-cultured *C. albicans*.

The cell walls of *C. albicans* consist of approximately 80~90% carbohydrates. This includes three basic constituents: (i) branched polymeric glucose containing β-glucans; (ii) non-branched polymeric N-acetyl-D-glucosamine containing chitin; and, (iii) polymeric mannose covalently associated with glyco/manno-proteins. The remaining fractions were composed of proteins (6~20%) and by a minor amount of lipids (1~7%). These structural features dominate the low-frequency Raman spectrum of *C. albicans* (FIG. 10A; and Tables 1 and 2 below). Carbohydrate vibrational modes appear in the spectrum as cumulative (backbone) glucose ring signals (Bands 1 at 483 cm$^{-1}$) and as polymerized β-D-glucose chains which have overlapping signals from amylopectin (Bands 13, 30, 38, 40, and 45 at 617, 764, 847, 865, and 910 cm$^{-1}$, respectively). Bands of medium and strong intensity are also observed from chitin (Bands 2 and 16 at 497 and 648 cm$^{-1}$, respectively). The strong Band 38 at 847 cm$^{-1}$ is cumulative of L-(+)-arabinose and D-(+)-glucose (stronger contribution). D-arabinitol is a five-carbon sugar alcohol (pentitol) produced in vitro by several pathogenic and medically important *Candida* species and may be a marker for invasive candidiasis. However, Band 38 is also centered at a frequency characteristic for the α-configuration at the anomeric position. β-D-glucose and α-D-glucose are metabolites common to a wide range of organisms and their contributions to Band 38 indicate a degree of isomerization. The disaccharide trehalose contributes Bands 4, 6, and 37 (at 519, 544, and 838 cm$^{-1}$, respectively), and appears to be the main contributor to Band 12 (at 601 cm$^{-1}$). This disaccharide is an important molecule in the metabolism of *C. albicans* (and many other species of fungi in general) because it acts as an energy source and confers a protective role against environmental stress. In *C. albicans*, the non-reducing trehalose disaccharide is accumulated in response to heat or oxidative stress. In order to take advantage of its double action as carbohydrate reservoir and cellular protector against environmental stress, *C. albicans* promotes the synthesis of trehalose through trehalose-6-phosphate synthase from glucose-6-phosphate and uridine diphosphate glucose (UDP-glucose), followed by hydrolysis.

TABLE 1

| Band | cm$^{-1}$ | Physical origin |
|---|---|---|
| 1 | 483 | Glucose ring vibrations (cellulose, amylose) |
| 2 | 497 | Chitin<br>Glycerol |
| 3 | 513 | N-acetyl-D-glucosamine<br>D-arabitol |
| 4 | 519 | Phosphatidylinositol<br>Trehalose<br>β-D-glucose<br>D-arabitol<br>S—N stretch mode in thiol groups in cysteine & proteins |
| 5 | 533 | N-acetyl-D-glucosamine<br>Adenine<br>D-arabitol |
| 6 | 544 | Trehalose<br>β-D-glucose<br>D-(−)-ribose<br>Glycerol |
| 7 | 555 | N-acetyl-D-glucosamine<br>β-D-glucose<br>Ergosterol |
| 8 | 563 | Chitin |
| 9 | 573 | Deoxyadenosine triphosphate<br>N-acetyl-D-glucosamine |
| 10 | 584 | Cellulose |
| 11 | 594 | Chitin<br>Ergosterol<br>Glycerol |
| 12 | 603 | Trehalose<br>D-arabitol |
| 13 | 617 | Amylopectin<br>Ergosterol |
| 14 | 622 | Adenine<br>D-arabitol<br>Sulfhydryl C—S modes after binding to NO |
| 15 | 634 | Out-of-plane C—O—H bend glycerol |
| 16 | 648 | Deoxyadenosine triphosphate<br>Chitin<br>D-arabitol |
| 17 | 650 | Deoxyguanosine triphosphate<br>Chitin |
| 18 | 655 | D-dextrose<br>Histidine |
| 19 | 661 | Guanine & thymine ring breathing<br>D-arabitol |
| 20 | 663 | C—S stretching in DNA cysteine<br>D-arabitol |
| 21 | 670 | C—S stretching<br>Glycerol |
| 22 | 681 | Ring breathing in RNA guanine |
| 23 | 680 | N-acetyl-D-glucosamine |
| 23* | 698 | Sulfhydryl C—S modes after binding to NO |
| 24 | 709 | Chitin<br>Ergosterol<br>Ring breathing in DNA cytosine<br>D-arabitol |
| 25 | 719 | C—N stretch in phosphatidylcholine<br>D-arabitol<br>Ergosterol |

TABLE 2

| Band | cm$^{-1}$ | Physical origin |
|---|---|---|
| 26 | 720 | Lecithin<br>Adenine |
| 27 | 734 | Phosphatidylserine<br>Trehalose |
| 28 | 747 | Deoxythymidine triphosphate<br>D-arabitol |
| 29 | 749 | Deoxyadenosine triphosphate<br>B$_{1g}$ heme vibration in cytochrome c |
| 30 | 764 | Deoxythymidine triphosphate<br>Amylose/amylopectin<br>Lecithin |
| 31 | 775 | D-glucose<br>DNA phosphodiester stretching<br>D-arabitol |
| 32 | 784 | Phosphatidylserine<br>Histidine<br>D-arabitol |
| 33 | 799 | Deoxycytidine triphosphate |
| 34 | 810 | 2-deoxy-D-ribose (glucan)<br>Glycerol |
| 35 | 816 | Trioleate |
| 36 | 827 | Ergosterol<br>Lecithin<br>D-arabitol |
| 37 | 838 | Trilinoleate<br>D-dextrose<br>Trehalose<br>β-D-glucose<br>D-arabitol |
| 38 | 847 | L-(+)-arabinose (glucan)<br>D-(+)-glucose<br>Glycerol<br>Amylopectin<br>Trehalose |
| 39 | 863 | Phosphatidylethanolamine<br>Trioleate |
| 40 | 865 | N-acetyl-D-glucosamine<br>Trilinolenin<br>Triolein<br>Amylose/amylopectin<br>D-arabitol |
| 41 | 875 | C—N stretch phosphatidylcholine<br>Lecithin<br>Trilinolein<br>Triolein |
| 42 | 881 | Phosphatidylethanolamine<br>D-arabitol |
| 42* | 885 | S—N—O bending mode in nitrosylated proteins |
| 43 | 892 | Chitin<br>Lecithin<br>Trioleate<br>Phosphatidylserine<br>PS + D-(−)-ribose (glucan)<br>D-arabitol |
| 44 | 900 | β-D-glucose<br>Adenine<br>D-arabitol |
| 45 | 910 | D-dextrose<br>Trehalose<br>β-D-glucose<br>Amylose/Amylopectin<br>D-arabitol |
| 46 | 921 | Chitin<br>D-arabitol |
| 47 | 932 | Histidine<br>β-D-glucose<br>D-arabitol |
| 48 | 941 | Adenine<br>Trilinolenin<br>D-arabitol |
| 49 | 952 | Deoxyadenosine triphosphate<br>Lecithin<br>D-arabitol<br>Glycerol |

Fractional differences between mono- and di-saccharides can be estimated by comparing Band 12 and Band 44 (at 900 cm$^{-1}$), the latter signal is primarily contributed by β-D-glucose. N-acetyl-D-glucosamine is an amide derivative of the monosaccharide glucose, whose principal Raman signatures appear at 513, 533, 555, 680, and 865 cm$^{-1}$ (Bands 3, 5, 7, 23, and 40, respectively). However, only Bands 3 and 23 appear to be contributed by N-acetyl-D-glucosamine alone.

The glycerophospholipid lecithin possesses characteristic bands at 720, 764 and 827 cm$^{-1}$ (i.e., Bands 26, 30, and 36, respectively), which are due to C—N stretching, O—P—O symmetric, and antisymmetric stretching (choline group), respectively. However, other fingerprints of lipids can be found in the region 800~950 cm$^{-1}$, where triacylglycerol molecules greatly influence the *C. albicans* spectrum. In this region, the strongest signal is Band 38 from glucose and glucans, but several medium/strong bands are due to triglycerides and phospholipids (cf. Table 2). Trilinolenin displays an intense band at 865 cm$^{-1}$, while relatively broad signals of medium intensity from triolein and trilinolein appear at frequencies of 865 and 875 cm$^{-1}$. Although it is hard to single out individual contributions from different lipids (because of band overlap) from the spectrum in FIG. 10A, the fingerprints of lipid-related bands are consistent with their biological function as energy reservoirs for cell proliferation.

Besides polysaccharides and lipids, additional biomolecules contributing to the spectrum in FIG. 10A are adenine (found in nucleic acid) and ergosterol. Band 14 is contributed by adenine (at 622 cm$^{-1}$), while Bands 5, 26, 44, and 48 (at 533, 720, 900, and 941 cm$^{-1}$, respectively) overlap with signals from different molecules including N-acetyl-D-glucosamine, lecithin, β-D-glucose, and trilinolenin. Ergosterol is a 5,7-diene oxysterol, which is the most abundant sterol in fungal cell membranes. It displays a complex Raman spectrum, including bands at 594, 617, 709, and 827 cm$^{-1}$ (i.e., Bands 7, 11, 13, 25, and 36, respectively). The steroid ergosterol is an essential component in the cell membrane. It modulates fluidity, permeability, and integrity. It should also be noted that *C. albicans* is incapable of taking up sterols from external sources under anaerobic conditions. Therefore, storage and metabolism of sterols rely on internal synthesis. Under environmental stress, they regulate and control both morphological transformations and biofilm formation.

Variation of *C. albicans* Raman Spectrum on Different Substrates

Figure 10B:
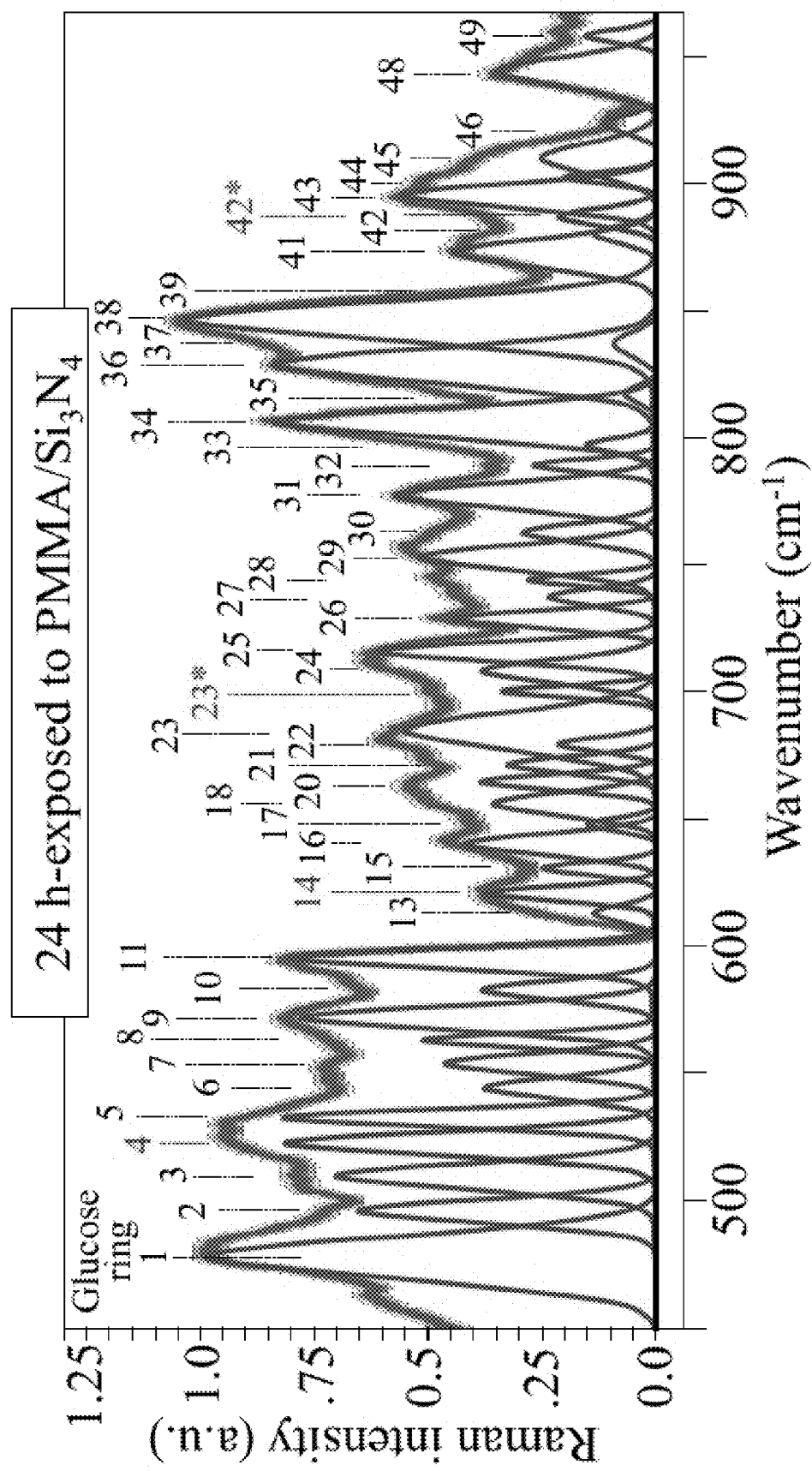
FIG. 10B shows the Raman spectrum of the as-cultured *C. albicans* cells in FIG. 10A exposed to PMMA/$Si_3N_4$ substrate for 24 hours.

Increased nitric oxide (NO) activity for both eukaryotic and prokaryotic cells on Si$_3$N$_4$ substrates were previously demonstrated. NO is expected to accelerate the intrinsic enzymatic activity of eukaryotic cells and the nitrosylation of thiol/disulfide groups of key proteins. However, exposure to concentrations of NO and other RNS beyond a certain threshold causes nitrosative stress and leads to several molecular alterations, such as the S-nitrosylation of the thiol groups of cysteines in proteins and glutathione. Raman spectroscopy has previously been used to explore protein nitrosylation. Features have been identified which show a direct interaction between NO and thiol groups. Others have stated that NO does not interact directly with thiols and that S-nitrosation requires formation of reactive nitrogen oxide species (RNOS) derived from NO, such as dinitrogen trioxide N$_2$O$_3$ and peroxynitrite ONOO$^-$. Accordingly, thiol-group nitrosylation fingerprints were looked for in the Raman spectrum of *C. albicans* after exposure to PMMA/Si$_3$N$_4$ (FIG. 10B) in comparison to the pristine spectrum of the as-cultured yeast cells (FIG. 10A). The intensity enhancement of the features at 519 cm$^{-1}$ (Band 4; emphasized in red color in FIG. 10B) and 622 cm$^{-1}$ (Band 14; emphasized in red color in FIG. 10B) were attributed to S—N stretch modes in thiol groups of cysteine and proteins and to sulfhydryl C—S modes after binding to NO, respectively. Conversely, the feature at 698 cm$^{-1}$ (Band 23*; emphasized in red color in FIG. 10B) is a new vibrational mode only present in the Raman spectrum of *C. albicans* exposed to the PMMA/Si$_3$N$_4$ substrate. The frequency of this new band corresponds to stretching of sulfhydryl C—S modes after binding to NO. This is the same origin as Band 14. Another new signal peculiar to the PMMA/Si$_3$N$_4$ composite was Band 42* (at 885 cm$^{-1}$; emphasized in red color in FIG. 10B), whose origin is an S—N—O bending mode in nitrosylated proteins. These spectroscopic fingerprints consistently point to the effect of an exogenous source of nitrogen-rich molecules and their metabolic modifications to *C. albicans* by NO and other RNS.

Three additional features in the Raman spectrum of the yeast cells exposed to PMMA/Si$_3$N$_4$ were: (i) a strong increase in the bands contributed by glycerol (i.e., Bands 11, 21, 34 and 49 at 594, 664, 810, and 952 cm$^{-1}$, respectively); (ii) a comparably strong increase of Bands 7 and 25 (at 555 and 719 cm$^{-1}$), which are primarily contributed by ergosterol; and, (iii) the complete disappearance of Band 12 at 603 cm$^{-1}$, which is a weak band in the spectrum of trehalose and d-arabitol, but represents a significant fingerprint because it is only contributed by these two molecules. These characteristics provide important information on cellular metabolism after exposure to the PMMA/Si$_3$N$_4$ substrate.

*C. albicans* possesses a complex defensive response to stress, including abnormal synthesis of trehalose, ergosterol, glycerol and d-arabitol in a stress-dependent manner. It has been reported that trehalose and d-arabitol accumulate in response to oxidative stress, while osmotic challenges induce the abnormal storage of glycerol. In response to osmotic stress, an enhancement of ergosterol occurs in the endoplasmic reticulum to modulate membrane fluidity and permeability. Storage of polyol glycerol, enhancement of ergosterol, with only a slight reduction of disaccharide trehalose and polyol d-arabitol, in the Raman spectrum of *C. albicans* exposed to PMMA/Si$_3$N$_4$ was found. These spectral fingerprints consistently suggest that the yeast cells were subjected to a combination of nitrosative and osmotic stresses rather than oxidative stress.

Figure 10C:
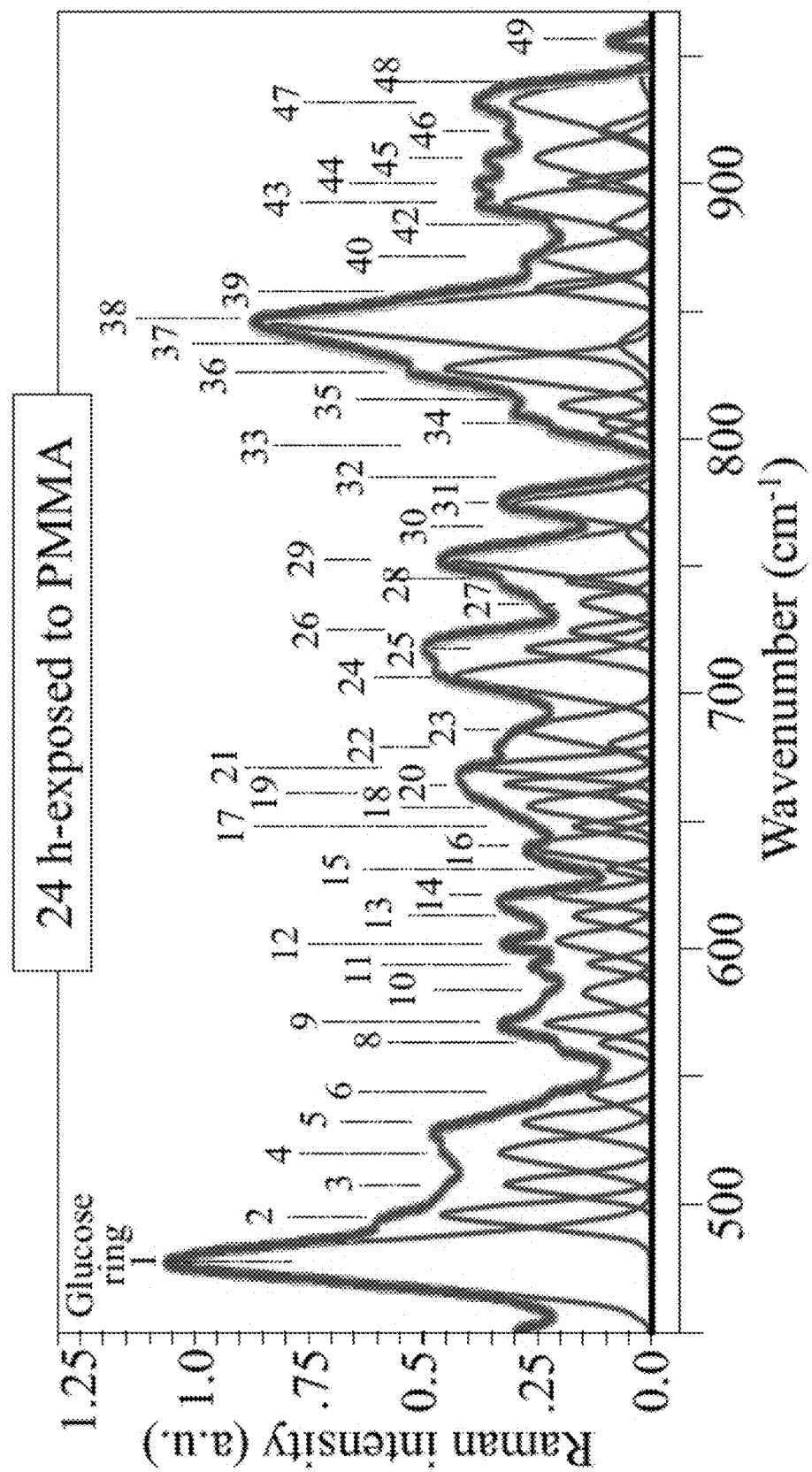
FIG. 10C shows the Raman spectrum of the as-cultured *C. albicans* cells in FIG. 10A exposed to PMMA control substrate for 24 hours.
Figure 11A:
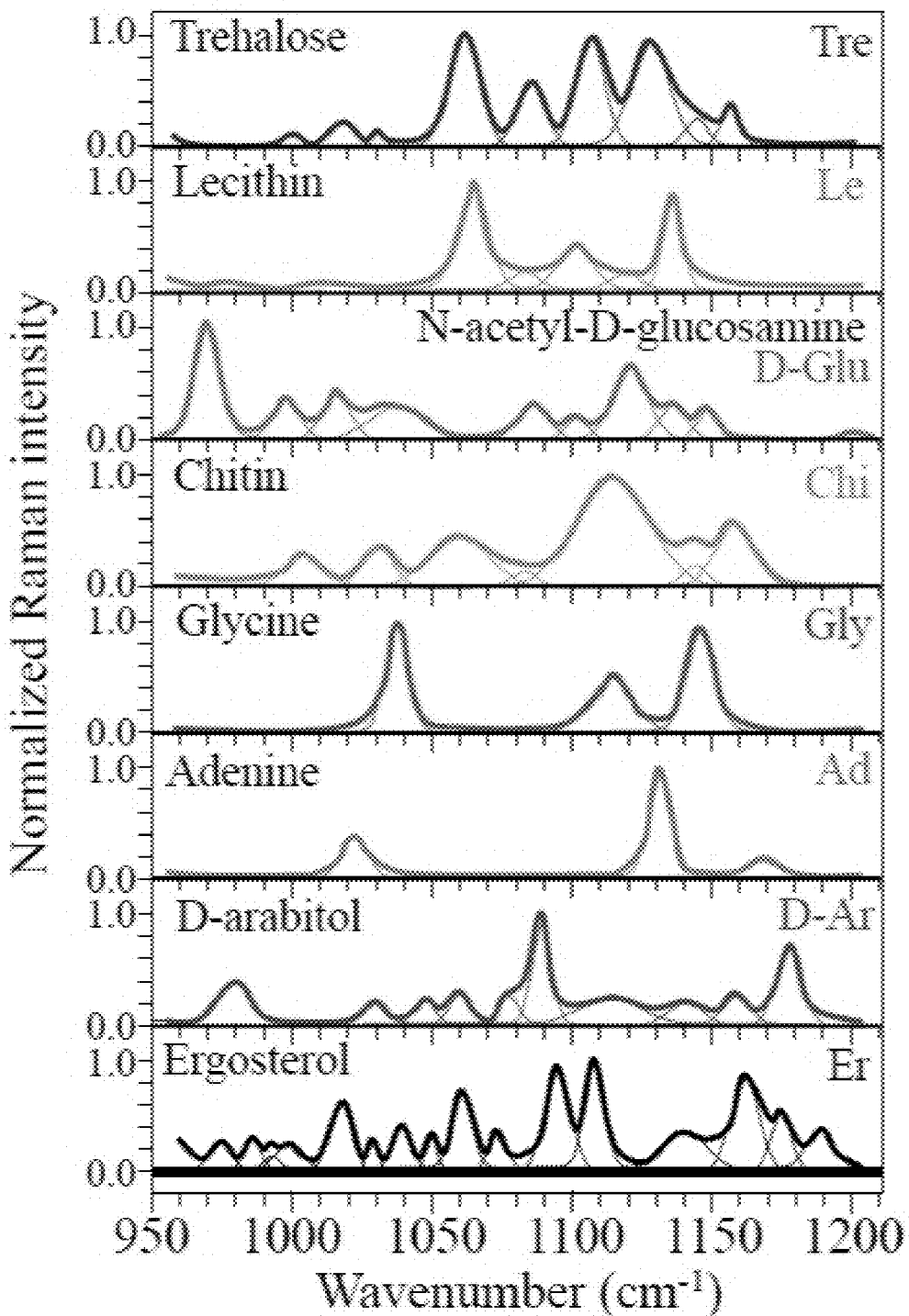
FIG. 11A shows deconvoluted Raman spectra of 8 elementary compounds included in a library for the spectral region 950~1200 $cm^{-1}$.
Figure 11B:
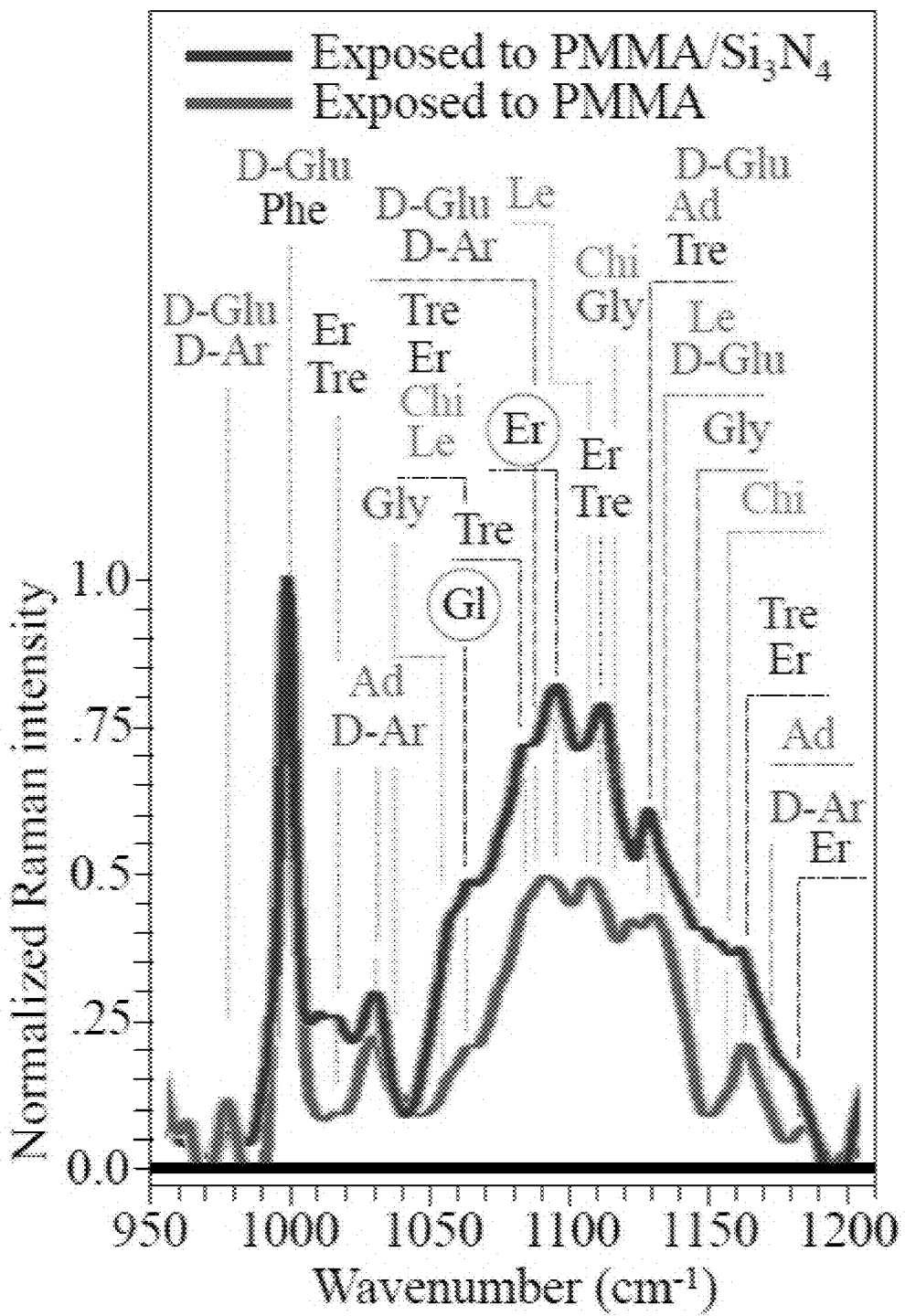
FIG. 11B shows band assignments of experimental spectra collected on yeast cells according to an automatic solver algorithm matching the experimental spectra to the database in FIG. 11A.
Figure 12A:
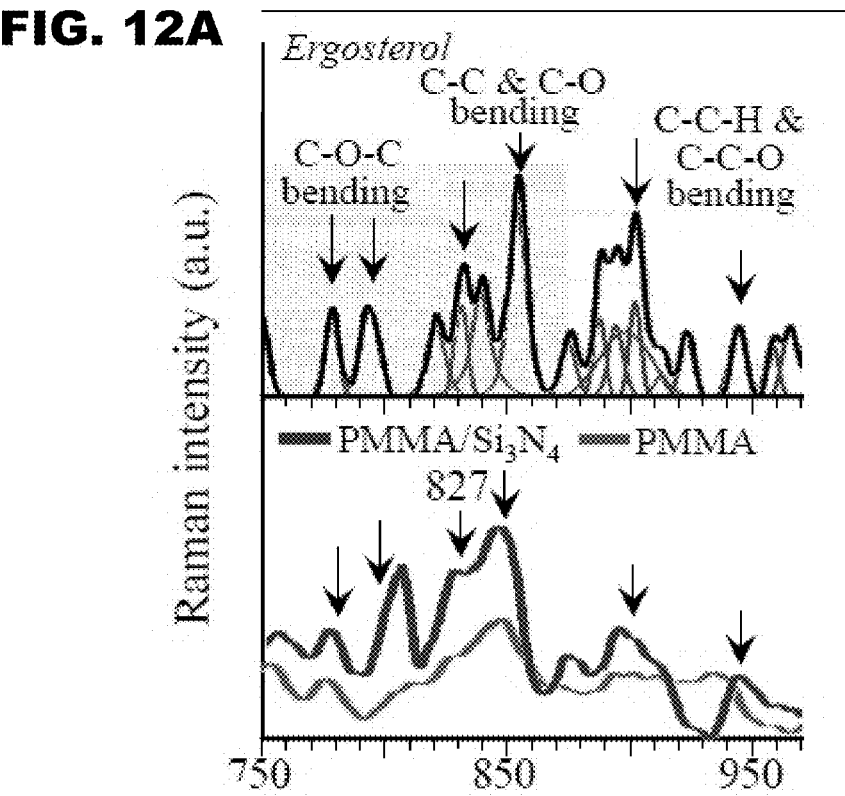
FIG. 12A shows the Raman spectrum of pure ergosterol (upper spectrum with labels for band origins) and the average Raman spectra of yeast cells exposed to PMMA/$Si_3N_4$ and pure PMMA substrates (lower spectra) for the spectral zones 750~970 $cm^{-1}$.
Figure 12B:
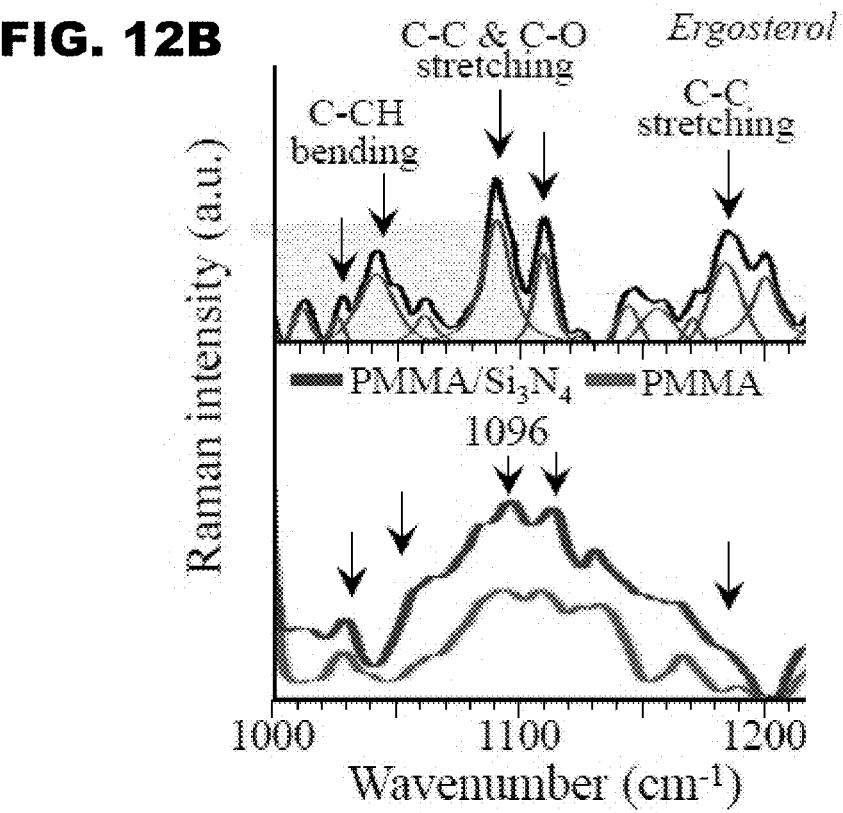
FIG. 12B shows the Raman spectrum of pure ergosterol (upper spectrum with labels for band origins) and the average Raman spectra of yeast cells exposed to PMMA/$Si_3N_4$ and pure PMMA substrates (lower spectra) for the spectral zones 1000~1200 $cm^{-1}$.
Figure 13A:
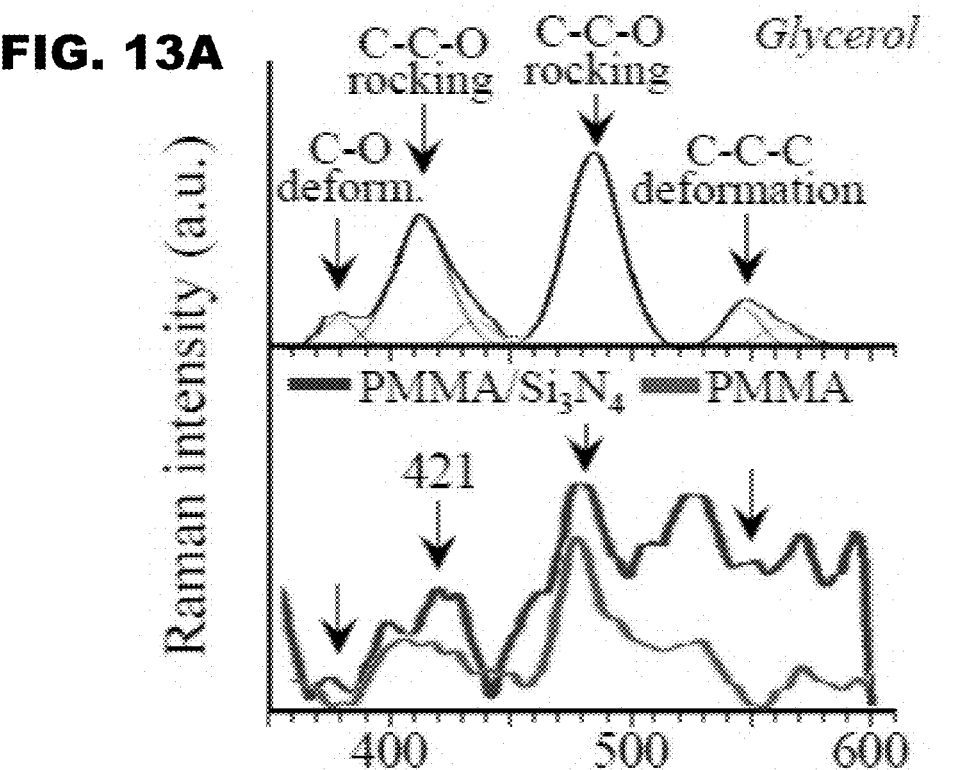
FIG. 13A shows the Raman spectrum of pure glycerol (upper spectrum with labels of band origins) and average Raman spectra of yeast cells exposed to PMMA/$Si_3N_4$ and pure PMMA (lower spectra) for the spectral zone of 350~600 $cm^{-1}$.
Figure 13B:
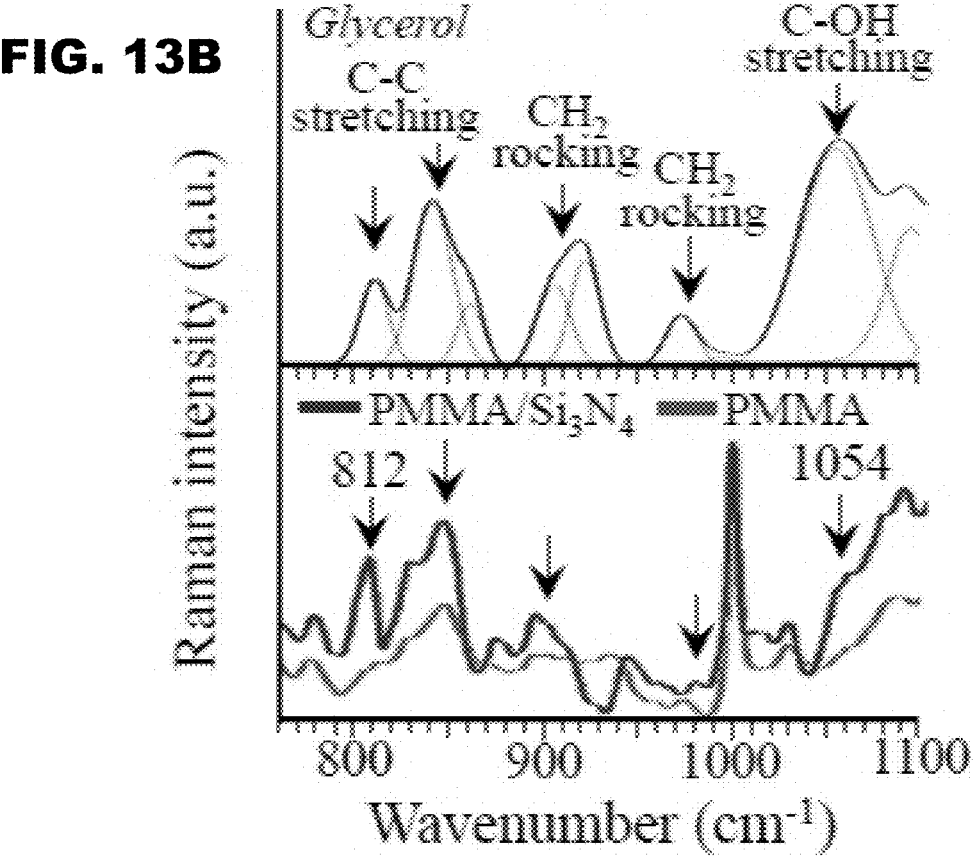
FIG. 13B shows the Raman spectrum of pure glycerol (upper spectrum with labels of band origins) and average Raman spectra of yeast cells exposed to PMMA/$Si_3N_4$ and pure PMMA (lower spectra) for the spectral zone of 760~1100 $cm^{-1}$.

To obtain further spectroscopic evidence of the enhancement of ergosterol and glycerol concentration when yeast cells were exposed to the PMMA/Si$_3$N$_4$ substrates, in situ Raman maps were collected at specific frequencies contributed mainly (>90%) by these compounds. FIG. 11A shows deconvoluted Raman spectra of 8 elementary compounds included in a library for the spectral region 950~1200 cm$^{-1}$. In FIG. 11B, the band assignments of experimental spectra collected on yeast cells is provided according to an automatic solver algorithm matching the experimental spectra to the database in FIG. 11A. A comparison is carried out between yeast cells exposed for 24 h to PMMA/Si$_3$N$_4$ and pure PMMA substrates. This automatic procedure reveals complex overlapping contributions for almost the totality of the bands in this spectral zone except for one main band of glycerol and one main band of ergosterol located at 1056 and 1096 cm$^{-1}$, respectively (cf encircled labels in the inset), which are assumed as Raman fingerprints for these molecules. A similar procedure was adopted in different spectral zones, which located another fingerprint band for ergosterol at 827 cm$^{-1}$ and two additional fingerprint-frequencies for glycerol at 421 and 812 cm$^{-1}$. FIGS. 12A and 12B show the Raman spectrum of pure ergosterol (upper spectrum with labels for band origins) and the average Raman spectra of yeast cells exposed to PMMA/Si$_3$N$_4$ and pure PMMA substrates (lower spectra) for the spectral zones 750~970 cm$^{-1}$ and 1000~1200 cm$^{-1}$, respectively. The results of in situ Raman mapping for the ergosterol bands at 827 and 1096 cm$^{-1}$ are given in FIGS. 12C and 12D, respectively. In these figures the upper, middle, and lower maps correspond to yeast cells exposed to pure PMMA, 15 wt. % Si$_3$N$_4$ in PMMA, and 75 wt. % Si$_3$N$_4$ in PMMA, respectively. A significant enrichment in ergosterol was observed for yeast cells exposed to PMMA substrates containing $Si_3N_4$ as compared to PMMA only. On the other hand, no appreciable difference was found between cells exposed to either of the PMMA/$Si_3N_4$ composites. FIGS. 13A-13O show a similar in situ Raman analysis for glycerol. In FIGS. 13A and 13B, the Raman spectrum of pure glycerol (upper spectrum with labels of band origins) and average Raman spectra of yeast cells exposed to PMMA/$Si_3N_4$ and pure PMMA (lower spectra) are shown for the spectral zones 350~600 $cm^{-1}$ and 760~1100 $cm^{-1}$, respectively. The images in FIGS. 13C and 13D represent in situ maps of glycerol for yeast cells exposed to PMMA and PMMA/$Si_3N_4$, respectively. Upper, middle, and lower images were taken at Raman frequencies of 421, 812, and 1054 $cm^{-1}$, respectively. These frequencies were located as fingerprints of glycerol (>90% intensity contribution) by automatic software screening on the Raman database. Note that screening of all the three frequencies consistently revealed an intracellular enrichment in glycerol after exposure to both the PMMA substrate containing $Si_3N_4$, with little differences between the two. In the spectrum of C. albicans exposed to PMMA (FIG. 10C) no fingerprints for nitrosative, osmotic, or oxidative stress were found. In the absence of stress-related features, the spectroscopic response of the yeast cells to pure PMMA differed greatly from cells exposed to the PMMA/$Si_3N_4$. The normalized Raman spectrum for 24 h exposure to the PMMA substrate was like that of the as-cultured cells (cf. FIGS. 10A and 10C). However, despite the spectral similarity, there were differences in relative intensities at different frequency intervals: bands between 860 and 940 $cm^{-1}$ decreased, while bands between 495 and 535 $cm^{-1}$ increased for cells exposed to the PMMA as compared to as-cultured cells (cf. FIGS. 10A and 10C). These two spectral zones are strongly contributed by polyol and disaccharides. The changes in the spectral intensity of Raman bands for these two species suggest a variation in their balance during cell proliferation. Unfortunately, the strong overlap of bands from different chemical species makes it difficult to univocally interpret the observed spectral changes. In other words, the automatic solver algorithm could not single out any sub-band only belonging to D-arabitol molecules. Nevertheless, one plausible interpretation of the Raman data is based on the following observations: (i) Band 19 (at 661 $cm^{-1}$), which corresponds to a strong signal from D-arabitol, was found to increase after exposure to the PMMA substrate; and, (ii) the doublet 20 and 21 (at 663 and 670 $cm^{-1}$, respectively), which is primarily contributed by C—S bonds in DNA cysteine and proteins, was also similarly enhanced by the exposure to PMMA. These two observations point at an expenditure of glycerol to enhance the D-arabitol content and an increase in protein production/duplication of chromosomes, respectively. These are fundamental events in the life cycle of C. albicans and are similar to the replications occurring in both prokaryotes and eukaryotes.

In situ Raman spectroscopy provided fundamental information about the metabolic response of C. albicans to the PMMA/$Si_3N_4$ substrate. Three fingerprints have been identified, which relate to the yeast membrane, the pH of its cytoplasmic environment, and the thiol groups of cysteines in proteins.

Membrane Polysaccharides

An important observation was that the Raman bands of trehalose were not altered by the presence of $Si_3N_4$. This result is consistent with the notion that a direct cleavage of the glycosidic bond by ammonia is thermodynamically unlikely. In fact, the intensity of the C—O bending Band 38 at ~850 $cm^{-1}$ remained unaffected. However, the presence of ammonia/ammonium affected the ring structure and this could be the cause for the disappearance of Band 12, which is related to the α-glucose ring-deformation vibrations.

Nitrosylated Thiol-Containing Proteins and the Key-Role of Ergosterol

It is believed that the Raman spectroscopic indication of substantial ergosterol increase in the presence of $Si_3N_4$ could be related to an excess amount of NO, $ONOO^-$ and other RNS. Nitrosative stress usually refers to conditions in which a flux of NO (or other RNS) starts to induce nitrosylated thiols and amines. This is the fingerprint that was observed in the Raman spectrum of C. albicans in the presence of $Si_3N_4$: nitrosative modifications of thiol-containing proteins with increased intensity of S—N signals (Band 4) and appearance of new spectral bands related to stretch and bending of nitridated S—N—O bonds (Bands 23* and 42*, respectively).

It was previously revealed that the ergosterol lipid is secreted by fungal species to regulate membrane fluidity and to induce macrophages' pyroptosis. This later action was confirmed by comparing the effect of ergosterol-containing and ergosterol-free liposomes in a macrophage pyroptosis model finding that only the former could induce pyroptosis-mediated macrophage lysis. Ergosterol is in the outer mannoprotein layer of the fungal cell walls, consistent with the hypothesis of a trans-cell wall transport mechanism through extracellular vesicles. The fluorescence images in FIGS. 5A-5B and the in situ Raman maps in FIGS. 12C and 12D are in agreement with the view that fungal ergosterol fulfills immunological functions and supports the concept that fungal sterol has a broad distribution within the cell rather than being limited to the plasma membrane. FIG. 14 shows that ergosterol molecules are not only located in the plasma membrane but also have a broad distribution in the fungal cell.

Indeed, the observed nitrosative stress by $Si_3N_4$ mimics similar macrophage chemistry for counteracting pathogens. Based on this similarity, the Raman fingerprints of nitrosylated thiols and amines, and the observation of enhanced ergosterol synthesis (by two independent analytical methods), C. albicans may interpret the exogenous presence of NO, $ONOO^-$ and other RNS formed at the surface of $Si_3N_4$ as a host's immune response and, accordingly, overexpresses ergosterol biosynthesis to increase its virulence against the "presumed" presence of macrophages.

Glycerol and the Yeast Reaction to Osmotic Stress

As previously stated, $NH_3$ is a volatile molecule that forms at the surface of $Si_3N_4$ in water and freely penetrates the yeast membrane. Unprotonated ammonia is osmotically active and possesses the same hydration shell size as ionic potassium, K. Thus, $NH_3$ can contribute to increased endocytic pH, and it can alter the cell's volume via osmosis by formation of $NH_4^+$ ions. To counteract swelling, the yeast increases the production of glycerol (cf. in situ Raman maps in FIGS. 13C and 13D). Glycerol is a polyol that forms hydrates to decrease the energy of its hydroxyl groups. It plays an intrinsic protective function as an osmolyte (in addition to other important metabolic roles, including biofilm formation). Upon opening the membrane channels, the yeast attempts to restore its normal cell volume using an efflux of water carried by glycerol osmolytes. Adaptation of C. albicans to salt stress involves accumulation of the glycerol osmolyte (together with the transient reduction in ribosome biogenesis and translation that usually accompanies stress states). While the present Raman results reinforce the view that ammonia plays a direct role in the candidacidal action of $Si_3N_4$, they also support findings by others showing how osmotic stress adaptation in *C. albicans* relies on glycerol as a key osmolyte.

The Importance of $Si_3N_4$ in Innovative Dental Applications

The present study demonstrated that the presence of a minor fraction of $Si_3N_4$ in PMMA induces both chemical and osmotic stresses in *C. albicans*. The chemically mediated stress occurred when NO and other RNS production exceeded the compensatory capacity of the cells. It culminated in the formation of nitrosylated end products, which were detected by in situ Raman spectroscopy. Conversely, the presence of exogenous ammonia in the cytoplasmic space and the related pH enhancement resulted in increased osmotic stress. The yeast reacted with its typical metabolic pattern of resistance to oxidative and nitrosative stress by enhancing the production of ergosterol and glycerol to arrest the RNS attack and to detoxify ammonia, respectively. FIG. 14 provides a schematic diagram of the metabolic response of *C. albicans* to the chemical reactions taking place at the surface of $Si_3N_4$.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An antifungal composite comprising:
    a thermoplastic polymer comprising a poly(methyl methacrylate) (PMMA) resin; and
    a $Si_3N_4$ powder loaded in at least a portion of the thermoplastic polymer,
    wherein the $Si_3N_4$ is present in a concentration sufficient to reduce or prevent a fungus from growing on the antifungal composite, and
    wherein the $Si_3N_4$ powder is present in a concentration of about 1 vol. % to about 30 vol. %.

2. The antifungal composite of claim 1, wherein the $Si_3N_4$ powder is present in a concentration of about 15 vol. %.

3. The antifungal composite of claim 1, wherein the $Si_3N_4$ powder is mixed homogenously throughout the thermoplastic polymer.

4. The antifungal composite of claim 1, wherein the fungus is a yeast.

5. The antifungal composite of claim 4, wherein the yeast is *Candida albicans*.

6. The antifungal composite of claim 5, wherein the antifungal composite has increased candidacidal efficacy against the fungus as compared to the thermoplastic polymer alone.

7. The antifungal composite of claim 1, wherein the antifungal composite subjects the fungus to nitrosative and osmotic stress.

8. The antifungal composite of claim 1, wherein the antifungal composite creates an alkaline pH when in an aqueous environment.

9. The antifungal composite of claim 8, wherein the aqueous environment near the antifungal composite has a pH of about 8.4.

10. A biocompatible device comprising the antifungal composite of claim 1.

11. The biocompatible device of claim 10, wherein the device comprises a dental device.

12. The biocompatible device of claim 11, wherein the dental device is selected from abiotic dentures, cements, and other dental prostheses.

13. The biocompatible device of claim 10, wherein the $Si_3N_4$ powder is present in a concentration of about 15 vol. %.

14. The biocompatible device of claim 10, wherein the $Si_3N_4$ powder is mixed homogenously throughout the thermoplastic polymer.

15. A method of reducing or preventing a fungus from growing on a biocompatible device comprising:
    placing the biocompatible device of claim 10 in a patient; and
    contacting the biocompatible device with the fungus.

16. The method of claim 15, wherein the fungus is a yeast.

17. The method of claim 16, wherein the yeast is *Candida albicans*.

18. The method of claim 17, wherein the antifungal composite has increased candidacidal efficacy against the fungus as compared to the thermoplastic polymer alone.

19. The method of claim 15, wherein the antifungal composite subjects the fungus to nitrosative and osmotic stress.

20. The method of claim 15, wherein the antifungal composite creates an alkaline pH when in an aqueous environment.

21. The method of claim 20, wherein the aqueous environment near the antifungal composite has a pH of about 8.4.

* * * * *